United States Patent
Yokota et al.

(10) Patent No.: US 11,260,134 B2
(45) Date of Patent: Mar. 1, 2022

(54) DOUBLE-STRANDED NUCLEIC ACID COMPLEX HAVING OVERHANG

(71) Applicant: NATIONAL UNIVERSITY CORPORATION TOKYO MEDICAL AND DENTAL UNIVERSITY, Tokyo (JP)

(72) Inventors: Takanori Yokota, Tokyo (JP); Kotaro Yoshioka, Tokyo (JP)

(73) Assignee: NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 0 days.

(21) Appl. No.: 16/337,808

(22) PCT Filed: Sep. 29, 2017

(86) PCT No.: PCT/JP2017/035553
§ 371 (c)(1),
(2) Date: Mar. 28, 2019

(87) PCT Pub. No.: WO2018/062510
PCT Pub. Date: Apr. 5, 2018

(65) Prior Publication Data
US 2019/0240352 A1 Aug. 8, 2019

(30) Foreign Application Priority Data
Sep. 29, 2016 (JP) .............................. JP2016-191548

(51) Int. Cl.
| | | |
|---|---|---|
| *A61K 48/00* | (2006.01) |
| *A61K 9/00* | (2006.01) |
| *A61P 25/28* | (2006.01) |
| *A61K 31/7125* | (2006.01) |
| *A61P 35/00* | (2006.01) |
| *A61K 9/70* | (2006.01) |
| *C12N 15/09* | (2006.01) |
| *C12N 15/113* | (2010.01) |
| *A61K 31/7088* | (2006.01) |

(52) U.S. Cl.
CPC ........ *A61K 48/0066* (2013.01); *A61K 9/0019* (2013.01); *A61K 9/7023* (2013.01); *A61K 31/7088* (2013.01); *A61K 31/7125* (2013.01); *A61K 48/00* (2013.01); *A61P 25/28* (2018.01); *A61P 35/00* (2018.01); *C12N 15/09* (2013.01); *C12N 15/113* (2013.01)

(58) Field of Classification Search
None
See application file for complete search history.

(56) References Cited

U.S. PATENT DOCUMENTS

| | | |
|---|---|---|
| 10,329,567 B2 | 6/2019 | Yokota et al. |
| 10,337,006 B2 | 7/2019 | Yokota et al. |
| 10,844,374 B2 | 11/2020 | Yokota et al. |
| 2005/0255086 A1* | 11/2005 | Davidson ............. C12N 15/113 424/93.2 |
| 2009/0298916 A1 | 12/2009 | Kauppinen et al. |
| 2011/0003881 A1 | 1/2011 | Brown |
| 2011/0046206 A1* | 2/2011 | Bhat .............. C12Y 301/03048 514/44 R |
| 2011/0300182 A1 | 12/2011 | Yokozeki et al. |
| 2020/0115710 A1 | 4/2020 | Yokota et al. |

FOREIGN PATENT DOCUMENTS

| | | |
|---|---|---|
| EP | 2631291 A2 | 8/2013 |
| EP | 2774989 A1 | 9/2014 |
| JP | 2010-503382 A | 2/2010 |
| JP | 2010-068723 A | 4/2010 |
| JP | 2012-502991 A | 2/2012 |
| JP | 2016-524588 A | 8/2016 |
| WO | 02/44321 A2 | 6/2002 |
| WO | 2004/083430 A2 | 9/2004 |
| WO | 2006/102970 A2 | 10/2006 |
| WO | 2008/011431 A2 | 1/2008 |
| WO | 2010/033246 A1 | 3/2010 |
| WO | 2013/089283 A1 | 6/2013 |

(Continued)

OTHER PUBLICATIONS

Makiko Hamada, et al., "Effects on RNA Interference in Gene Expression (RNAi) in Cultured Mammalian Cells of Mismatches . . . ", Antisense & Nucleic Acid Drug Development, vol. 12, No. 5, pp. 301-309, 2002.
Hiroyuki Ida, et al., Long DNA Passenger Strand Highly Improves the Activity of RNA/DNA Hybrid siRNAs, Journal of Bioscience and Bioengineering, vol. 117, No. 4, pp. 401-406, 2014.
Supplemental European Search Report corresponding to European Application No. 17856457.1 dated Apr. 20, 2020, (9 pages).
Nishina, K., et al., DNA/RNA heteroduplex oligonucleotide for highly efficient gene silencing, Nature Communications, 2015, vol. 6: 7969, DOI: 10. 1038/ncomms8969, pp. 1-13, ISSN2041-1723 (online).

(Continued)

*Primary Examiner* — Tracy Vivlemore
(74) *Attorney, Agent, or Firm* — Lucas & Mercanti, LLP

(57) ABSTRACT

Provided is a nucleic acid strand that can efficiently deliver an antisense oligonucleotide into the body, particularly a nucleic acid complex comprising a first nucleic acid strand and a second nucleic acid strand, wherein the first nucleic acid strand includes a base sequence that is capable of hybridizing with at least a portion of a target transcription product, and exerts an antisense effect on the target transcription product; the second nucleic acid strand includes a complementary region having a base sequence complementary to the first nucleic acid strand and at least one overhang region located on the 5' and/or 3' side of the complementary region; and the first nucleic acid strand is annealed to the complementary region in the second nucleic acid strand.

12 Claims, 32 Drawing Sheets

Specification includes a Sequence Listing.

(56) References Cited

FOREIGN PATENT DOCUMENTS

| WO | WO-2013089283 A1 | * | 6/2013 | ............ A61P 43/00 |
|----|------------------|---|--------|-------------------------|
| WO | 2014/132671 A1 |   | 9/2014 | |
| WO | 2014/192310 A1 |   | 12/2014 | |
| WO | 2014/203518 A1 |   | 12/2014 | |
| WO | 2015/140330 A1 |   | 9/2015 | |

OTHER PUBLICATIONS

Kuwahara, H., et al., Nano-DDS for oligonucleotide therapeutics, 2015, vol. 34, No. 10, pp. 939-945, ISSN 0287-3796, in particular, fig. 1. (Cell technology).

Ohyagi, M., et al., Oligonucleotide therapeutics for treatment of neurological degenerative diseases, Aug. 15, 2016, vol. 67, No. 4, pp. 349-353, ISSN 0370-9531, in particular, fig. p. 350, non-official translation (Seitai No Kagaku).

Kunieda, T., et al., A new type of double stranded antisense oligonucleotide: overhanging duplex oligonucleotide (ODO), Nov. 1, 2016, p. 118, non-official translation (The 2st Nucleic Acids Therapeutics Society of Japan: abstracts).

Rettig, Garrett R; et al., "Progress Toward In Vivo Use of siRNAs-II", Molecular Therapy, vol. 20(3), 2012, pp. 483-512.

European Patent Office, "communication pursuant to Article 94(3)" issued in connection with European patent application No. 17856457.1, dated Dec. 21, 2020 (6 pages).

* cited by examiner

Fig. 12
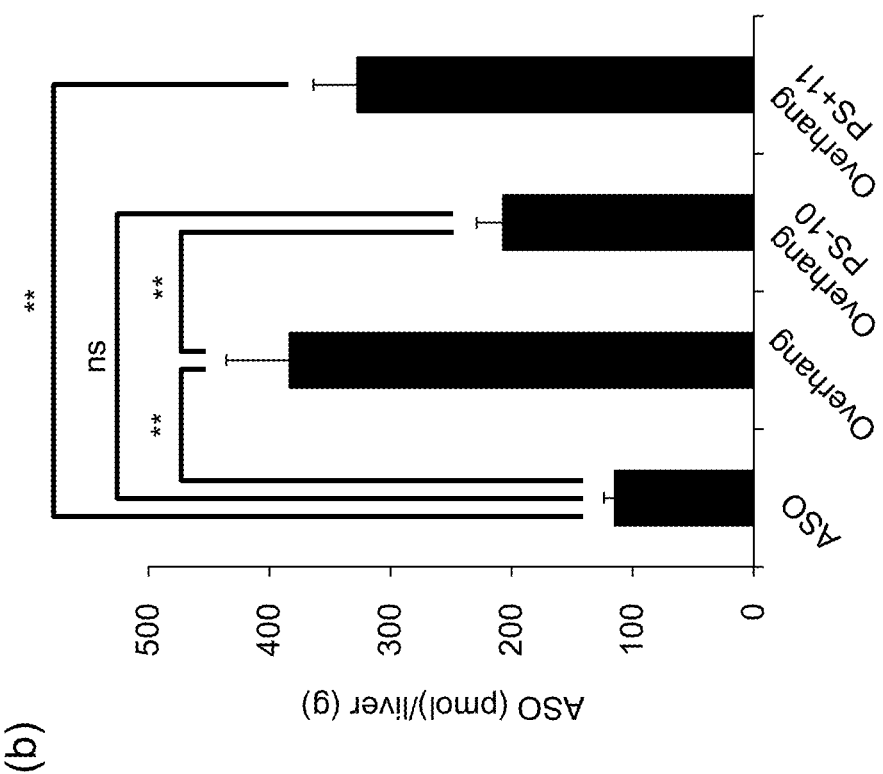
(a)
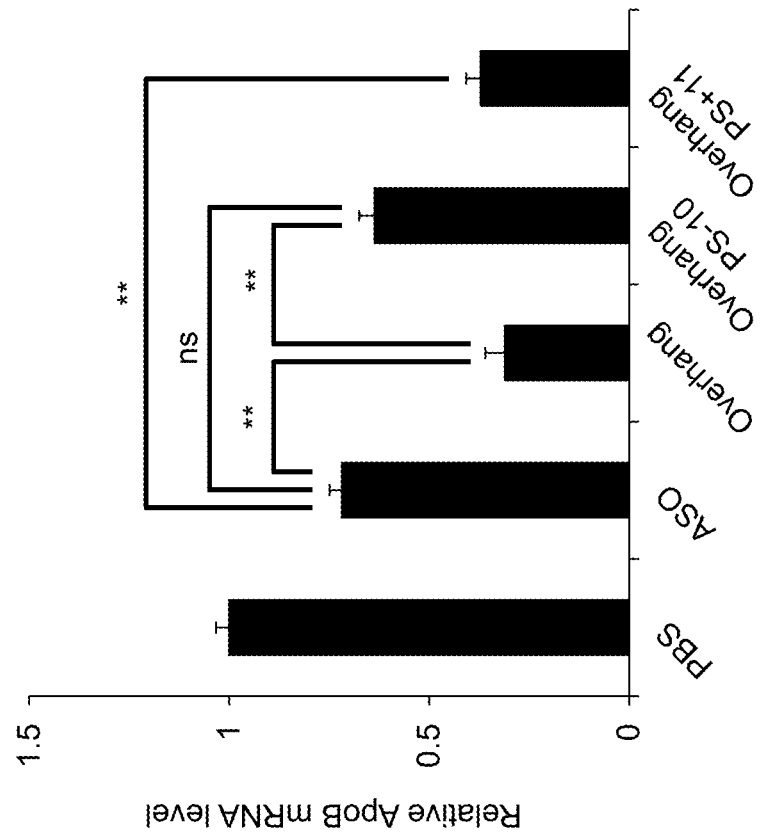
(b)

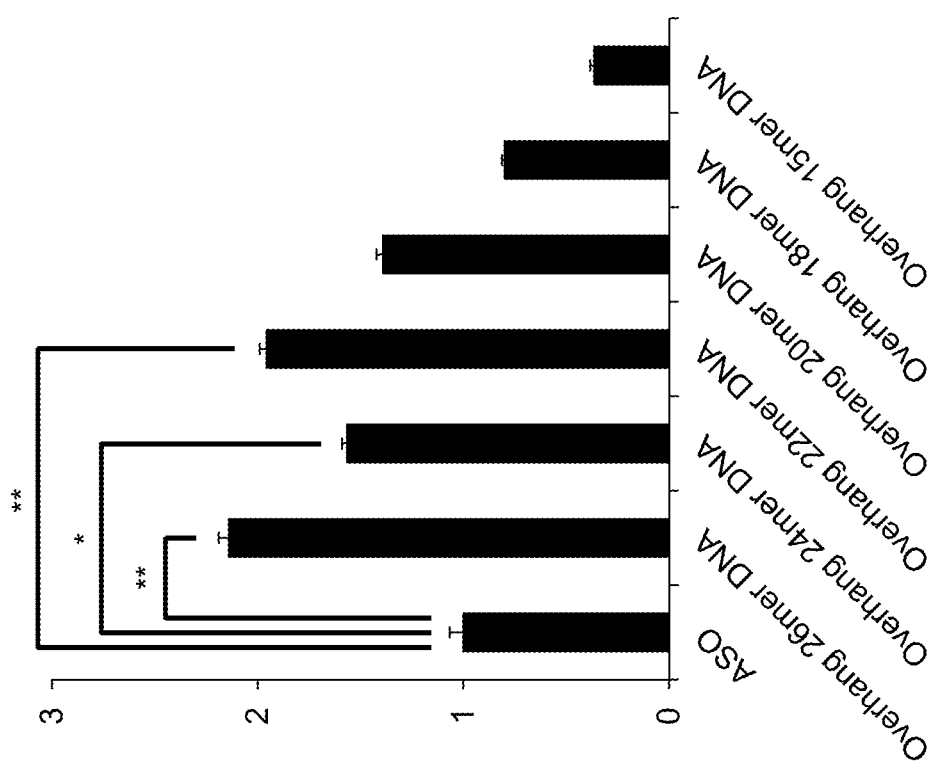
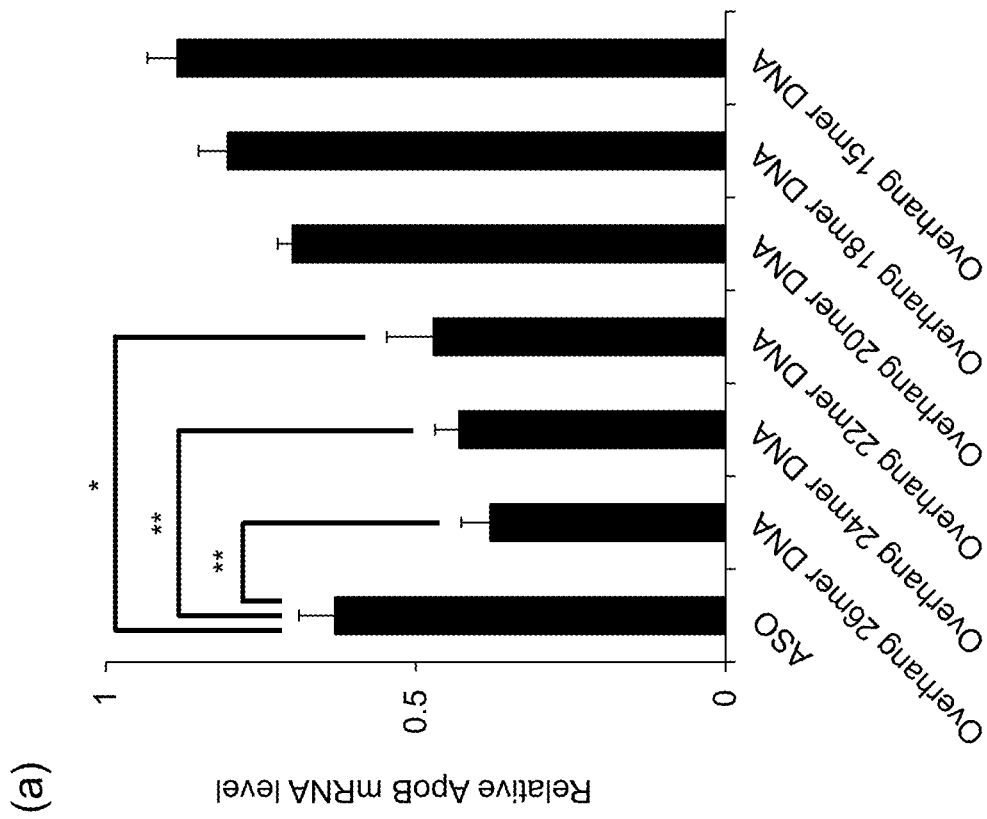
Fig. 14

Fig. 16
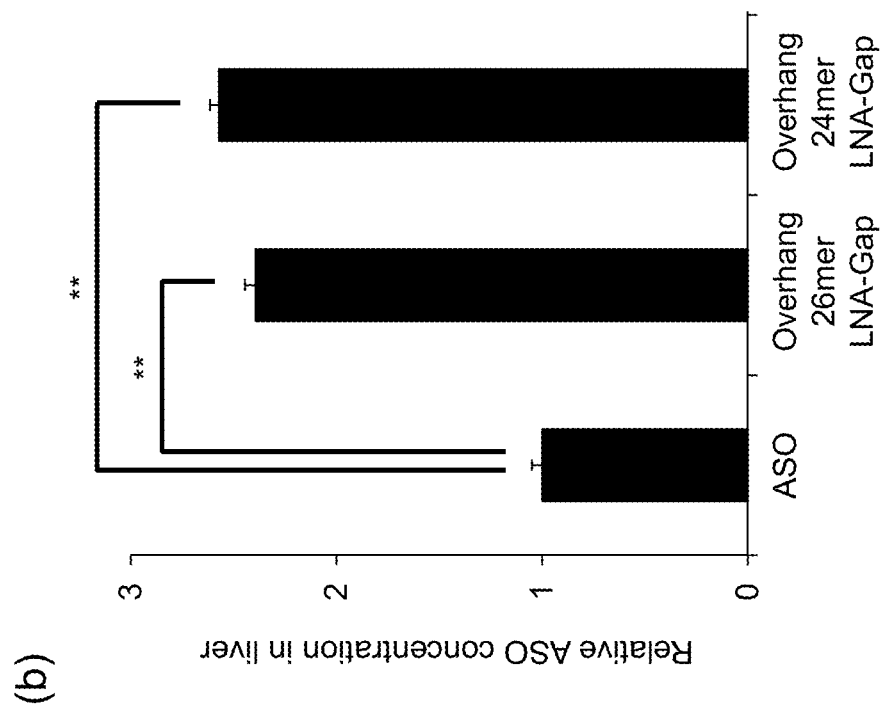
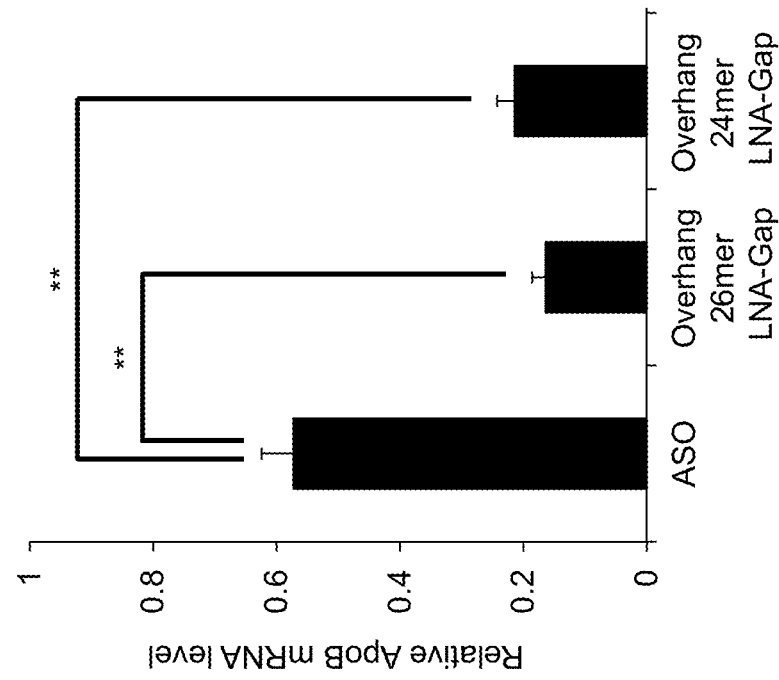

DOUBLE-STRANDED NUCLEIC ACID COMPLEX HAVING OVERHANG

CROSS-REFERENCE TO RELATED APPLICATIONS

This application is a 371 of PCT/JP2017/035553, filed Sep. 29, 2017, which claims benefit of Japanese Patent Application No. 2016-191548 filed on Sep. 29, 2016.

REFERENCE TO A SEQUENCE LISTING SUBMITTED ELECTRONICALLY VIA EFS-WEB

The content of the electronically submitted sequence listing, file name: 522-1146 Sequence Listing.txt; size: 117,356 bytes; and date of creation: Mar. 28, 2019, filed herewith, is incorporated herein by reference in its entirety.

TECHNICAL FIELD

The present invention relates to a double-stranded nucleic acid complex having an overhang, wherein the complex has an activity of inhibiting target gene expression through an antisense effect.

BACKGROUND ART

Recently oligonucleotides have been drawing attention in the ongoing development of pharmaceuticals called nucleic acid medicine. In particular, nucleic acid medicine using an antisense method is being actively developed, taking the high selectivity for target genes and the low toxicity into consideration. An antisense method includes a method in which the expression of a protein encoded by a target gene is selectively modified or inhibited by introducing an oligonucleotide (for example, an antisense oligonucleotide, in other words, ASO) complementary to a partial sequence of mRNA (a sense strand) of the target gene into cells. Similarly, the antisense method targets miRNA and functions to modify the activity of such a miRNA.

As a nucleic acid utilizing an antisense method, a double-stranded nucleic acid complex obtained by annealing an antisense oligonucleotide and a strand complementary thereto was been developed by the present inventors (Patent Literature 1). Patent Literature 1 discloses that an antisense oligonucleotide annealed to a complementary strand conjugated to a tocopherol, which has a function of specific delivery to a target site (liver), is efficiently delivered to the liver and also has a high antisense effect.

The present inventors also developed a double-stranded antisense nucleic acid having an exon-skipping effect (Patent Literature 2) and a short gapmer antisense oligonucleotide wherein an additional nucleotide is added to the 5' end, 3' end, or both the 5' end and 3' end of the gapmer (antisense oligonucleotide) (Patent Literature 3). The present inventors also developed a double-stranded agent for delivering therapeutic oligonucleotides (Patent Literature 4).

CITATION LIST

Patent Literature

Patent Literature 1: International Publication No. WO2013/089283
Patent Literature 2: International Publication No. WO2014/203518
Patent Literature 3: International Publication No. WO2014/132671
Patent Literature 4: International Publication No. WO2014/192310

SUMMARY OF INVENTION

Technical Problem

A problem to be solved by the present invention is to provide a nucleic acid strand that can efficiently deliver an antisense oligonucleotide into a living body to produce an antisense effect.

Solution to Problem

The inventors intensively studied to solve the above-described problem and consequently found that a nucleic acid complex formed by annealing an antisense oligonucleotide to a complementary strand having an overhang region is efficiently delivered into a living body and exerts a high antisense effect in a living body, and completed the present invention.

The present invention thus includes the following.
[1] A nucleic acid complex comprising a first nucleic acid strand and a second nucleic acid strand,
wherein the first nucleic acid strand comprises a base sequence that is capable of hybridizing with at least part of a target transcription product;
wherein the first nucleic acid strand has an antisense effect on the target transcription product;
wherein the second nucleic acid strand comprises a complementary region comprising a base sequence complementary to the first nucleic acid strand and at least one overhang region located on the 5' terminal and/or 3' terminal side of the complementary region; and
wherein the first nucleic acid strand is annealed to the complementary region in the second nucleic acid strand.
[2] The nucleic acid complex according to [1], wherein the overhang region in the second nucleic acid strand is at least nine bases in length.
[3] The nucleic acid complex according to [1] or [2], wherein the first nucleic acid strand is 13 to 20 bases in length.
[4] The nucleic acid complex according to any one of [1] to [3], wherein the second nucleic acid strand is 30 bases or less in length.
[5] The nucleic acid complex according to any one of [1] to [4], wherein at least one internucleoside linkage from the free end of the overhang region in the second nucleic acid strand is a modified internucleoside linkage.
[6] The nucleic acid complex according to any one of [1] to [5], wherein at least 50% of the internucleoside linkages within the overhang region in the second nucleic acid strand are modified internucleoside linkages.
[7] The nucleic acid complex according to [5] or [6], wherein the modified internucleoside linkage is a phosphorothioate linkage.
[8] The nucleic acid complex according to any one of [1] to [7], wherein at least one nucleoside from the free end of the overhang region in the second nucleic acid strand is a modified nucleoside.
[9] The nucleic acid complex according to [8], wherein the modified nucleoside comprises a bicyclic sugar.
[10] The nucleic acid complex according to any one of [1] to [9], wherein the first nucleic acid strand is a BNA/DNA gapmer, a BNA/DNA mixmer, or a BNA/RNA mixmer.

[11] The nucleic acid complex according to any one of [1] to [10], wherein the first nucleic acid strand comprises a peptide nucleic acid and/or a morpholino nucleic acid.
[12] The nucleic acid complex according to any one of [1] to [11], wherein the first nucleic acid strand comprises at least one modified nucleoside and the modified nucleoside comprises a 2'-O-methyl group-containing sugar.
[13] The nucleic acid complex according to any one of [1] to [12], wherein the second nucleic acid strand further comprises a functional moiety having a function selected from a labeling function, a purification function, and a target delivery function.
[14] The nucleic acid complex according to any one of [1] to [13], wherein the overhang region in the second nucleic acid strand is not a therapeutic oligonucleotide region.
[15] The nucleic acid complex according to any one of [1] to [14], wherein the complementary region in the second nucleic acid strand does not comprise at least two consecutive ribonucleosides.
[16] The nucleic acid complex according to any one of [1] to [15], wherein the overhang region in the second nucleic acid strand comprises a modified nucleoside comprising a bicyclic sugar and is 9 to 12 bases in length.
[17] The nucleic acid complex according to any one of [1] to [15], wherein the overhang region in the second nucleic acid strand does not comprise a modified nucleoside comprising a bicyclic sugar and is 9 to 17 bases in length.
[18] A composition comprising the nucleic acid complex according to any one of [1] to [17] and a pharmaceutically acceptable carrier.
[19] The composition according to [18], wherein the composition is for intravenous administration, intraventricular administration, intrathecal administration, intramuscular injection administration, continuous infusion administration, intraperitoneal administration, inhalation, skin patch, or subcutaneous administration.

The present application claims the priority to Japanese Patent Application No. 2016-191548, the disclosure of which is herein incorporated.

Advantageous Effects of Invention

The present invention provides a nucleic acid strand that can efficiently deliver an antisense oligonucleotide into a living body to produce an antisense effect.

BRIEF DESCRIPTION OF DRAWINGS

FIG. 12 shows graphs showing the results of experiments described in Example 4, comparing (a) the inhibitory effects on a target gene (ApoB) and (b) the antisense oligonucleotide concentrations in the liver by a nucleic acid complex according to a particular embodiment. The double asterisk (**) indicates $p<0.01$. The sign "ns" indicates no significant difference.
FIG. 14 shows graphs showing the results of experiments described in Example 5, comparing (a) the inhibitory effects on the expression of a target gene (ApoB) and (b) the antisense oligonucleotide concentrations in the liver by a nucleic acid complex according to a particular embodiment. The single asterisk (*) indicates $p<0.05$, and the double asterisk (**) indicates $p<0.01$.
FIG. 16 shows graphs showing the results of experiments described in Example 6, comparing (a) the inhibitory effects on the expression of a target gene (ApoB) and (b) the antisense oligonucleotide concentrations in the liver by a nucleic acid complex according to a particular embodiment. The double asterisk (**) indicates $p<0.01$.

DESCRIPTION OF EMBODIMENTS

<Nucleic Acid Complex>

The present invention relates to a nucleic acid complex. The nucleic acid complex comprises a first nucleic acid strand and a second nucleic acid strand. In the nucleic acid complex according to the present invention, the first nucleic acid strand is a nucleotide strand comprising a base sequence that is capable of hybridizing with at least part of a target transcription product. The first nucleic acid strand is a nucleotide strand having an antisense effect on the transcription product of a target gene or on a target transcription product.

The second nucleic acid strand is a nucleotide strand comprising a complementary region comprising a base sequence complementary to the first nucleic acid strand and at least one overhang region located on the 5' terminal and/or 3' terminal side of the complementary region. The "overhang region" refers to a nucleotide region in the second nucleic acid strand wherein the 5' end of the second nucleic acid strand extends beyond the 3' end of the first nucleic acid strand, and/or wherein the 3' end of the second nucleic acid strand extends beyond the 5' end of the first nucleic acid strand when the first and second nucleic acid strands are annealed to each other to form a duplex structure, namely a nucleotide region protruding from the duplex structure. The overhang region is adjacent to the complementary region.

In the nucleic acid complex according to the present invention, the first nucleic acid strand is annealed to the complementary region in the second nucleic acid strand.

Figure 1:
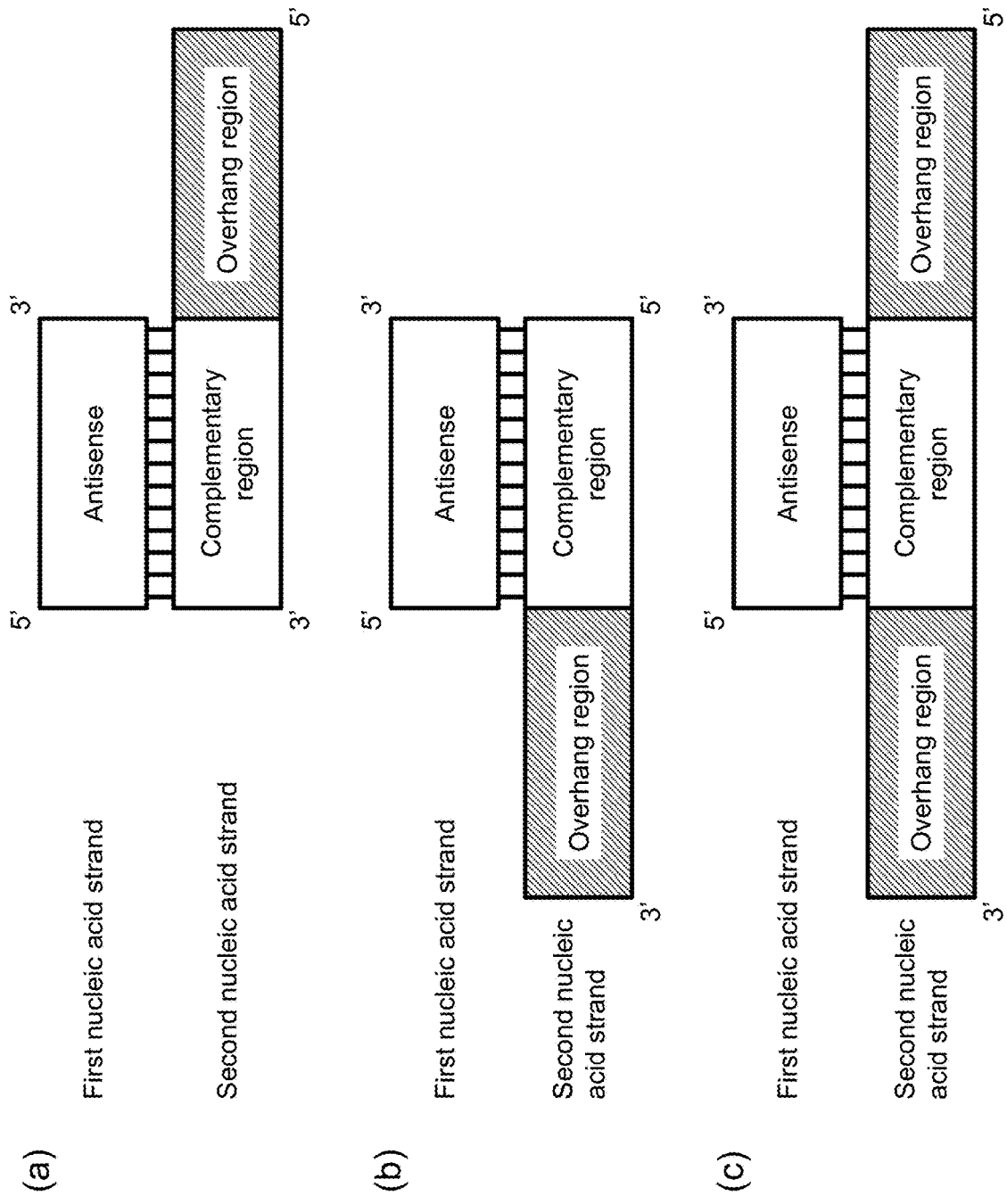
FIG. 1 shows a schematic diagram showing an example of a particular embodiment of a nucleic acid complex according to the present invention.

Representative schematic diagrams of nucleic acid complexes according to the present invention are shown in FIG. 1. An overhang region in the second nucleic acid strand may be located on either the 5' terminal side (FIG. 1a) or the 3' terminal side (FIG. 1b) of the complementary region. Overhang regions in the second nucleic acid strand may be located on the 5' terminal and 3' terminal sides (FIG. 1c) of the complementary region. One overhang region may be located on either the 5' terminal side or the 3' terminal side of the complementary region, or two overhang regions may be located on the 5' terminal and 3' terminal sides of the complementary region.

Figure 3:
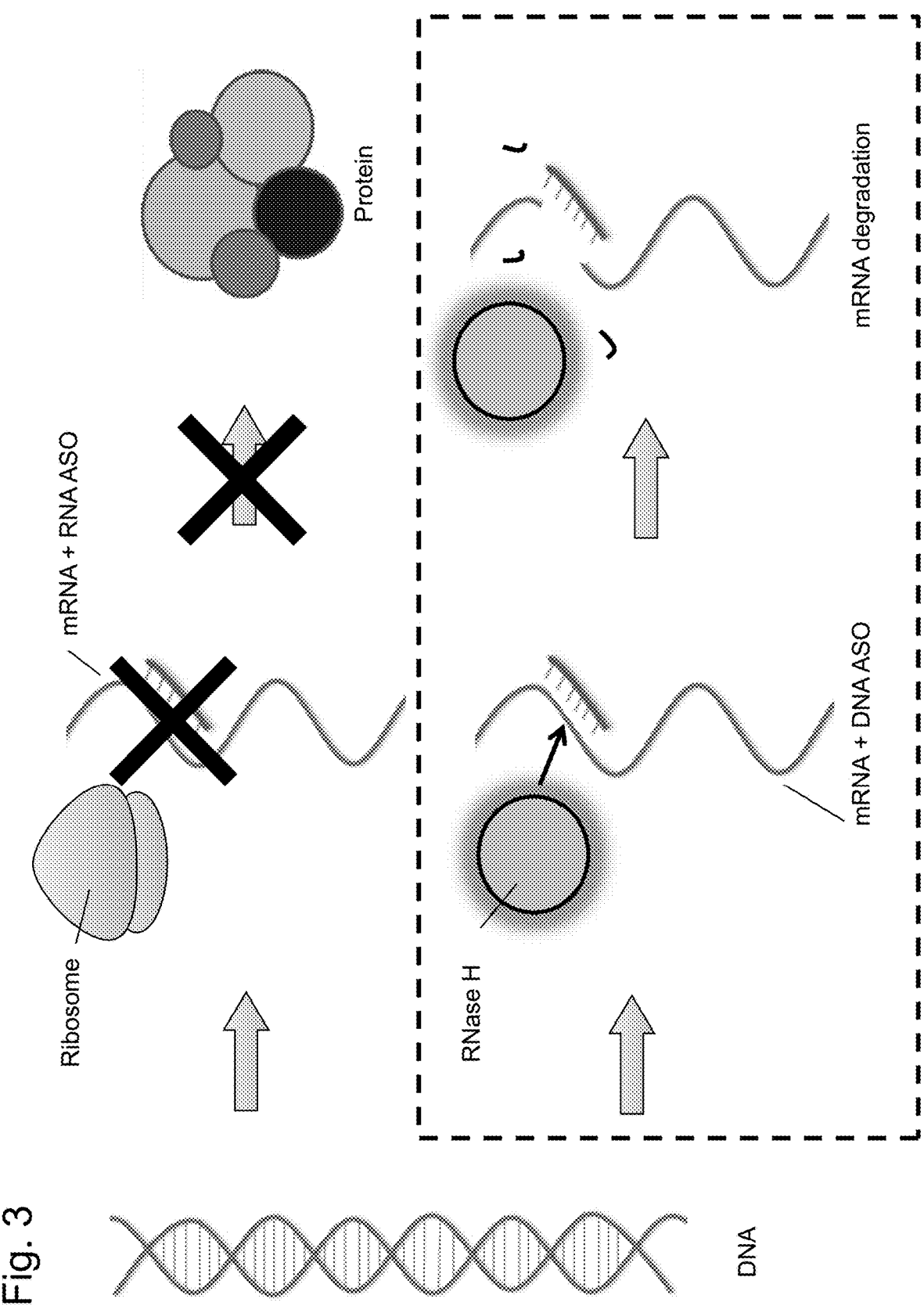
FIG. 3 shows an example of a general mechanism of the antisense method.

An "antisense effect" refers to suppression or reduction of expression of a target gene or the level of a target transcription product, wherein the suppression or reduction results from hybridization between a target transcription product (RNA sense strand) and, for example, a DNA strand or, more commonly, a strand that is complementary to a partial sequence of the transcription product and the like and designed to cause an antisense effect. In a specific example, translation inhibition or a splicing function modification effect, for example, exon-skipping can be caused by hybridization of an antisense oligonucleotide (for example, a first nucleic acid strand) with a transcription product (see the depiction in the upper part outside the area surrounded by the dotted line in FIG. 3). Alternatively, degradation of a transcription product can result from recognition of the hybridized portion (see the depiction in the area surrounded by the dotted line in FIG. 3). For example, in translation inhibition, an RNA-containing oligonucleotide introduced as an antisense oligonucleotide (ASO) into a cell binds to a transcription product (mRNA) of a target gene to form a partial double-strand. This double-strand plays a role as a cover for inhibiting translation by ribosome, and accordingly, the expression of the protein encoded by the target gene is inhibited (the upper part in FIG. 3). On the other hand, a DNA-containing oligonucleotide introduced as an ASO into a cell forms a partial DNA-RNA heteroduplex. This structure is recognized by an RNase H, and, as a result, the mRNA of the target gene is degraded, and accordingly, the expression of the protein encoded by the target gene is inhibited (see the lower part in FIG. 3). This is referred to as an RNase-H-dependent pathway. Furthermore, in a specific example, an antisense effect can be caused by targeting an intron of a pre-mRNA. An antisense effect can also be caused by targeting an miRNA. In this case, the function of the miRNA is inhibited, and the expression of a gene which is usually regulated by the miRNA can increase.

An "antisense oligonucleotide" or "antisense nucleic acid" refers to a single-stranded oligonucleotide which comprises a base sequence capable of hybridizing with (in other words, complementary to) at least part of a transcription product of a target gene or a target transcription product and which can suppress expression of the transcription product of the target gene or the level of the target transcription product mainly through an antisense effect.

Examples of "target genes" or "target transcription products" the expression of which is suppressed, changed, or modified by an antisense effect include, but are not limited particularly to, genes derived from an organism to which a nucleic acid complex according to the present invention is introduced, for example, genes the expression of which is increased in various diseases. In addition, a "transcription product of a target gene" is an mRNA transcribed from a genome DNA encoding a target gene, and examples of such products further include mRNAs that have not undergone base modifications, mRNA precursors that have not undergone processing, and the like. Examples of "target transcription products" can include not only mRNAs but also non-coding RNAs (ncRNA) such as miRNAs.

Furthermore, more generally, a "transcription product" may be any RNA synthesized by a DNA-dependent RNA polymerase. In one embodiment, a "target transcription product" may be, for example, apolipoprotein B (ApoB) mRNA, scavenger receptor B1 (SRB1) mRNA, metastasis associated lung adenocarcinoma transcript 1 (MALAT1) non-coding RNA, microRNA-122 (miR-122), beta-secretase 1 (BACE1) mRNA, or PTEN (Phosphatase and Tensin Homolog Deleted from Chromosome 10) mRNA. The base sequences of the mouse and human ApoB mRNAs are represented by SEQ ID NOs: 1 and 52, respectively (base sequences of mRNAs are shown as base sequences of DNAs). The base sequences of the mouse and human SRB1 mRNAs are represented by SEQ ID NOs: 2 and 53, respectively (base sequences of mRNAs are shown as base sequences of DNAs). The base sequences of the mouse and human MALAT1 non-coding RNAs are represented by SEQ ID NOs: 3 and 54, respectively (base sequences of RNAs are shown as base sequences of DNAs). The base sequence of the mouse miR-122 is represented by SEQ ID NO: 4. The base sequence of the human miR-122 is the same as that of the mouse counterpart. The base sequences of the mouse and human BACE1 mRNAs are represented by SEQ ID NOs: 5 and 55, respectively (base sequences of mRNAs are shown as base sequences of DNAs). The base sequences of the mouse and human PTEN mRNAs are represented by SEQ ID NOs: 6 and 56, respectively (base sequences of mRNAs are shown as base sequences of DNAs). The base sequences of the genes and transcription products are available from public databases, such as, for example, NCBI (United States National Center for Biotechnology Information) databases. The base sequence of microRNAs are available from, for example, miRBase database (Kozomara A, Griffiths-Jones S. NAR 2014 42:D68-D73; Kozomara A, Griffiths-Jones S. NAR 2011 39:D152-D157; Griffiths-Jones S, Saini H K, van Dongen S, Enright A J. NAR 2008 36:D154-D158; Griffiths-Jones S, Grocock R J, van Dongen S, Bateman A, Enright A J. NAR 2006 34:D140-D144; Griffiths-Jones S. NAR 2004 32:D109-D111).

The first nucleic acid strand comprises a base sequence that is capable of hybridizing with at least part of a target transcription product (for example, any target region). The target region may include 3'UTR, 5'UTR, an exon, an intron, a coding region, a translation initiation region, a translation termination region, or other nucleic acid regions. The target region of the target transcription product may include, for example, the base sequence of positions 10136 to 10148 of SEQ ID NO: 1 in the case of the mouse ApoB mRNA, the base sequence of positions 2479 to 2491 of SEQ ID NO: 2 in the case of the mouse SRB1 mRNA, the base sequence of positions 1316 to 1331 of SEQ ID NO: 3 in the case of the mouse MALAT1 non-coding RNA, the base sequence of positions 2 to 16 of SEQ ID NO: 4 in the case of miR-122, the base sequence of positions 1569 to 1581 of SEQ ID NO: 5 in the case of the mouse BACE1 mRNA, or the base sequence of positions 59 to 74 of SEQ ID NO: 6 in the case of the mouse PTEN mRNA.

The term "nucleic acid" as used herein may refer to a monomer nucleotide or nucleoside or may mean an oligonucleotide consisting of multiple monomers. The term "nucleic acid strand" or "strand" is also used herein to refer to an oligonucleotide. A nucleic acid strand can be produced entirely or partially by chemical synthesis (for example, using an automatic synthesizer) or by enzymatic process (for example, but not limited to, polymerase reaction, ligase reaction, or restriction reaction).

The term "nucleic acid base" or "base" as used herein means a heterocyclic moiety capable of pairing with another nucleic acid base.

The phrase "a purified or isolated nucleic acid complex" as used herein refers to a nucleic acid complex comprising at least one unnatural nucleic acid strand or comprising essentially no natural nucleic acid substance.

As used herein, the term "complementary" refers to a relationship capable of forming what is called a Watson-Crick base pairing (natural type base pairing) or a non-Watson-Crick base pairing (Hoogsteen base pairing and the like) via hydrogen bonding. In the present invention, the first nucleic acid strand does not necessarily have to be completely complementary to at least part of a target transcription product (for example, a transcription product of a target gene), and the base sequence may have a complementarity of at least 70%, preferably at least 80%, more preferably at least 90% (for example, 95%, 96%, 97%, 98%, or 99% or more). Similarly, the first nucleic acid strand does not necessarily have to be completely complementary to the complementary region of the second nucleic acid strand, and the base sequence may have a complementarity of at least 70%, preferably at least 80%, more preferably at least 90% (for example, 95%, 96%, 97%, 98%, or 99% or more). The complementarity of a sequence can be determined using a BLAST program or the like. The first nucleic acid strand can "hybridize" with a target transcription product in a case where the sequence is complementary (typically, in a case where the sequence is complementary to the sequence of at least part of the target transcription product). The first nucleic acid strand can "anneal" to the complementary region of the second nucleic acid strand in a case where the sequence is complementary. A person skilled in the art can easily determine the conditions (temperature, salt concentration, and the like) that enable two strands to be annealed or hybridized, taking the interstrand complementarity degree into consideration. Typically, such conditions may be physiological conditions. Furthermore, a person skilled in the art can easily design an antisense nucleic acid complementary to a target transcription product, for example, on the basis of information on the base sequence of a target gene.

Hybridization conditions may be, for example, stringent conditions such as low stringent conditions and high stringent conditions. Low stringent conditions may be, for example, 30° C., 2×SSC, and 0.1% SDS. High stringent conditions may be, for example, 65° C., 0.1×SSC, and 0.1% SDS. The stringency of hybridization can be adjusted by changing the conditions such as temperatures and salt concentrations. Here, 1×SSC contains 150 mM sodium chloride and 15 mM sodium citrate.

In an embodiment, an overhang region in the second nucleic acid strand has a base sequence that is not capable of hybridizing with the first nucleic acid strand. The overhang region may comprise a base sequence having a complementarity of 50% or less, 40% or less, 30% or less, 25% or less, 20% or less, 15% or less, 10% or less, 5% or less, or 0% to the base sequence of the first nucleic acid strand.

In an embodiment, an overhang region in the second nucleic acid strand is not a therapeutic oligonucleotide region. Examples of the therapeutic oligonucleotide include antisense oligonucleotides, microRNA inhibitors (anti-miRs), splice-switching oligonucleotides, single-stranded siRNAs, microRNAs, pre-microRNAs, and the like. In a preferred embodiment, an overhang region in the second nucleic acid strand does not have an ability to substantially hybridize to transcription products in a cell and does not influence gene expression.

The base sequence of an overhang region may comprise, for example, a base sequence having an identity of at least 70%, at least 80%, at least 90%, or 100% to the base sequence represented by any of SEQ ID Nos: 7 to 9, a consecutive partial sequence at the 5' terminal side thereof (for example, a partial sequence of at least 9 bases in length, at least 11 bases in length, or at least 13 bases in length), a base sequence obtained therefrom by substituting at least part of thymine (T) to uracil (U). An overhang region may comprise natural nucleotides and/or unnatural nucleotides comprising the above-described base sequence.

A nucleic acid complex according to the present invention does not have to comprise a third nucleic acid strand complementary to an overhang region. Preferably, an overhang region is a single-stranded region.

Typically, the first nucleic acid strand and the complementary region in the second nucleic acid strand may be, but is not limited to, at least 8 bases in length, at least 9 bases in length, at least 10 bases in length, at least 11 bases in length, at least 12 bases in length, at least 13 bases in length, at least 14 bases in length, or at least 15 bases in length. The first nucleic acid strand and the complementary region in the second nucleic acid strand may be 35 bases or less in length, 30 bases or less in length, 25 bases or less in length, 24 bases or less in length, 23 bases or less in length, 22 bases or less in length, 21 bases or less in length, 20 bases or less in length, 19 bases or less in length, 18 bases or less in length, 17 bases or less in length, 16 bases or less in length. The first nucleic acid strand and the complementary region in the second nucleic acid strand may be about 100 bases in length, or may be 10 to 35 bases in length, 12 to 25 bases in length, 13 to 20 bases in length, 14 to 19 bases in length, or 15 to 18 bases in length. The first nucleic acid strand and the complementary region in the second nucleic acid strand may have an identical length or different lengths (for example, lengths different by 1 to 3 bases). The duplex structure formed between the first nucleic acid strand and the complementary region in the second nucleic acid strand may comprise a bulge. In a particular example, the selection of lengths is generally determined depending on, particularly, the balance between the strength of the antisense effect and the specificity of the nucleic acid strands to the target, among other factors such as cost and synthetic yield.

The overhang region in the second nucleic acid strand may be, but not limited to, at least 9 bases in length, at least 10 bases in length, at least 11 bases in length, at least 12 bases in length, or at least 13 bases in length. The overhang region may be 30 bases or less in length, 29 bases or less in length, 28 bases or less in length, 27 bases or less in length, 26 bases or less in length, 25 bases or less in length, 24 bases or less in length, 23 bases or less in length, 22 bases or less in length, 21 bases or less in length, 20 bases or less in length, 19 bases or less in length, 18 bases or less in length, 17 bases or less in length, 16 bases or less in length, 15 bases in length, or 14 bases in length. The overhang region may be, for example, 9 to 20 bases in length, 9 to 18 bases in length, 9 to 17 bases in length, 9 to 12 bases in length, or 11 to 15 bases in length. In a case where there are two overhang regions, the overhang regions may have an identical length or lengths different from each other.

The second nucleic acid strand (comprising a complementary region and an overhang region(s)) may be, but not limited to, 40 bases or less in length, 35 bases or less in length, 30 bases or less in length, 28 bases or less in length, 26 bases or less in length, 24 bases or less in length, or 22 bases or less in length. The second nucleic acid strand (comprising a complementary region and an overhang region(s)) may be at least 18 bases in length, at least 20 bases in length, at least 22 bases in length, or at least 24 bases in length.

In general, a "nucleoside" is a combination of a base and a sugar. The nucleic acid base (known as a base) moiety of a nucleoside is usually a heterocyclic base moiety. A "nucleotide" further comprises a phosphate group covalently bound to the sugar moiety of the nucleoside. In a nucleoside comprising a pentofuranosyl sugar, a phosphate group can be linked to the 2', 3', or 5' hydroxyl moiety of the sugar. An oligonucleotide is formed by covalent bonds between nucleosides adjacent to each other, forming a linear polymer oligonucleotide. In general, phosphate groups are considered to form internucleoside linkages of an oligonucleotide inside the oligonucleotide structure.

Herein, a nucleic acid strand can comprise a natural nucleotide and/or an unnatural nucleotide. Herein, a "natural nucleotide" comprises a deoxyribonucleotide found in DNA and a ribonucleotide found in RNA. Herein, "deoxyribonucleotide" and "ribonucleotide" may be referred to as "DNA nucleotide" and "RNA nucleotide" respectively.

Similarly, a "natural nucleoside" as used herein comprises a deoxyribonucleoside found in DNA and a ribonucleoside found in RNA. Herein, "deoxyribonucleoside" and "ribonucleoside" may be referred to as "DNA nucleoside" and "RNA nucleoside" respectively.

An "unnatural nucleotide" refers to any nucleotide other than a natural nucleotide and encompasses a modified nucleotide and a nucleotide mimic. Similarly, an "unnatural nucleoside" as used herein refers to any nucleoside other than a natural nucleoside and encompasses a modified nucleoside and a nucleoside mimic. Herein, a "modified nucleotide" refers to a nucleotide having any one or more of a modified sugar moiety, a modified internucleoside linkage, and a modified nucleic acid base. Herein, a "modified nucleoside" refers to a nucleoside having a modified sugar moiety and/or a modified nucleic acid base. A nucleic acid strand comprising an unnatural oligonucleotide often has desirable characteristics that allow, for example, enhanced cell uptake, enhanced affinity to a nucleic acid target, increased stability in the presence of nuclease, or increased inhibitory activity, and accordingly is more preferable than a natural type.

Herein, a "modified internucleoside linkage" refers to an internucleoside linkage having a substitution or any change from a naturally-occurring internucleoside linkage (in other words, phosphodiester linkage). A modified internucleoside linkage encompasses an internucleoside linkage comprising a phosphorus atom and an internucleoside linkage comprising no phosphorus atom. Representative examples of phosphorus-containing internucleoside linkages include, but are not limited to, a phosphodiester linkage, phosphorothioate linkage, phosphorodithioate linkage, phosphotriester linkage, methylphosphonate linkage, methylthiophosphonate linkage, boranophosphate linkage, and phosphoramidate linkage. A phosphorothioate linkage refers to an internucleoside linkage resulting from a phosphodiester linkage whose non-bridged oxygen atom is substituted with a sulfur atom. Methods of preparing phosphorus-containing and non-phosphorus-containing linkages are well known. Modified internucleoside linkages are preferably those having a higher nuclease resistance than naturally occurring internucleoside linkages.

Herein, a "modified nucleic acid base" or "modified base" refers to any nucleic acid base other than adenine, cytosine, guanine, thymine, or uracil. An "unmodified nucleic acid base" or "unmodified base" (natural nucleic acid base) refers to adenine (A) and guanine (G) which are purine bases and to thymine (T), cytosine (C), and uracil (U) which are pyrimidine bases. Examples of modified nucleic acid bases include, but are not limited to: 5-methylcytosine, 5-fluorocytosine, 5-bromocytosine, 5-iodocytosine, and N4-methylcytosine; N6-methyladenine and 8-bromoadenine; and N2-methylguanine or 8-bromoguanine.

Herein, a "modified sugar" refers to a sugar having a substitution and/or any change from a natural sugar moiety (in other words, a sugar moiety found in DNA (2'-H) or RNA (2'-OH)). Herein, a nucleic acid strand may optionally comprise one or more modified nucleosides comprising a modified sugar. Such a sugar-modified nucleoside can confer enhanced nuclease stability, an increased binding affinity, or any other useful biological characteristics to a nucleic acid strand. In a specific embodiment, a nucleoside comprises a chemically-modified ribofuranose ring moiety. Examples of chemically-modified ribofuranose rings include, but are not limited to, those resulting from: addition of a substituent (including 5' and 2' substituents); formation of a bicyclic nucleic acid (bridged nucleic acid, or BNA) by bridge-formation of non-geminal ring atoms; substitution of a ribosyl ring oxygen atom with S, N(R), or C(R1)(R2) (R, R1, and R2 independently represent H, $C_1$-$C_{12}$ alkyl, or a protecting group, respectively); and combinations thereof.

Herein, examples of nucleosides having a modified sugar moiety include, but are not limited to, nucleosides comprising a 5'-vinyl, 5'-methyl(R or S), 4'-S, 2'-F (2'-fluoro group), 2'-OCH$_3$ (2'-O-Me group or 2'-O-methyl group), and 2'-O(CH$_2$)$_2$OCH$_3$ substituent. The substituent at the 2' position can be selected from allyl, amino, azido, thio, —O-allyl, —O—$C_1$-$C_{10}$ alkyl, —OCF$_3$, —O(CH$_2$)$_2$SCH$_3$, —O(CH$_2$)$_2$—O—N(Rm)(Rn), and —O—CH$_2$—C(=O)—N(Rm)(Rn), and each of Rm and Rn independently represents H or a substituted or unsubstituted $C_1$-$C_{10}$ alkyl. Herein, a "2'-modified sugar" refers to a furanosyl sugar modified at the 2' position.

As used herein, a "bicyclic nucleoside" refers to a modified nucleoside comprising a bicyclic sugar moiety. In general, a nucleic acid comprising a bicyclic sugar moiety is referred to as a bridged nucleic acid (BNA). Herein, a nucleoside comprising a bicyclic sugar moiety may be referred to as a "bridged nucleoside".

A bicyclic sugar may be a sugar in which the 2' position carbon atom and 4' position carbon atom are bridged by two or more atoms. Examples of bicyclic sugars are known to a person skilled in the art. One subgroup of a nucleic acid comprising a bicyclic sugar (BNA) can be described as having a 2' position carbon atom and 4' position carbon atom that are bridged by 4'-(CH$_2$)$_p$—O-2', 4'-(CH$_2$)—CH$_2$-2', 4'-(CH$_2$)$_p$—S-2', 4'-(CH$_2$)$_p$—OCO-2', or 4'-(CH$_2$)$_n$—N(R$_3$)—O—(CH$_2$)$_m$-2' [wherein p, m, and n represent an integer of 1 to 4, an integer of 0 to 2, and an integer of 1 to 3 respectively; R$_3$ represents a hydrogen atom, alkyl group, alkenyl group, cycloalkyl group, aryl group, aralkyl group, acyl group, sulfonyl group, and unit substituent (fluorescently or chemiluminescently labeled molecule, functional group having nucleic acid cleaving activity, intracellular or intranuclear localization signal peptide, or the like)]. Furthermore, regarding BNA according to a specific embodiment, in the OR$_2$ substituent at the 3' position carbon atom and the OR$_1$ substituent at the 5' position carbon atom, R$_1$ and R$_2$ are typically hydrogen atoms and may be the same or different, and in addition, may be a protecting group for a hydroxyl group for nucleic acid synthesis, alkyl group, alkenyl group, cycloalkyl group, aryl group, aralkyl group, acyl group, sulfonyl group, silyl group, phosphate group, phosphate group protected by a protecting group for nucleic acid synthesis, or —P(R$_4$)R$_5$ [wherein R$_4$ and R$_5$ are the same as or different from each other, and each represent a hydroxyl group, hydroxyl group protected by a protecting group for nucleic acid synthesis, mercapto group, mercapto group protected by a protecting group for nucleic acid synthesis, amino group, $C_1$-$C_5$ alkoxy group, $C_1$-$C_5$ alkylthio group, $C_1$-$C_6$ cyanoalkoxy group, or amino group substituted with a $C_1$-$C_5$ alkyl group]. Non-limiting examples of such BNAs include: methyleneoxy (4'-CH$_2$—O-2') BNA (LNA (Locked Nucleic Acid®, also known as 2',4'-BNA), for example, α-L-methyleneoxy (4'-CH$_2$—O-2') BNA or β-D-methyleneoxy (4'-CH$_2$—O-2') BNA; ethyleneoxy (4'-(CH$_2$)$_2$—O-2') BNA (also known as ENA); β-D-thio(4'-CH$_2$—S-2') BNA; aminooxy(4'-CH$_2$—O—N(R$_3$)-2') BNA; oxyamino(4'-CH$_2$—N(R$_3$)—O-2') BNA (also known as 2',4'-BNA$^{NC}$); 2',4'-BNA$^{coc}$; 3'-amino-2',4'-BNA; 5'-methyl BNA; (4'-CH(CH$_3$)—O-2') BNA (also known as cEt BNA); (4'-CH(CH$_2$OCH$_3$)—O-2') BNA (also known as cMOE BNA); amide BNA (4'-C(O)—N(R)-2') BNA (R=H, Me) (also known as AmNA); and other BNAs known to a person skilled in the art.

Herein, a bicyclic nucleoside having a methyleneoxy(4'-CH$_2$—O-2') bridge may be referred to as an LNA nucleoside.

Methods of preparing a modified sugar are well known to a person skilled in the art. In a nucleotide having a modified sugar moiety, a nucleic acid base moiety (natural one, modified one, or a combination thereof) may be maintained for hybridization with a suitable nucleic acid target.

Figure 4:
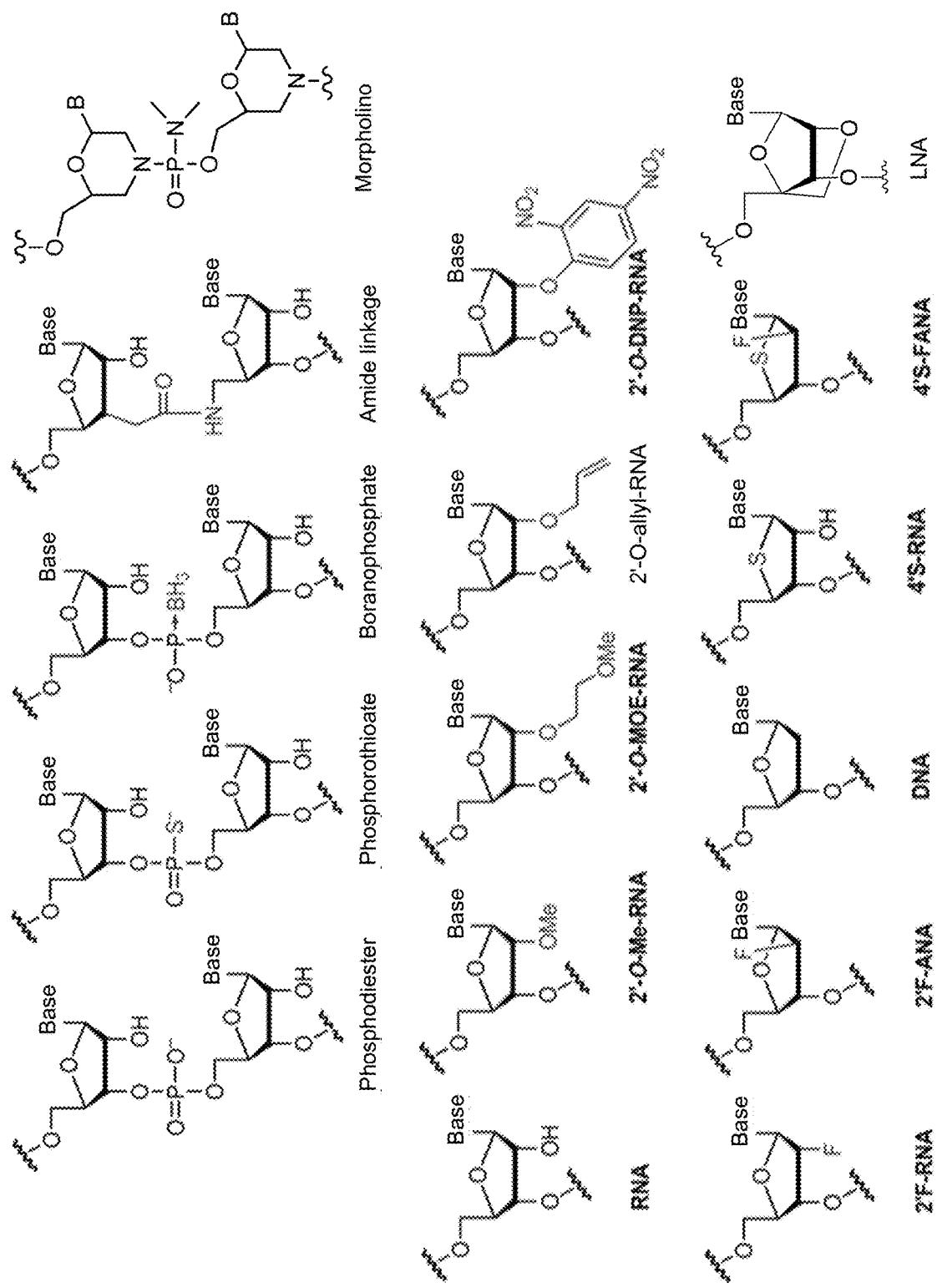
FIG. 4 shows the structures of various natural or unnatural nucleotides.

Herein, a "nucleoside mimic" comprises, at one or more positions in an oligomer compound, a sugar, or a sugar and a base, and optionally a structure used to substitute a linkage. An "oligomer compound" refers to a polymer of linked monomer subunits capable of hybridizing with at least a region of a nucleic acid molecule. Examples of nucleoside mimics include morpholino, cyclohexenyl, cyclohexyl, tetrahydropyranyl, bicyclic, or tricyclic sugar mimics, for example, nucleoside mimics having a non-furanose sugar unit. A "nucleotide mimic" comprises, at one or more positions in an oligomer compound, a nucleoside and a structure used to substitute a linkage. Examples of nucleotide mimics include peptide nucleic acids or morpholino nucleic acids (morpholinos linked by —N(H)—C(=O)—O— or another non-phosphodiester linkage). A peptide nucleic acid (PNA) is a nucleotide mimic having a main-chain to which N-(2-aminoethyl)glycine instead of a sugar is linked by an amide bond. An example of the structure of a morpholino nucleic acid is shown in FIG. 4. A "mimic" refers to a group that substitutes a sugar, nucleic acid base, and/or internucleoside linkage. In general, a mimic is used instead of a sugar or a combination of a sugar and an internucleoside linkage, and a nucleic acid base is maintained for hybridization with a selected target.

In general, modification can be carried out so that nucleotides in the same strand can independently be modified differently. To provide resistance to enzymic cleavage, the same nucleotide can have a modified internucleoside linkage (for example, a phosphorothioate linkage) and further have a modified sugar (for example, a 2'-O-methyl modified sugar or a bicyclic sugar). The same nucleotide can also have a modified nucleic acid base (for example, 5-methylcytosine) and further have a modified sugar (for example, a 2'-O-methyl modified sugar or a bicyclic sugar).

The number, kind, and position of unnatural nucleotides in a nucleic acid strand can have an impact on an antisense effect and the like provided by the nucleic acid complex according to the present invention. The selection of a modification can vary depending on the sequence of a target gene and the like, but a person skilled in the art can determine a suitable embodiment by reference to the explanation in documents related to an antisense method (for example, WO2007/143315, WO2008/043753, and WO 2008/049085). Furthermore, in a case where an antisense effect of a nucleic acid complex obtained after modification is measured, and where a measured value thus obtained is not significantly lower than a measured value of a nucleic acid complex existing before modification (for example, in a case where a measured value obtained after modification is 70% or more, 80% or more, or 90% or more of a measured value of a nucleic acid complex existing before modification), a related modification can be evaluated.

Measurement of an antisense effect can be carried out by introducing a test nucleic acid compound into a cell or a subject (for example, a mouse), or the like, and then suitably using a known technique such as Northern blotting, quantitative PCR, and Western blotting to thereby measure the expression level of a target gene or the level of a target transcription product in the cell (for example, the level of mRNA, the level of RNA such as microRNA, the level of cDNA, the level of protein, and the like) in which the expression of the target gene or target transcription product is suppressed by the antisense effect provided by the test candidate nucleic acid complex, for example, as described in Examples below. The measurement of an antisense effect may be performed by measuring the expression level of a target gene or the level of a target transcription product in a target organ (for example, liver or brain) of a subject.

In cases where the measured expression level of a target gene or the measured level of a target transcription product is reduced by at least 20%, at least 25%, at least 30%, at least 40%, or at least 50% as compared to a negative control (for example, a vehicle-administration or a no-treatment), it is shown that the test nucleic acid compound can produce an antisense effect. In an embodiment, the nucleic acid complex according to the present invention can have a higher (for example, two or more times higher) antisense effect than that provided by the first nucleic acid strand alone.

The ability of delivery of a nucleic acid into a living body can be determined by administering a test nucleic acid compound to a subject (for example, a mouse) and using a known technique appropriately, such as Northern blotting or quantitative PCR, to measure the amount (concentration) of the test candidate nucleic acid complex in the living body (for example, a target organ such as liver or brain), for example, several days (for example, 2 to 5 days) after the administration. In an embodiment, a nucleic acid complex according to the present invention has a higher ability of delivery into a living body than the first nucleic acid strand alone. The amount (concentration) of the administered nucleic acid complex in the living body can be increased by, for example, at least 20%, at least 30%, at least 40%, at least 50%, or at least 60% as compared to the administration of the first nucleic acid strand alone.

The internucleoside linkages in the first nucleic acid strand may be natural internucleoside linkages and/or modified internucleoside linkages. In an embodiment, at least 70%, at least 80%, at least 90%, or 100% of the internucleoside linkages in the first nucleic acid strand may be modified internucleoside linkages. The modified internucleoside linkages may be phosphorothioate linkages.

The nucleosides in the first nucleic acid strand may be natural nucleosides (deoxyribonucleosides, ribonucleosides, or both) and/or unnatural nucleosides.

An embodiment of a nucleoside composition of the first nucleic acid strand is a gapmer(s). Herein, a "gapmer" refers to a nucleic acid strand consisting of a central region (DNA gap region) comprising at least four consecutive deoxyribonucleosides and regions (a 5' wing region and a 3' wing region) comprising unnatural nucleosides located at the 5' terminal side and 3' terminal side of the central region. A gapmer in which the unnatural nucleosides are bridged nucleosides is referred to as a BNA/DNA gapmer. The length of the 5' wing region and that of the 3' wing region may independently be, usually, 1 to 10 bases in length, 1 to 7 bases in length, or 2 to 5 bases in length. The 5' wing region and 3' wing region have only to comprise at least one unnatural nucleoside, and may further comprise a natural nucleoside. The first nucleic acid strand may be a BNA/DNA gapmer comprising a 5' wing region comprising two or three bridged nucleosides, a 3' wing region comprising two or three bridged nucleosides, and a DNA gap region therebetween. The bridged nucleoside may further comprise a modified nucleic acid base (for example, 5-methylcytosine). The gapmer may be an LNA/DNA gapmer in which the bridged nucleoside is an LNA nucleoside.

Another embodiment of a nucleoside composition of the first nucleic acid strand is a mixmer(s). As used herein, a "mixmer" refers to a nucleic acid strand that comprises alternating segments of natural nucleosides (deoxyribonucleoside and/or ribonucleoside) and unnatural nucleosides of periodic or random lengths and that does not have four or more consecutive deoxyribonucleosides nor four or more consecutive ribonucleosides. A mixmer in which the unnatural nucleoside is a bridged nucleoside and in which the natural nucleoside is a deoxyribonucleoside is referred to as a BNA/DNA mixmer. A mixmer in which the unnatural nucleoside is a bridged nucleoside and in which the natural nucleoside is a ribonucleoside is referred to as a BNA/RNA mixmer. A mixmer does not necessarily need to be limited so as to comprise only two kinds of nucleosides. A mixmer can comprise any number of kinds of nucleosides whether the nucleoside is a natural or modified nucleoside or whether it is a nucleoside mimic. For example, a mixmer may have one or two consecutive deoxyribonucleosides separated by a bridged nucleoside (for example, an LNA nucleoside).

The bridged nucleoside may further comprise a modified nucleic acid base (for example, 5-methylcytosine).

The first nucleic acid strand may entirely or partially comprise nucleoside mimics or nucleotide mimics. The nucleotide mimics may be peptide nucleic acids and/or morpholino nucleic acids. The first nucleic acid strand may comprise at least one modified nucleoside. The modified nucleoside may comprise a 2'-modified sugar. The 2'-modified sugar may be a 2'-O-methyl group-containing sugar.

An internucleoside linkage in the second nucleic acid strand may be a natural internucleoside linkage and/or a modified internucleoside linkage.

In an embodiment, at least one (for example, at least two or at least three) internucleoside linkage from the free end of an overhang region in the second nucleic acid strand may be a modified internucleoside linkage. Herein, the "free end of an overhang region" refers to the end of an overhang region which is not connected to the complementary region. For example, in an embodiment as shown in FIG. 1a where an overhang region is located on the 5' terminal side of a complementary region, "the free end of an overhang region" refers to the 5' end of the second nucleic acid strand. In an embodiment as shown in FIG. 1b where an overhang region is located on the 3' terminal side of a complementary region, "the free end of an overhang region" refers to the 3' end of the second nucleic acid strand. In an embodiment as shown in FIG. 1c where overhang regions are located on both the 5' terminal and 3' terminal sides of a complementary region, "the free ends of an overhang region" refers to both ends of the second nucleic acid strand (the 5' end and 3' end). For example, the two internucleoside linkages from the free end of an overhang region in the second nucleic acid strand refers to the internucleoside linkage closest to the free end of an overhang region in the second nucleic acid strand and an internucleoside linkage adjacent thereto in the direction opposite to the free end. Such a modified internucleoside linkage in the terminus is preferred because it can prevent undesirable degradation of the overhang region. The modified internucleoside linkage may be a phosphorothioate linkage.

In an embodiment, at least 50%, at least 60%, at least 70%, at least 75%, at least 80%, at least 85%, at least 90%, or at least 95% (for example, at least 96%, at least 97%, at least 98%, or at least 99%), or preferably 100% of the internucleoside linkages in an overhang region in the second nucleic acid strand may be modified internucleoside linkages. The internucleoside linkages in an overhang region in the second nucleic acid strand refers to linkages between nucleosides that constitute the overhang region, and does not comprise the internucleoside linkage between the overhang region and the complementary region in the second nucleic acid strand. For example, in cases where the overhang region consists of 10 nucleosides, the number of internucleoside linkages in the region is nine. Nevertheless, the internucleoside linkage between the overhang region and the complementary region may be a modified internucleoside linkage or a natural internucleoside linkage. The modified internucleoside linkage may be a phosphorothioate linkage.

In an embodiment, at least one (for example, at least two or at least three) internucleoside linkage from the free end of the complementary region in the second nucleic acid strand may be a modified internucleoside linkage. The "free end of the complementary region" refers to the end of the complementary region which is not connected to an overhang region. For example, in an embodiment as shown in FIG. 1a where an overhang region is located on the 5' terminal side of a complementary region, the "free end of the complementary region" refers to the 3' end of the second nucleic acid strand. In an embodiment as shown in FIG. 1b where an overhang region is located on the 3' terminal side of a complementary region, the "free end of the complementary region" refers to the 5' end of the second nucleic acid strand. In an embodiment as shown in FIG. 1c where overhang regions are located on both the 5' terminal and 3' terminal sides of a complementary region, the "free end of the complementary region" does not exist. The modified internucleoside linkage may be a phosphorothioate linkage.

In a preferred embodiment, all internucleoside linkages in an overhang region in the second nucleic acid strand are modified internucleoside linkages and at least two internucleoside linkages from the free end of the complementary region are modified internucleoside linkages. All internucleoside linkages in the second nucleic acid strand may be modified internucleoside linkages. The modified internucleoside linkages may be phosphorothioate linkages.

Nucleosides in the second nucleic acid strand may be natural nucleosides (deoxyribonucleosides, ribonucleosides, or both) and/or unnatural nucleosides.

An overhang region in the second nucleic acid strand can comprise natural nucleosides (deoxyribonucleosides, ribonucleosides, or both) and/or unnatural nucleosides. In an embodiment, the nucleosides in an overhang region may comprise a deoxyribonucleoside or may consist of deoxyribonucleosides. In another embodiment, at least one (for example, at least two or at least three, specifically one to three) nucleoside from the free end of an overhang region may be a modified nucleoside. Furthermore, at least one (for example, at least two or at least three, specifically one to three) nucleoside from the connected end of an overhang region may be a modified nucleoside. Herein, the "connected end of an overhang region" refers to the end of the overhang region which is connected to the complementary region. The modified nucleoside may comprise a modified sugar and/or a modified nucleic acid base. The modified sugar may be a bicyclic sugar (for example, a sugar containing a 4'-CH$_2$—O-2' group). The modified nucleic acid base may be a 5-methylcytosine. In an embodiment, at least two nucleosides from the free end of an overhang region can be modified nucleosides (for example, nucleosides containing a bicyclic sugar, such as a sugar containing a 4'-CH$_2$—O-2' group). In cases where an overhang region comprises a bicyclic sugar(s), the strand length of the overhang region can be, for example, 9 to 12 bases. In an addition, in an embodiment, nucleosides in an overhang region can be those comprising no bicyclic sugar. In another embodiment, nucleosides in an overhang region can consist of natural deoxyribonucleosides and/or ribonucleosides and does not comprise a modified nucleoside. Use of natural deoxyribonucleosides and/or ribonucleosides can be advantageous in terms of synthesis cost. Additionally, use of natural deoxyribonucleosides and/or ribonucleosides can also be advantageous in avoiding hybridization to undesirable transcription products. In cases where an overhang region does not comprise a bicyclic sugar, the strand length of the overhang region can be, for example, 9 to 17 bases.

The complementary region in the second nucleic acid strand can comprise natural nucleosides (deoxyribonucleosides, ribonucleosides, or both) and/or unnatural nucleosides. In an embodiment, the complementary region in the second nucleic acid strand can comprise at least 2, at least 3, at least 4, or at least 5 consecutive ribonucleosides. Such consecutive ribonucleosides can form a duplex with a DNA gap region when the first nucleic acid strand is a gapmer. The duplex is recognized by RNase H and can promote cleavage of the second nucleic acid strand by RNase H. The consecutive ribonucleosides may be linked through phosphodiester linkages. In another embodiment, the complementary region in the second nucleic acid strand may not comprise at least two consecutive ribonucleosides. In a preferred embodiment, at least one (for example, at least two or at least three) nucleoside from the free end of the complementary region is a modified nucleoside. The modified nucleoside may comprise a modified sugar and/or a modified nucleic acid base. The modified sugar may be a 2'-modified sugar (for example, a 2'-O-methyl group-containing sugar). The modified nucleic acid base may be a 5-methylcytosine. Specifically, one to three nucleosides from the free end of the complementary region may be modified nucleosides (for example, nucleosides containing a 2'-modified sugar, such as a 2'-O-methyl group-containing sugar), and the other nucleosides in the complementary region may be natural nucleosides (deoxyribonucleosides, ribonucleosides, or both). In an embodiment, one to three nucleosides from the free end of the complementary region in the second nucleic acid strand may be modified nucleosides (for example, nucleosides containing a 2'-modified sugar, such as a 2'-O-methyl group-containing sugar) and the other nucleosides in the complementary region may be deoxyribonucleosides. In another embodiment, at least 50%, at least 60%, at least 70%, at least 80%, at least 90%, or at least 95% of the nucleosides in the complementary region in the second nucleic acid strand may be natural nucleosides.

The second nucleic acid strand may comprise any combination of the above-described modified internucleoside linkages and modified nucleosides.

Figure 2:
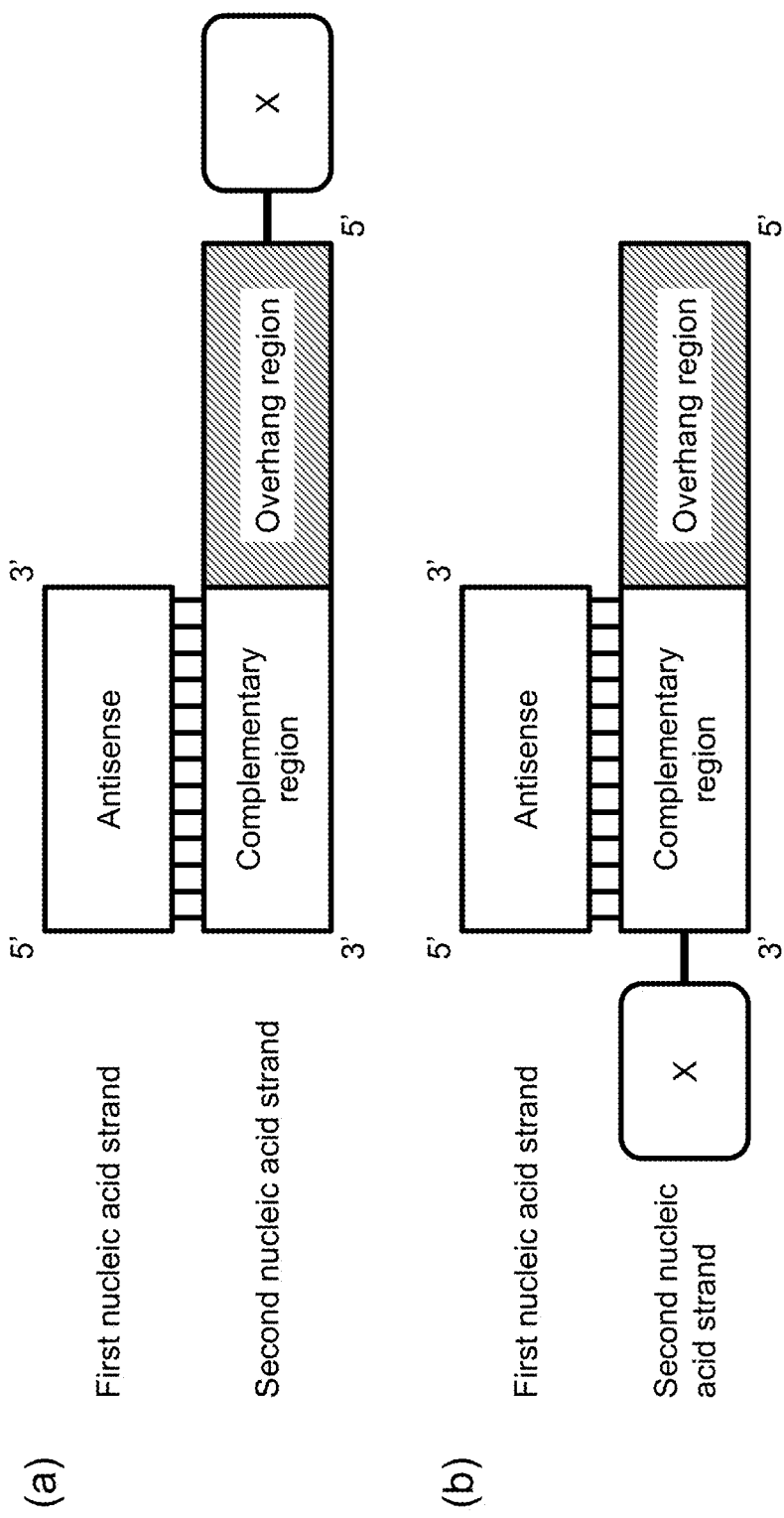
FIG. 2 shows a schematic diagram showing an example of some embodiments of a nucleic acid complex containing a functional moiety ("X").

In an embodiment, the second nucleic acid strand can comprise at least one functional moiety linked to a polynucleotide. The functional moiety "X" may be linked to the 5' end (FIG. 2a) or the 3' end (FIG. 2b) of the second nucleic acid strand. Alternatively, the functional moiety may be linked to a nucleotide in the interior part of the polynucleotide. In other embodiments, the second nucleic acid strand comprises two or more functional moieties, which may be linked to the polynucleotide at multiple positions and/or to the polynucleotide at one position as a group.

The linkage between the second nucleic acid strand and the functional moiety may be a direct linkage or an indirect linkage mediated by another material. However, in a particular embodiment, preferably a functional moiety is directly linked to the second nucleic acid strand through, for example, covalent bonding, ionic bonding, and/or hydrogen bonding, more preferably through covalent bonding considering that more stable linkages can be obtained. A functional moiety may also be linked to the second nucleic acid strand through a cleavable linking group. For example, a functional moiety may be linked through a disulfide bond.

The structure of the "functional moiety" according to a particular embodiment is not limited to a particular one as long as the functional moiety confers a desired function to a nucleic acid complex and/or a strand to which the functional moiety is linked. Examples of desired functions include a labeling function, a purification function, and a delivery function. Examples of a moiety giving a labeling function include a compound such as a fluorescent protein and a luciferase. Examples of moieties which give a purification function include a compound such as biotin, avidin, His-tag peptide, GST-tag peptide, and FLAG-tag peptide.

In some embodiments, a functional moiety serves to enhance transport to cells or cell nuclei. For example, particular peptide tags are demonstrated to enhance cellular uptake of oligonucleotides, when conjugated to the oligonucleotides. Examples of such peptide tags include the arginine-rich peptide P007 and B peptides disclosed in HaiFang Yin et al., Human Molecular Genetics, Vol. 17 (24), 3909-3918 (2008) and references cited therein. Conjugation of a moiety such as m3G-CAP (see Pedro M. D. Moreno et al., Nucleic Acids Res., Vol. 37, 1925-1935 (2009)) to an oligonucleotide can enhance nuclear transport.

Furthermore, the second nucleic acid strand is preferably linked with, as a functional moiety, a molecule having an activity to deliver a nucleic acid complex according to some embodiments of the present invention to a "target site" in the body, in order to deliver a nucleic acid complex (or the first nucleic acid strand) according to the present invention to a target site or a target region in the body with high specificity and high efficiency and thereby very effectively inhibit the expression of a target transcription product from a related nucleic acid (for example, a target gene).

A moiety having a "targeted delivery function" may be, for example, a lipid, to be capable of delivering a nucleic acid complex according to a particular embodiment of the present invention to, for example, the liver with high specificity and high efficiency. Examples of such lipids include lipids such as cholesterol and fatty acids (for example, vitamin E (tocopherol, tocotrienol), vitamin A, and vitamin D); lipophilic vitamins such as vitamin K (for example, acylcarnitine); intermediate metabolites such as acyl-CoA; glycolipids, glycerides, and derivatives or analogs thereof. However, among these, cholesterol and vitamin E (tocopherol and tocotrienol) are used in a particular embodiment, considering that these compounds have higher safety. However, a nucleic acid complex according to a particular embodiment of the present invention may not be linked with a lipid.

Tocopherol can be selected from the group consisting of α-tocopherol, β-tocopherol, γ-tocopherol, and δ-tocopherol. Analogs of tocopherol include various unsaturated analogs of tocopherol, for example, α-tocotrienol, β-tocotrienol, γ-tocotrienol, and δ-tocotrienol. Preferably, the tocopherol is α-tocopherol.

Analogs of cholesterol refers to various metabolites and analogs of cholesterol, which are alcohols having a sterol backbone, and include, but are not limited to, cholestanol, lanosterol, cerebrosterol, dehydrocholesterol, and coprostanol and the like.

Furthermore, examples of the "functional moiety" according to a particular embodiment include sugars (for example, glucose and sucrose), to be capable of delivering a nucleic acid complex according to a particular embodiment of the present invention to the brain with high specificity and high efficiency.

Additionally, examples of the "functional moiety" according to a particular embodiment include peptides or proteins (for example, receptor ligands, and antibodies and/or fragments thereof), to be capable of binding to various proteins present on the surface of cells in various organs and thereby deliver the nucleic acid complex according to a particular embodiment of the present invention to various organs with high specificity and high efficiency.

As described above, several suitable illustrative embodiments of the nucleic acid complex in some of the embodiments of the present invention have been described, but the nucleic acid complex is not intended to be limited to the above-mentioned illustrative embodiments. Furthermore, a person skilled in the art can produce, by selecting a known method suitably, a first nucleic acid strand and a second nucleic acid strand that constitute a nucleic acid complex according to various embodiments of the present invention. For example, nucleic acids according to some of the embodiments of the present invention can be produced by designing each base sequence of the nucleic acid based on information on the base sequence of a target transcription product (or the base sequence of a target gene in some cases), synthesizing a nucleic acid using a commercially available automated nucleic acid synthesis device (a product of Applied Biosystems, Inc., a product of Beckman Coulter, Inc., or the like), and then purifying the resulting oligonucleotide using a reversed phase column and the like. A nucleic acid produced in this method is mixed in a suitable buffer solution and denatured at about 90° C. to 98° C. for several minutes (for example, five minutes), the nucleic acid is then annealed at about 30° C. to 70° C. for about one to eight hours, and thus, a nucleic acid complex according to some of the embodiments of the present invention can be produced. Preparation of an annealed nucleic acid complex is not limited to such a time and temperature protocol. Conditions suitable to promote annealing of strands are well known in the art. A nucleic acid complex further linked to a functional moiety can be produced by using the kind of nucleic acid that has a functional moiety linked thereto in advance and carrying out the above-mentioned synthesis, purification, and annealing. Many methods for linking a functional moiety to a nucleic acid are well known in the art. Alternatively, a nucleic acid strand according to some of the embodiments can be ordered and obtained from a manufacturer (for example, GeneDesign Inc.), in which case the base sequence and the site and type of modification should be specified.

The inventors indicate in the following Examples that the binding of the nucleic acid complex according to some embodiments with serum proteins is altered as compared to that of conventional single-stranded antisense oligonucleotides. The nucleic acid complex according to some embodiments can be efficiently delivered into the living body, at least partially resulting from such altered binding with serum proteins, to inhibit the expression of a target gene or the level a target transcription product through the antisense effect. Thus, the nucleic acid complex according to some embodiments may be a nucleic acid complex for use in inhibiting the expression of a target gene or the level of a target transcription product.

<Compositions>

Compositions comprising a nucleic acid complex as described above as an active ingredient to inhibit the expression of a target gene or the level of a target transcription product through an antisense effect are also provided. Herein, the phrases "the level of a target transcription product" and "the expression level of a target transcription product" are interchangeably used.

The compositions comprising the nucleic acid complex according to some embodiments of the present invention can be formulated using a known pharmaceutical manufacturing method. For example, the present composition can be used orally or parenterally in the form of capsules, tablets, pills, liquid, powder, granules, microgranules, film coated formulations, pellets, troches, sublingual formulations, peptizers, buccals, pastes, syrups, suspensions, elixirs, emulsions, coating agents, ointments, plasters, cataplasms, transdermal formulations, lotions, inhalants, aerosols, eyedrops, injection solutions, and suppositories.

With regard to formulating these formulations, pharmacologically acceptable carriers or carriers acceptable as food and beverage can be suitably incorporated, specific examples thereof including sterile water, physiological saline, plant oil, solvents, bases, emulsifying agents, suspending agents, surfactants, pH adjustors, stabilizers, flavoring agents, perfumes, excipients, vehicles, antiseptics, binders, diluents, isotonizing agents, sedatives, expanders, disintegrators, buffers, coating agents, lubricants, coloring agents, sweetners, thickeners, flavoring substances, dissolving auxiliaries, and other additives.

Preferable forms of administration of the composition according to some embodiments of the present invention are not limited, and examples thereof include oral administration or parenteral administration, more specifically, intravenous administration, intraventricular administration, intrathecal administration, subcutaneous administration, intraarterial administration, intraperitoneal administration, intradermal administration, tracheal/bronchial administration, rectal administration, intraocular administration, and intramuscular administration, and administration by transfusion. Administration may be carried out by intramuscular injection administration, continuous infusion administration, inhalation, skin patch, or implantable type continuous subcutaneous administration. Subcutaneous administration can be advantageous as compared to intravenous administration, in terms of simplicity in administration. Subcutaneous administration is preferred because self-injection by a patient oneself is possible. In an embodiment, a nucleic acid complex used for subcutaneous administration can be a nucleic acid complex not conjugated with a lipid, such as vitamin E (tocopherol, tocotrienol) and cholesterol. Without wishing to be bound by a particular theory, in cases where a ligand is used, it is considered that the ligand should have a suitable lipid solubility to move through the subcutaneous fat into the blood stream. Thus, for example, a cholesterol ligand is preferably used.

The composition according to some embodiments of the present invention can be used for animals, including humans, as subjects. However, animals other than humans are not limited to particular animals, and various animals such as farm animals, poultry, pet animals, and laboratory animals may be subjects in some embodiments.

In cases where a composition according to some embodiments of the present invention is administered or ingested, the administered or ingested amount of the composition can be selected depending on factors such as the age, weight, symptoms, and health conditions of a subject, and the type of the composition (whether it is a pharmaceutical product, a food, a beverage, or the like). However, the ingested effective amount of a composition according to a particular embodiment of the present invention can be, for example, 0.0000001 mg/kg/day to 1000000 mg/kg/day, 0.00001 mg/kg/day to 10000 mg/kg/day, or 0.001 mg/kg/day to 100 mg/kg/day of the nucleic acid complex.

The present invention also relates to a pharmaceutical composition for treatment or prevention of a disease associated with, for example, an abnormality in a gene (for example, a mutation of a gene, a genetic deletion, a genetic insertion, a gene conversion, or an abnormality in the number of repeated sequences), or a disease associated with, for example, abnormal expression (increased or decreased expression, or an abnormality in a genetic variant) of a target gene (a degenerative disease, a blood vessel disorder, an immunological disease, an endocrine metabolic disease, a tumor, an infectious disease and the like).

In an embodiment, the pharmaceutical composition may be a pharmaceutical composition for intraventricular (intrathecal) administration to treat or prevent a central nervous system disease and a disease that affects intrathecal nerve roots or dorsal root ganglions. As disclosed in Examples of the present application, the present inventors unexpectedly found that intraventricular (intrathecal) administration of a nucleic acid complex according to the present invention can produce an effect superior to conventionally known double-stranded agents. In an embodiment, the nucleic acid complex used for the intraventricular (intrathecal) administration may be a nucleic acid complex not conjugated with a lipid, such as vitamin E (tocopherol, tocotrienol) and cholesterol.

The disease to be treated may be a neurological disease associated with an abnormality of a gene. The nervous system is divided into the central nervous system and the peripheral nervous system. Thus, the disease to be treated may be a central nervous system disease. The central nervous system consists of the brain and spinal cord. The brain includes the cerebrum (the cerebral cortex, cerebral white matter, and basal ganglion), the diencephalon (the thalamus, and subthalamic nucleus), the cerebellum (the cerebellar cortex, and cerebellar nucleus) and the brainstem (the midbrain, substantia nigra, pons, and medulla oblongata). The spinal cord includes the cervical, thoracic, and lumbar spinal cords, and sacral and coccygeal cords. The central nervous system as used herein may refer to any of these regions and can be, particularly, the cerebral cortex (the frontal lobe, temporal lobe, parietal lobe, and occipital lobe), cerebellum, striatum, globus pallidus, claustrum, hippocampus, parahippocampal gyrus, brainstem, cervical spinal cord, thoracic spinal cord, or lumbar spinal cord. The peripheral nervous system consists of cranial and spinal nerves. Thus, a disease to be treated may be a disease that affects intrathecal nerve roots, the cauda equina, or dorsal root ganglions (for example, carcinomatous meningitis).

The central nervous system disease is not limited to a particular disease, and examples of the central nervous system disease include brain tumors, Alzheimer's disease, Parkinson's disease, amyotrophic lateral sclerosis, multiple sclerosis, and Huntington's disease. In the treatment of Alzheimer's disease, for example, drug delivery into the hippocampus and/or the parietal lobe can be effective. In the treatment of frontotemporal dementia (FTD) (frontotemporal lobar degeneration (FTLD), semantic dementia (SD), progressive nonfluent aphasia (PNFA)) and Pick's disease, drug delivery into the frontal lobe, the temporal lobe and/or the substantia nigra can be effective. In the treatment of Lewy body dementia (DLB) and Parkinson's disease dementia, drug delivery into the occipital lobe, the substantia nigra and/or the striatum can be effective. In the treatment of Parkinson's disease, drug delivery into the substantia nigra and/or the striatum can be effective. In the treatment of corticobasal degeneration (CBD), drug delivery into the frontal lobe, the parietal lobe, the basal ganglion and/or the substantia nigra can be effective. In the treatment of progressive supranuclear palsy (PSP), drug delivery into the frontal lobe, the basal ganglion and/or the substantia nigra can be effective. In the treatment of amyotrophic lateral sclerosis and spinal muscular atrophy, drug delivery into the frontal lobe, the parietal lobe, the substantia nigra, the basal ganglion and/or the spinal cord can be effective. In the treatment of spinocerebellar degeneration (SCD) SCA1 to SCA34, drug delivery into the brainstem and/or the cerebellum can be effective. In the treatment of dentatorubural-pallidoluysian atrophy (DRPLA), drug delivery into the brainstem, the basal ganglion and/or the cerebellum can be effective. In the treatment of spinal and bulbar muscular atrophy (SBMA), drug delivery into skeletal muscles, the brainstem and/or the spinal cord can be effective. In the treatment of Friedreich's ataxia (FA), drug delivery into the brainstem and/or the cerebellum can be effective. In the treatment of Huntington's disease, drug delivery into the striatum, the frontal lobe, the parietal lobe and/or the basal ganglion can be effective. In the treatment of prion diseases (mad cow disease and GSS), drug delivery into the cerebral cortex, the cerebral white matter, the basal ganglion and/or the substantia nigra can be effective. In the treatment of leukoencephalopathy, particularly of progressive multifocal leukoencephalopathy, drug delivery into the cerebral white matter can be effective. In the treatment of encephalitis (viral, bacterial, fungal, and tuberculous encephalitis) and meningitis (viral, bacterial, fungal, and tuberculous meningitis), drug delivery into the entire brain can be effective. In the treatment of metabolic encephalopathy, toxic encephalopathy, and nutritional encephalopathy, drug delivery into the entire brain can be effective. In the treatment of cerebral infarction, cerebral hemorrhage, subarachnoid hemorrhage, moyamoya disease, and anoxic encephalopathy, drug delivery into the entire brain can be effective. In the treatment of diffuse axonal injury, drug delivery into the cerebral white matter can be effective. In the treatment of head trauma, drug delivery into the entire brain can be effective. In the treatment of multiple sclerosis (MS) and neuromyelitis optica (NMO), drug delivery into the cerebral white matter, the cerebral cortex, optic nerves, and/or the spinal cord can be effective. In the treatment of myotonic dystrophy (DM1, DM2), drug delivery into skeletal muscles, the myocardium, the cerebral cortex and/or the cerebral white matter can be effective. In the treatment of hereditary spastic paraplegia (HSP), drug delivery into the parietal lobe and/or the spinal cord can be effective. In the treatment of Fukuyama muscular dystrophy, drug delivery into skeletal muscles, the cerebral cortex and/or the cerebral white matter can be effective. In the treatment of DLB, drug delivery into the frontal lobe and/or the parietal lobe can be effective. In the treatment of multiple system atrophy (MSA), drug delivery into the striatum, the basal ganglion, the cerebellum, the substantia nigra, the frontal lobe and/or the temporal lobe can be effective. In the treatment of Alexander's disease, drug delivery into the cerebral white matter can be effective. In the treatment of CADASIL and CARASIL, drug delivery into the cerebral white matter can be effective.

The disease that affects nerve roots and/or the cauda *equina* is not limited to a particular disease and may include Guillain-Barre syndrome, Fisher syndrome, chronic inflammatory demyelinating polyneuropathy, and cervical spondylotic radiculomyelopathy. Additionally, the neurological diseases that affect dorsal root ganglions may include peripheral neuropathic pain, Sjogren's syndrome, and paraneoplastic syndrome.

Thus, some embodiments of the present invention relate to a composition comprising a nucleic acid complex for the treatment of each disease as described above and to a method of treating each disease as described above, the method comprising administering such a composition. Moreover, some embodiments of the present invention relate to a composition comprising a nucleic acid complex for regulating (for example, reducing) the expression level of a transcription product in each site as described above.

Examples of the central nervous system diseases include, but are not limited to, Huntington's disease, Alzheimer's disease, Parkinson's disease, ALS, and brain tumors.

As disclosed in Examples below, the nucleic acid complex according to some embodiments can be delivered to a part in the body with high efficiency to achieve very effective modification or inhibition of the expression of a target gene or the level of a target transcription product. Examples of the target site in the body to which the nucleic acid complex according to some embodiments is delivered include the liver, brain, kidney, adrenal gland, muscle (for example, skeletal muscle such as femoral muscle), and lung. The compositions according to the present invention can be delivered to a target site in the body to provide an antisense effect to a target gene or a target transcription product at the target site.

Thus, a method of inhibiting the expression of a target gene or the level of a target transcription product by administering a nucleic acid complex or composition according to some embodiments to a subject is provided. Furthermore, a method of treating or preventing a disease related to increase in the expression of a target gene or the level of a target transcription product is also provided, the method comprising administering a nucleic acid complex or composition according to some embodiments to a subject.

EXAMPLES

The present invention is more specifically described by way of Examples below. However, the technical scope of the present invention is not limited to those Examples.

The sequences of oligonucleotides used in the following Examples are summarized in Table 1.

TABLE 1

| Name of oligonucleotide | Sequence | SEQ ID NO | Example |
|---|---|---|---|
| ASO (ApoB) 12mer | 5'-G(L)*C(L)-a-t-t-g-g-t-a-t-T(L)*C(L)*A(L)-3' | 10 | 1-6, 10, 11 14 |
| cRNA (ApoB) 13mer | 5'-U(M)*G(M)*A(M)*AUACCAU*G(M)*C(M)-3' | 11 | 1 |
| overhanging cRNA (ApoB) 26mer | 5'-C(L)*T(L)*a*g*g*t*c*a*t*g*C(L)*G(L)*T(L)UGAAUACCAAU*G(M)*C(M)-3' | 12 | 1, 10, 11 |
| overhanging portion 13mer | 5'-C(L)*T(L)*a*g*g*t*c*a*t*g*C(L)*G(L)*T(L)-3' | 13 | 1 |
| overhanging cRNA-5' (ApoB) 26mer | 5'-C(L)*T(L)*a*g*g*t*c*a*t*g*C(L)*G(L)*T(L)UGAAUACCAAU*G(M)*C(M)-3' | 14 | 2 |
| overhanging cRNA-3' (ApoB) 26mer | 5'-U(M)*G(M)*AAUACCAAUGCC(L)*T(L)*a*g*g*t*c*a**g*C(L)*G(L)*T(L)-3' | 15 | 2 |
| overhanging cDNA (ApoB) 26mer | 5'-C(L)*T(L)*a*g*g*t*c*a*t*g*C(L)*G(L)*T(L)tgaataccaat*G(M)*C(M)-3' | 16 | 2 |
| overhanging cRNA-all 2'Ome 26mer | 5'-C(L)*T(L)*a*g*g*t*c*a*t*g*C(L)*G(L)*T(L)U(M)G(M)A(M)A(M)U(M)A(M)C(M)C(M)A(M)A(M)U)M)*G(M)*C(M)--3' | 17 | 2 |
| over DNA only cRNA (ApoB) 26mer | 5'-c*t*a*g*g*t*c*a*t*g*c*g*tUGAAUACCAAU*G(M)*C(M)-3' | 18 | 3 |
| over DNA/LNA gap cRNA (ApoB) 26mer | 5'-C(L)*T(L)*a*g*g*t*c*a*t*g*C(L)*G(L)UGAAUACCAAU*G(M)*C(M)-3' | 19 | 3 |
| over RNA/LNA gap cDNA (ApoB) 26mer | 5'-C(L)*T(L)*A*G*G*U*C*A*U*G*C(L)*G(L)*T(L)UGAAUACCAAU*G(M)*C(M)-3' | 20 | 3 |
| over cRNA (ApoB) 26mer | 5'-C(L)*T(L)*a*g*g*t*c*a*t*g*C(L)*G(L)*T(L)UGAAUACCAAU*G(M)*C(M)-3' | 21 | 4 |
| over cRNA (ApoB) 26mer PS-10 | 5'-C(L)*T(L)*aggtcatgC(L)G(L)T(L)UGAAUACCAAU*G(M)*C(M)-3' | 22 | 4 |
| over cRNA (ApoB) 26mer PS+11 | 5'-C(L)*T(L)*a*g*g*t*c*a*t*g*C(L)*G(L)*T(L)*U*G*A*A*U*A*C*C*A*A*U*G(M)*C(M)-3' | 23 | 4 |
| over DNA only cRNA (ApoB) 26mer | 5'-c*t*a*g*g*t*c*a*t*g*c*g*tUGAAUACCAAU*G(M)*C(M)-3' | 24 | 5, 14 |
| over DNA only cRNA (ApoB) 24mer | 5'-c*t*a*g*g*t*c*a*t*g*c*UGAAUACCAAU*G(M)*C(M)-3' | 25 | 5 |
| over DNA only cRNA (ApoB) 22mer | 5'-c*t*a*g*g*t*c*a*t*tUGAAUACCAAU*G(M)*C(M)-3' | 26 | 5 |
| over DNA only cRNA (ApoB) 20mer | 5'-c*t*a*g*g*t*cUGAAUACCAAU*G(M)*C(M)-3' | 27 | 5 |

TABLE 1-continued

| Name of oligonucleotide | Sequence | SEQ ID NO | Example |
|---|---|---|---|
| over DNA only cRNA (ApoB) 18mer | 5'-c*t*a*g*gUGAAUACCAAU*G(M)*C(M)-3' | 28 | 5 |
| over DNA only cRNA (ApoB) 15mer | 5'-c*tUGAAUACCAAU*G(M)*C(M)-3' | 29 | 5 |
| over LNA-Gap cRNA (ApoB) 26mer | 5'-C(L)*T(L)*a*g*g*t*c*a*t*g*C(L)*G(L)*T(L)UGAAUACCAAU*G(M)*C(M)-3' | 30 | 6 |
| over LNA-Gap cRNA (ApoB) 24mer | 5'-C(L)*T(L)*a*g*g*t*c*a*C(L)*G(L)*T(L)UGAAUACCAAU*G(M)*C(M)-3' | 31 | 6 |
| ASO (SRB1) 13mer | 5'-C(L)*A(L)*g*t*c*a*t*g*a*c*T(L)*T(L)*C(L)-3' | 32 | 7, 16 |
| over DNA only cRNA (SRB1) 26mer | 5'-c*t*a*g*g*t*c*a*t*g*c*g*tGAAGUCAUGAC*U(M)*G(M)-3' | 33 | 7, 16 |
| over DNA only cRNA (SRB1) 22mer | 5'-c*t*a*g*g*t*c*g*tGAAGUCAUGAC*U(M)*G(M)-3' | 34 | 7 |
| ASO (MALAT1) 16mer | 5'-C(L)*T(L)*A(L)*g*t*t*c*a*c*t*g*a*a*T(L)*G(L)*C(L)-3' | 35 | 8 |
| over cRNA (MALAT1) 29mer | 5'-c*t*a*g*g*t*c*a*t*g*c*g*tGCAUUCAGUGAACU*A(M)*G(M)-3' | 36 | 8 |
| over cRNA (MALAT1) 25mer | 5'-c*t*a*g*g*t*c*g*tGCAUUCAGUGAACU*A(M)*G(M)-3' | 37 | 8 |
| over cRNA (MALAT1) 21mer | 5'-c*t*c*g*tGCAUUCAGUGAACU*A(M)*G(M)-3' | 38 | 8 |
| antimiR-122 | 5'-C(L)*c*A(L)*t*t*G(L)*T(L)*c*a*C(L)*a*C(L)*t*C(L)*C(L)-3' | 39 | 9 |
| over cRNA (antimiR) 30mer | 5'-C(L)*g*C(L)*a*t*T(L)*G(L)*g*t*A(L)*t*T(L)*c*G(L)*C(L)GGAGUGUGACAAU*G(M)*G(M)-3' | 40 | 9 |
| HDO-cRNA (antimiR) | 5'-G(M)*G(M)*A(M)*GUGUGACAA*U(M)*G(M)*G(M))-3' | 41 | 9 |
| HCDO 1st strand (antimiR) | 5'-C(L)*g*C(L)*a*t*T(L)*G(L)*g*t*A(L)*t*T(L)*c*G(L)*C(L)-3' | 42 | 9 |
| HCDO-cRNA (antimiR) | 5'-C(L)*c*A(L)*t*t*G(L)*T(L)*c*a*C(L)*a*C(L)TC(L)*C(L)GCGAAUACCAAUG*C(M)*G(M)-3' | 43 | 9 |
| ASO (BACE1) 13mer | 5'-G(L)*T(L)*a*t*t*g*c*t*g*a*G(L)*G(L)*A(L)-3' | 44 | 12 |
| overhanging cRNA (BACE1) 26mer | 5'-G(L)*T(L)*a*g*g*t*c*a*t*g*C(L)*G(L)*T(L)UCCUCAGCAAU*A(M)*C(M)-3' | 45 | 12 |
| HDO-cRNA | 5'-U(M)*C(M)*C(M)*UCAGCAAU*A(M)*C(M)-3' | 46 | 12 |
| Toc-HDO-cRNA | 5'-Toc-U(M)*C(M)*C(M)*UCAGCAAU*A(M)*C(M)-3' | 47 | 12 |
| ASO (PTEN) 16mer | 5'-A(L)*T(L)*C(L)*a*t*g*g*c*t*g*c*a*g*C(L)*T(L)*T(L)-3' | 48 | 13, 15 |
| HCDO 1st strand (PTEN) | 5'-C(L)*T(L)*a*g*g*t*c*a*t*g*C(L)*G(L)*T(L)-3' | 49 | 13 |
| HECO-cRNA (PTEN) | 5'-A(L)*T(L)*C(L)*a*t*g*g*c*t*g*c*a*g*C(L)*T(L)*T(L)ACGCAUGACCU*A(M)*G(M)-3' | 50 | 13 |
| overhang cRNA (PTEN) | 5'-C(L)*T(L)*a*g*g*t*c*a*t*g*C(L)*G(L)*T(L)AAGCUGCAGCCAUG*A(M)*U(M)-3' | 51 | 13, 15 |

Upper case (L): LNA C(L) represents 5-methlycytosine (LNA)
Lower case letter: DNA
Upper case letter: RNA
Upper case letter (M): 2'-O-Me RNA
*phosphorothioate
Toc: tocophero;

Example 1

The usefulness of a double-stranded nucleic acid agent according to an embodiment was tested by an in vivo experiment. Two double-stranded agents, a heteroduplex oligonucleotide (hereinafter referred to as "HDO") and an overhanging-duplex oligonucleotide (hereinafter referred to as "Overhang") according to an embodiment of the present invention, were evaluated using an antisense oligonucleotide in the form of a conventional single-stranded LNA/DNA gapmer (hereinafter referred to as "ASO") as a control. The efficacy of the overhanging portion alone was also compared.

Figure 5:
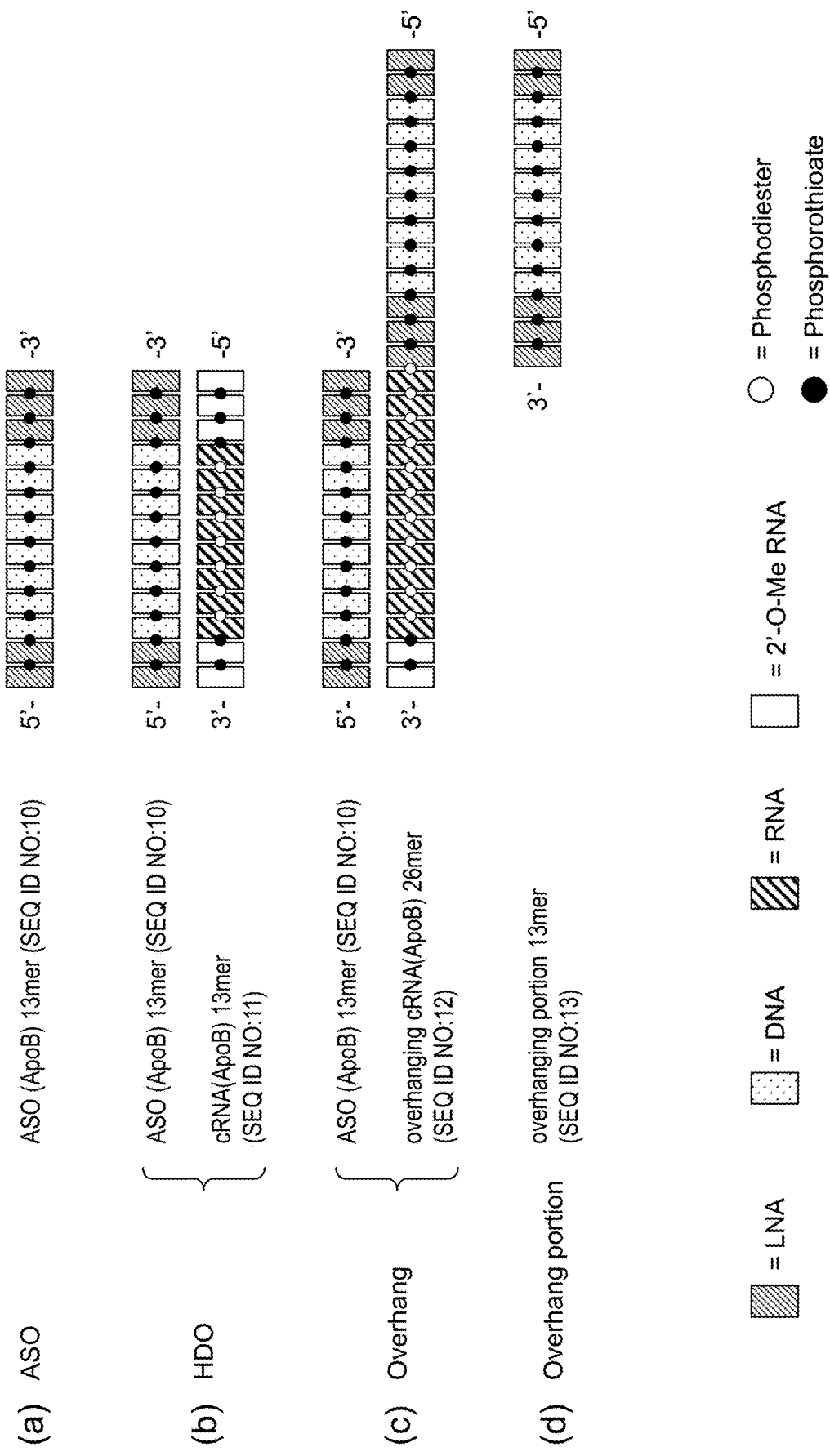
FIG. 5 shows a schematic diagram of the structures of nucleic acids used in Example 1. For each nucleic acid, the name of the nucleic acid, the name of each oligonucleotide, and the structure are shown in this order from left to right.

The single-stranded ASO used as a control was a 13-mer LNA/DNA gapmer complementary to the mouse apolipoprotein B mRNA (SEQ ID NO: 1) from positions 10136 to 10148. The LNA/DNA gapmer contains two and three LNA nucleosides at the 5' and 3' ends, respectively, and in-between eight DNA nucleosides. The two double-stranded agents ("HDO" and "Overhang") each consist of a first strand (the above-described LNA/DNA gapmer) and a second strand (a complementary strand annealing to the first strand) to form a double-stranded structure. The second strand is completely complementary to the first strand in the "HDO," while the second strand has a 13 bases long overhang region located on the 5' terminal side of a region complementary to the first strand in the "Overhang." The sequences, chemical modifications, and structures of the polynucleotides used in Example 1 are shown in Table 1 and FIG. 5.

For the preparation of the above-described double-stranded agents, equimolar amounts of the first strand and each second strand were mixed and the resulting solution was heated at 95° C. for 5 minutes, and then cooled and kept at 37° C. for one hour to anneal the nucleic acid strands for preparing a double-stranded nucleic acid complex. The annealed nucleic acid was stored at 4° C. or on ice. All the oligonucleotides were custom-synthesized by GeneDesign, Inc. (Osaka, Japan).

(In Vivo Experiment)

Four-week-old female ICR mice with a body weight of 20 to 25 g were used. Each nucleic acid agent was injected intravenously at a dose of 0.173 µmol/kg to mice (n=5) via tail vein. Moreover, mice injected with PBS alone (instead of the nucleic acid agents) were prepared as a negative control group. Seventy-two hours after the injection, the mice were perfused with PBS and then dissected to isolate the liver. Subsequently, the Isogen II kit (GeneDesign, Inc.) was used according to the protocol to extract RNA. The Transcriptor Universal cDNA Master, DNase (Roche Diagnostics) was used according to the protocol to synthesize cDNA. Quantitative RT-PCR was performed with TaqMan (Roche Applied Science). The primers used in the quantitative RT-PCR were designed according to various numbers of genes and produced by Thermo Fisher Scientific (former Life Technologies Corp). Amplification conditions (temperature and time) were as follows: 15 seconds at 95° C., and 40 cycles of 30 seconds at 60° C. and 1 second at 72° C. On the basis of the thus-obtained result of the quantitative RT-PCR, the ratio of the expression level of apolipoprotein B (ApoB) to GAPDH (an internal reference gene) was calculated individually. In addition, the results from the respective groups were compared and further evaluated by Bonferroni test.

(Result)

Figure 6:
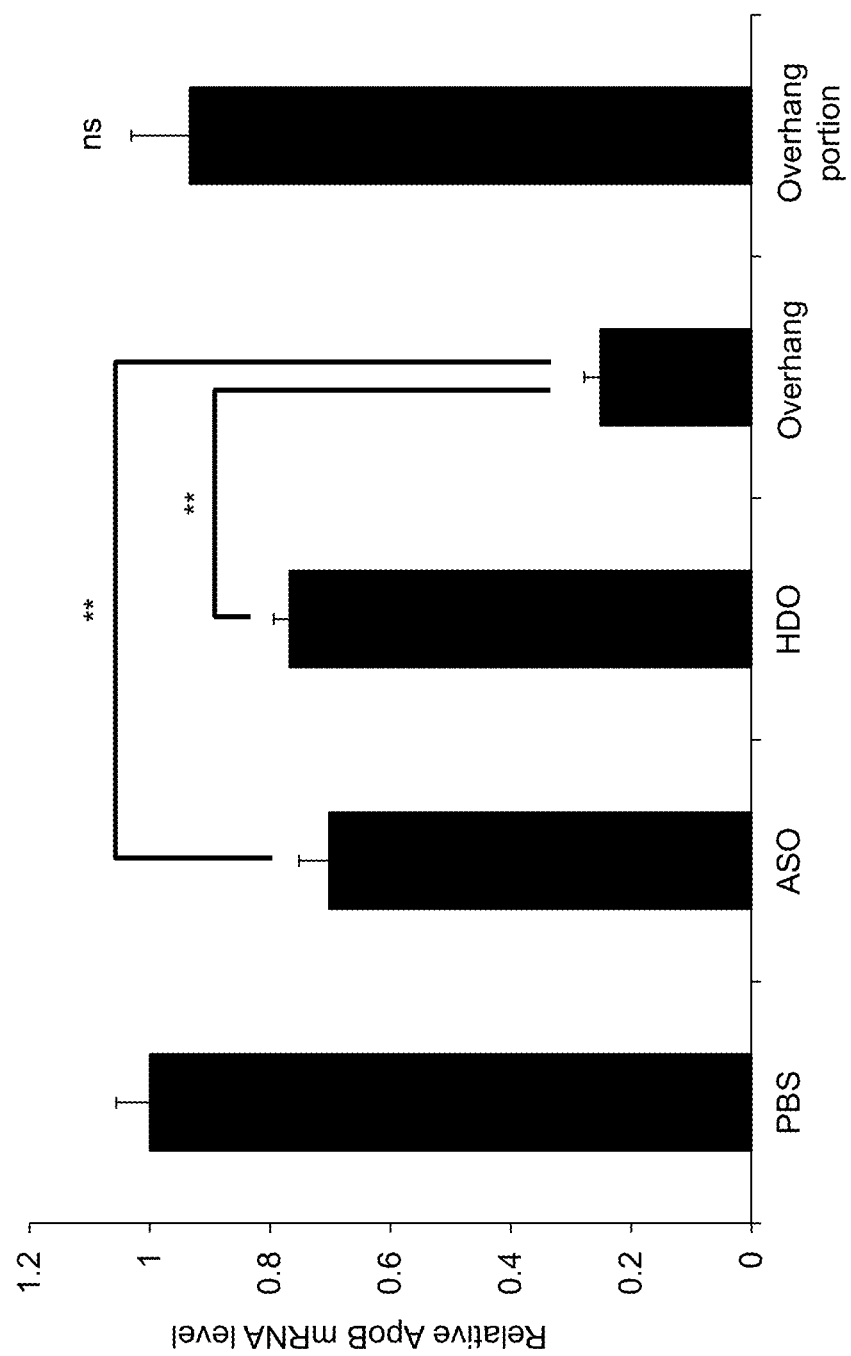
FIG. 6 shows a graph showing the result of an experiment described in Example 1, comparing the inhibitory effects on the expression of a target gene (ApoB) by a nucleic acid complex according to a particular embodiment. The double asterisk (**) indicates $p<0.01$. The sign "ns" indicates no significant difference when compared with the negative control (PBS only).

The result of Example 1 is shown in the graph of FIG. 6. An inhibition of ApoB mRNA expression was indicated in all the groups treated with the three nucleic acid agents, the single-stranded "ASO," "HDO," and "Overhang," as compared to the negative control (PBS alone). However, the inhibition degree obtained by the "Overhang," which is an embodiment of the present invention, was larger than that obtained by the single-stranded ASO or the HDO, and the differences were statistically significant. On the other hand, the expression of ApoB mRNA was not inhibited by the overhanging portion alone. These results indicated that the double-stranded nucleic acid complex formed by annealing an antisense oligonucleotide to a complementary strand having an overhang region is efficiently delivered into the living body and produces an antisense effect.

Example 2

Figure 7:
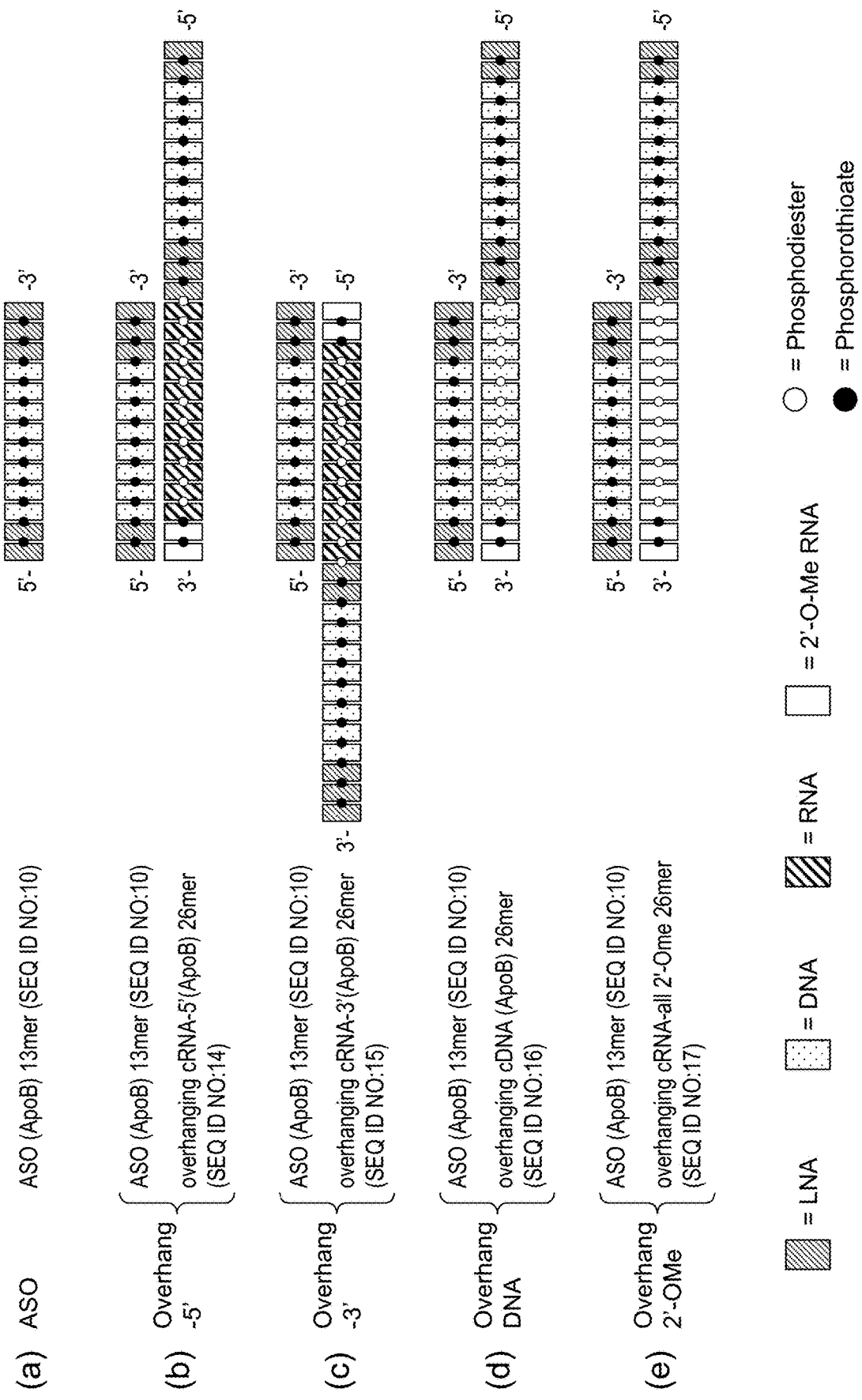
FIG. 7 shows a schematic diagram of the structures of nucleic acids used in Example 2. For each nucleic acid, the name of the nucleic acid, the name of each oligonucleotide, and the structure are shown in this order from left to right.

The usefulness of a double-stranded nucleic acid agent according to an embodiment being different in the protruding side of a second strand or in chemical modifications in the double-stranded portion was tested by an in vivo experiment. The target was ApoB mRNA, as in Example 1. The control (ASO) was also the same single-stranded LNA/DNA gapmer as in Example 1. The LNA/DNA gapmer (first strand) was annealed to a different complementary strand (second strand) to prepare four different double-stranded agents (referred to as "Overhang-5'," "Overhang-3'," "Overhang DNA," and "Overhang 2'-OMe"). The "Overhang-5'" and the "Overhang-3'" have an overhang on the 5' terminal side and the 3' terminal side, respectively. Additionally, a region complementary to the first strand in the second strand of the "Overhang-5'" comprises eleven RNA nucleosides and two 2'-O-Me RNA nucleosides from the 5' end, while RNAs in the "Overhang-5'" are replaced with DNAs in the "Overhang DNA," and RNAs in the "Overhang-5'" are replaced with 2'-O-methyl RNAs in the "Overhang 2'-OMe." The sequences, chemical modifications, and structures of the polynucleotides used in Example 2 are shown in Table 1 and FIG. 7. The double-stranded agents were prepared similarly to Example 1.

(In Vivo Experiment)

Each nucleic acid agent was injected intravenously at a dose of 0.173 µmol/kg to mice (n=4) via tail vein. Mice used and a method of analyzing ApoB mRNA expression are as described in Example 1.

(Result)

Figure 8:
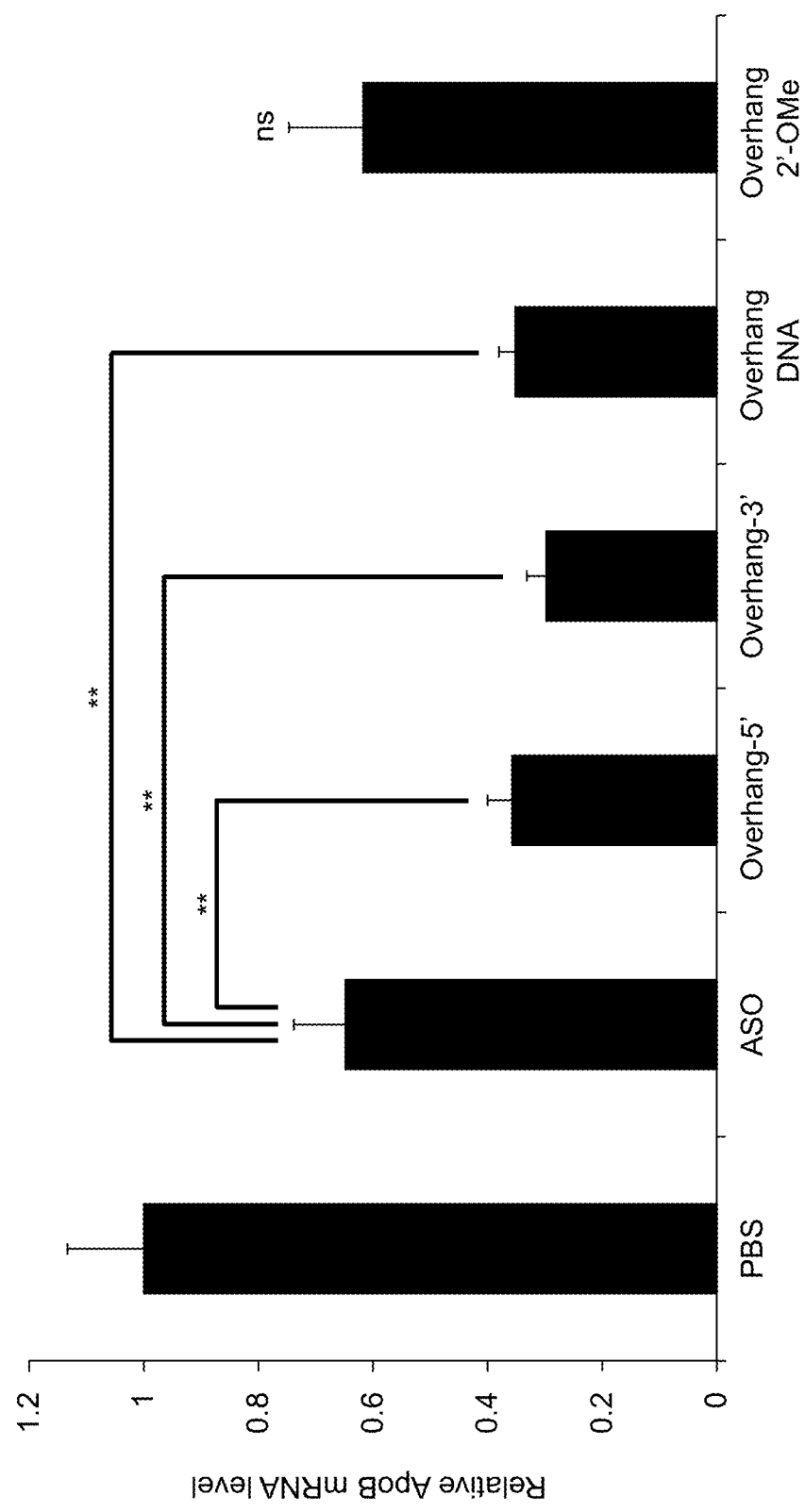
FIG. 8 shows a graph showing the result of an experiment described in Example 2, comparing the inhibitory effects on the expression of a target gene (ApoB) by a nucleic acid complex according to a particular embodiment. The double asterisk (**) indicates $p<0.01$. The sign "ns" indicates no significant difference when compared with the control (ASO).

The result of Example 2 is shown in the graph of FIG. 8. An inhibition of ApoB mRNA expression was indicated in all the groups treated with the five nucleic acid agents, as compared to the negative control (PBS alone). In particular, the inhibition degrees obtained by the three double-stranded agents ("Overhang-5'," "Overhang-3'," and "Overhang DNA") were larger than that obtained by the single-stranded ASO, and the differences were statistically significant. However, the double-stranded agent in which a portion of the region complementary to the first strand in the second strand was replaced with RNase-resistant 2'-O-methyl RNAs ("Overhang 2'-OMe") did not show an increase in the inhibitory effect as compared to the single-stranded ASO.

Example 3

Figure 9:
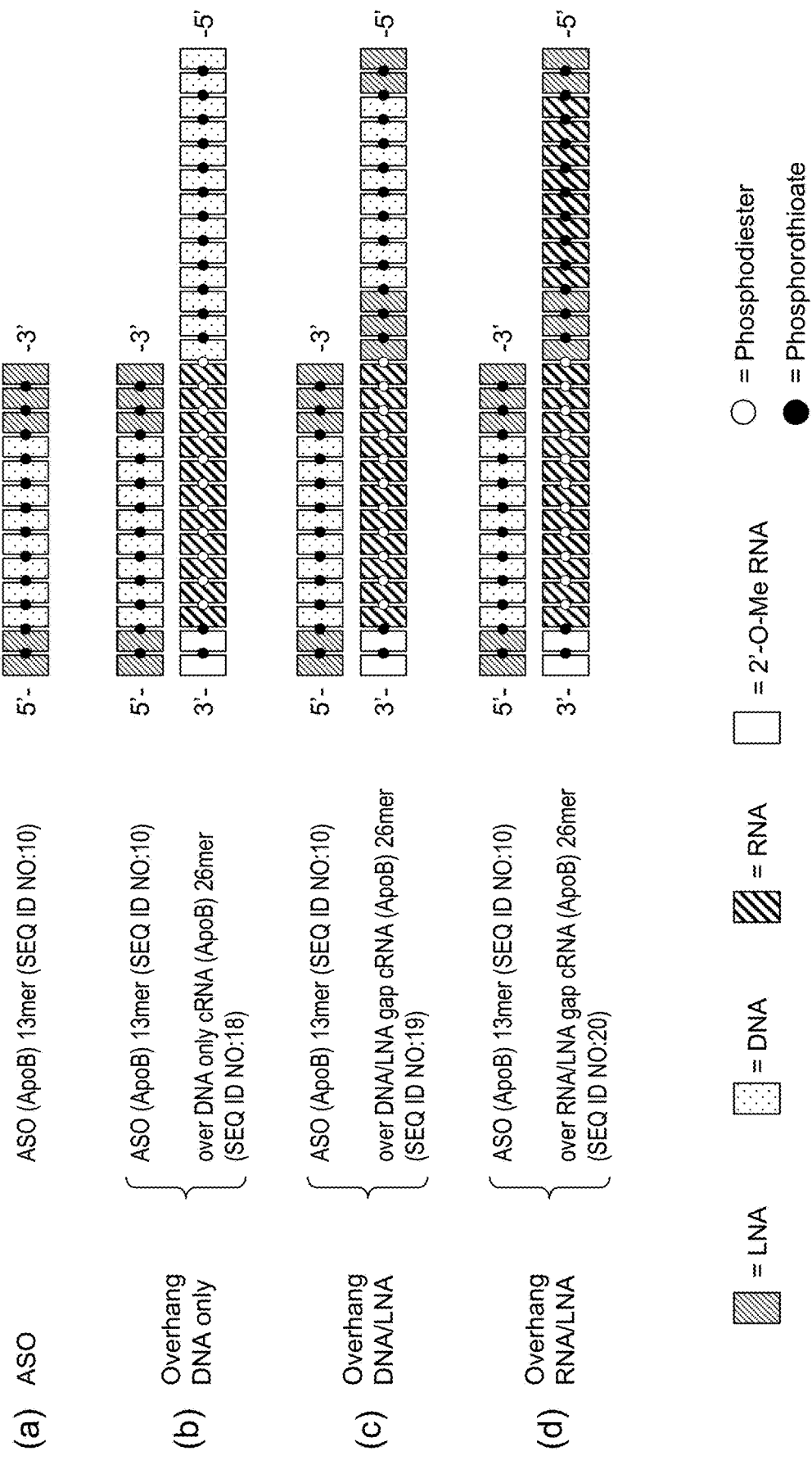
FIG. 9 shows a schematic diagram of the structures of nucleic acids used in Example 3. For each nucleic acid, the name of the nucleic acid, the name of each oligonucleotide, and the structure are shown in this order from left to right.

The usefulness of a double-stranded nucleic acid agent according to an embodiment having different chemical modifications in the overhang region of the second strand was tested by an in vivo experiment. The target was ApoB mRNA, similarly to Example 1. The control (ASO) was also the same single-stranded LNA/DNA gapmer as in Example 1. The LNA/DNA gapmer (first strand) was annealed to a complementary strand (second strand) to prepare three double-stranded agents (referred to as "Overhang DNA only," "Overhang DNA/LNA," and "Overhang RNA/LNA"). The overhang region of the "Overhang DNA only" comprises 13 DNA nucleosides. The overhang region of the "Overhang DNA/LNA" comprises two LNA nucleosides, eight DNA nucleosides, and three LNA nucleosides in this order from the 5' end. In the "Overhang RNA/LNA," DNAs in the overhang region of the "Overhang DNA/LNA" are replaced with RNAs. The sequences, chemical modifications, and structures of the polynucleotides used in Example 3 are shown in Table 1 and FIG. 9. The double-stranded agents were prepared similarly to Example 1.

(In Vivo Experiment)

Each nucleic acid agent was injected intravenously at a dose of 0.173 µmol/kg to mice (n=4) via tail vein. Mice used and a method of analyzing ApoB mRNA expression are as described in Example 1.

(Result)

Figure 10:
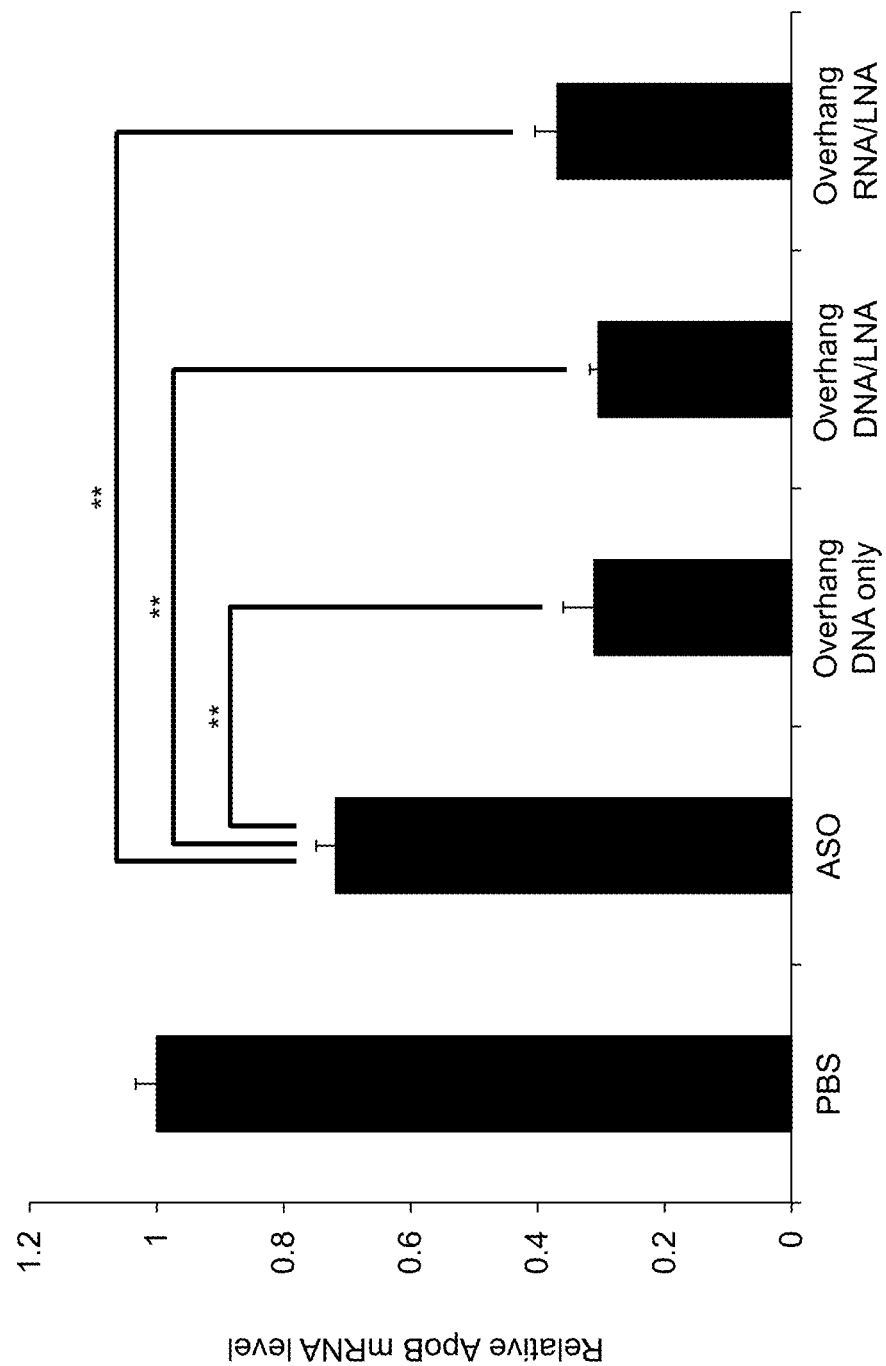
FIG. 10 shows a graph showing the result of an experiment described in Example 3, comparing the inhibitory effects on the expression of a target gene (ApoB) by a nucleic acid complex according to a particular embodiment. The double asterisk (**) indicates $p<0.01$.

The result of Example 3 is shown in the graph of FIG. 10. An inhibition of ApoB mRNA expression was indicated in all the groups treated with the four nucleic acid agents, as compared to the negative control (PBS alone). The inhibition degrees obtained by the three double-stranded agents according to a particular embodiment of the present invention ("Overhang DNA only," "Overhang DNA/LNA," and "Overhang RNA/LNA") were larger than that obtained by the single-stranded ASO, and the differences were statistically significant.

Example 4

Figure 11:
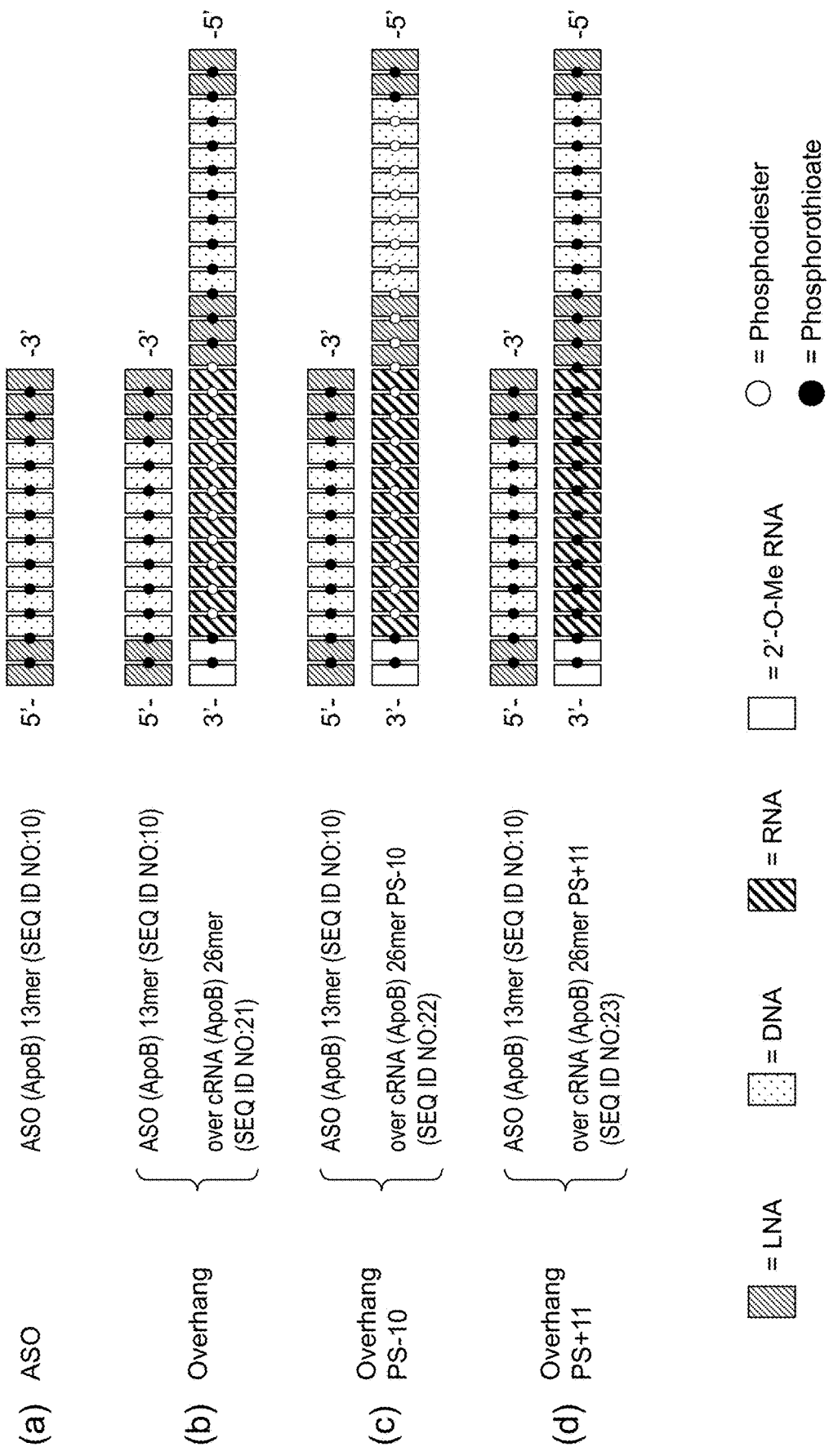
FIG. 11 shows a schematic diagram of the structures of nucleic acids used in Example 4. For each nucleic acid, the name of the nucleic acid, the name of each oligonucleotide, and the structure are shown in this order from left to right.

The usefulness of a double-stranded nucleic acid agent according to an embodiment wherein the second strand is different in the number of internucleoside linkages modified by phosphorothioate substitutions strand was tested by an in vivo experiment. The target was ApoB mRNA, similarly to Example 1. The control (ASO) was also the same single-stranded LNA/DNA gapmer as in Example 1. The LNA/DNA gapmer (first strand) was annealed to a complementary strand (second strand) to prepare three double-stranded agents (referred to as "Overhang", "Overhang PS−10," and "Overhang PS+11"). In the "Overhang," 25 internucleoside linkages of the second strand (26 bases in length) consisted of twelve phosphorothioate linkages (in the overhang region), eleven phosphodiester linkages, and two phosphorothioate linkages in this order from the 5' end. In the "Overhang PS−10," the twelve phosphorothioate linkages in the overhang region of the "Overhang" other than the two phosphorothioate linkages from the 5' end were replaced with phosphodiester linkages. In the "Overhang PS+11," all the internucleoside linkages within the second strand were phosphorothioate linkages. The sequences, chemical modifications, and structures of the polynucleotides used in Example 4 are shown in Table 1 and FIG. 11. The double-stranded agents were prepared similarly to Example 1.

(In Vivo Experiment)

Each nucleic acid agent was injected intravenously at a dose of 0.173 µmol/kg to mice (n=4) via tail vein. Mice used and a method of analyzing ApoB mRNA expression were as described in Example 1. In addition, the intrahepatic concentration of the nucleic acid agent was measured by quantitative RT-PCR using the TaqMan Small RNA Assay (Roche Applied Science) according to the protocol.

(Result)

The result of Example 4 is shown in the graph of FIG. 12. An inhibition of ApoB mRNA expression was indicated in all the groups treated with the four nucleic acid agents, as compared to the negative control (PBS alone). In particular, the inhibition degrees obtained by the two double-stranded agents ("Overhang" and "Overhang PS+11") were larger than that obtained by the single-stranded ASO, and the differences were statistically significant. On the other hand, the inhibition degree obtained by the double-stranded agent in which the majority of the phosphorothioate linkages in the overhang region of the second strand were replaced with phosphodiester linkages ("Overhang PS-10") was similar to that obtained by the single-stranded ASO.

Consistent with this tendency, the intrahepatic concentrations of the "Overhang" and "Overhang PS+11" were significantly increased compared to the single-stranded ASO. However, the intrahepatic concentration of the "Overhang PS-10" was similar to that of the single-stranded ASO.

These results indicated that an increase in the number of phosphorothioate linkages in the overhang region of the second strand of the double-stranded agent leads to an enhanced delivery of the double-stranded agent into the living body and an enhanced antisense effect.

Example 5

Figure 13:
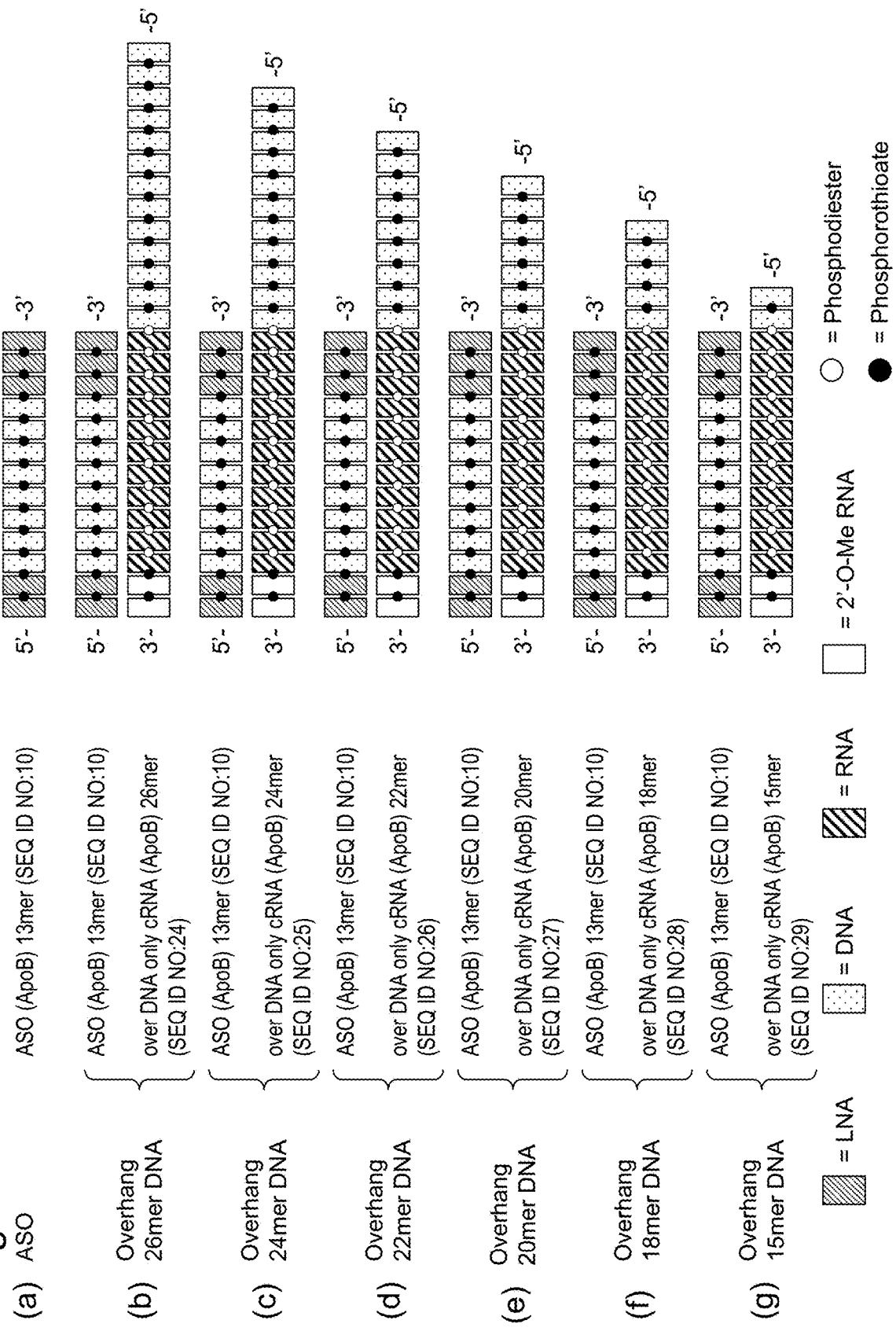
FIG. 13 shows a schematic diagram of the structures of nucleic acids used in Example 5. For each nucleic acid, the name of the nucleic acid, the name of each oligonucleotide, and the structure are shown in this order from left to right.

The usefulness of double-stranded nucleic acid agents according to an embodiment wherein the second strand ranges from 15-mer to 26-mer (the overhang region in the second strand ranges from 2 bases to 13 bases in length) was tested by an in vivo experiment. The target was ApoB mRNA, similarly to Example 1. The control (ASO) was also the same single-stranded LNA/DNA gapmer as in Example 1. The LNA/DNA gapmer (first strand) was annealed to a complementary strand (second strand) to prepare six double-stranded agents ("Overhang 26-mer DNA," "Overhang 24-mer DNA," "Overhang 22-mer DNA," "Overhang 20-mer DNA," "Overhang 18-mer DNA," and "Overhang 15-mer DNA"). The overhang regions of these double-stranded agents have 13, 11, 9, 7, 5, or 2 DNA nucleosides. The sequences, chemical modifications, and structures of the polynucleotides used in Example 5 are shown in Table 1 and FIG. 13. The double-stranded agents were prepared similarly to Example 1.

(In Vivo Experiment)

Each nucleic acid agent was injected intravenously at a dose of 0.173 µmol/kg to mice (n=4) via tail vein. Mice used and methods of analyzing ApoB mRNA expression and the intrahepatic concentration of a nucleic acid agent are the same as in Example 4.

(Result)

The result of Example 5 is shown in the graph of FIG. 14. A double-stranded agent with a longer overhang region showed a tendency of an enhanced degree of ApoB mRNA inhibition and an increased intrahepatic concentration of the nucleic acid agent. In particular, double-stranded agents wherein the second strand ranges from 20-mer to 26-mer (namely, the overhang region of the second strand is from 7 to 13 bases in length, particularly from 9 to 13 bases in length) showed a high degree of ApoB mRNA inhibition and a high intrahepatic concentration of the nucleic acid agent.

Example 6

Figure 15:
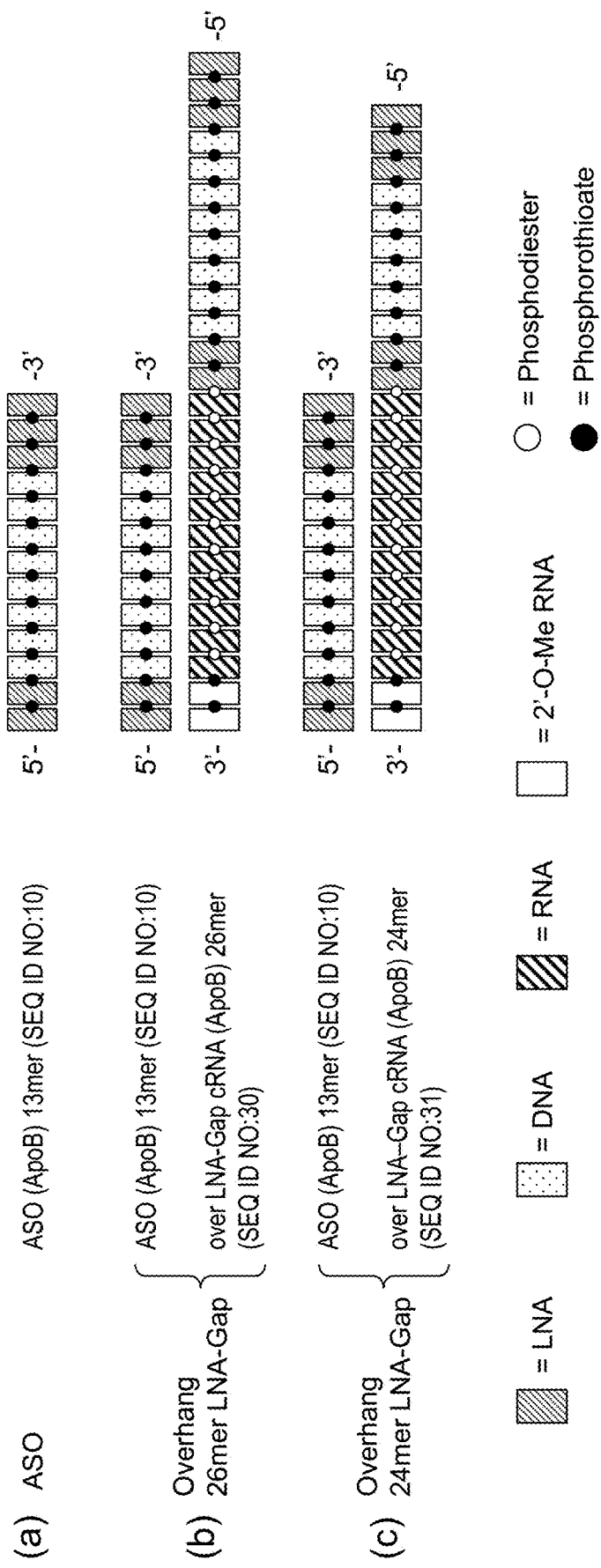
FIG. 15 shows a schematic diagram of the structures of nucleic acids used in Example 6. For each nucleic acid, the name of the nucleic acid, the name of each oligonucleotide, and the structure are shown in this order from left to right.

The usefulness of a double-stranded nucleic acid agent according to an embodiment wherein the second strand is 24- or 26-mer (the overhang region in the second strand is 11 or 13 bases in length) and an overhang region of the second strand has chemical modifications different from those in Example 5 was tested by an in vivo experiment. The target was ApoB mRNA, similarly to Example 1. The control (ASO) was also the same single-stranded LNA/DNA gapmer as in Example 1. The LNA/DNA gapmer (first strand) was annealed to a complementary strand (second strand) to prepare two double-stranded agents ("Overhang 26-mer LNA-Gap" and "Overhang 24-mer LNA-Gap"). The overhang regions of these double-stranded agents comprise three and two LNA nucleosides at the 5' and 3' ends, respectively, and in-between DNA nucleosides, and the lengths are 13 and 11 bases, respectively. The sequences, chemical modifications, and structures of the polynucleotides used in Example 6 are shown in Table 1 and FIG. 15. The double-stranded agents were prepared similarly to Example 1.

(In Vivo Experiment)

Each nucleic acid agent was injected intravenously at a dose of 0.173 µmol/kg to mice (n=4) via tail vein. Mice used and methods of analyzing ApoB mRNA expression and the intrahepatic concentration of a nucleic acid agent are the same as in Example 4.

(Result)

The result of Example 6 is shown in the graph of FIG. 16. In cases where the second strand was 24-mer or 26-mer (namely, the overhang region of the second strand was 11 bases or 13 bases in length), both of the degree of ApoB mRNA inhibition and intrahepatic concentration of a nucleic acid agent obtained were larger than those obtained by the single-stranded ASO, and the differences were statistically significant.

Example 7

Figure 17:
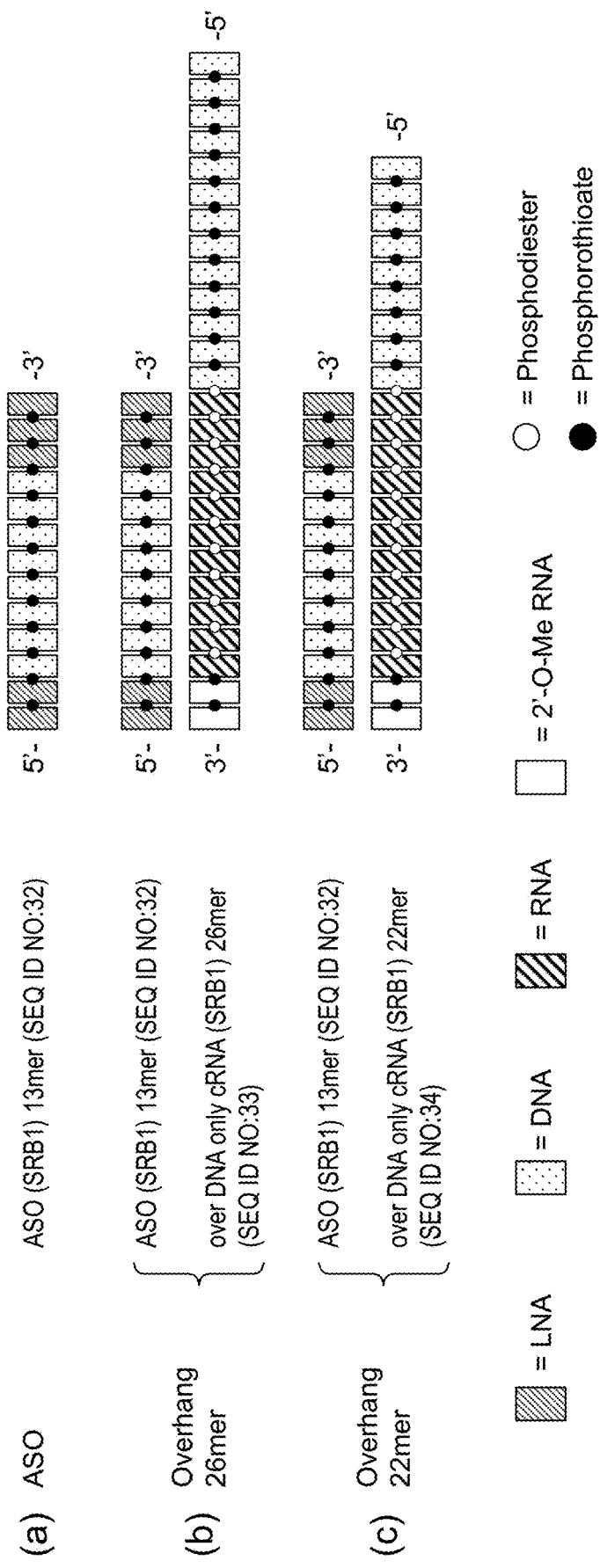
FIG. 17 shows a schematic diagram of the structures of nucleic acids used in Example 7. For each nucleic acid, the name of the nucleic acid, the name of each oligonucleotide, and the structure are shown in this order from left to right.

The usefulness of a double-stranded nucleic acid agent according to an embodiment wherein an mRNA of scavenger receptor B1 (SRB1), a gene different from ApoB targeted in Examples 1 to 6, is targeted and the second strand is 22-mer or 26-mer (the overhang region of the second strand is 9 or 13 bases in length) was tested by an in vivo experiment. The control (ASO) was a 13-mer single-stranded LNA/DNA gapmer. The LNA/DNA gapmer comprises two and three LNA nucleosides at the 5' and 3' ends, respectively, and in-between eight DNA nucleosides. The LNA/DNA gapmer is complementary to the mouse scavenger receptor B1 (SRB1) mRNA (SEQ ID NO: 2) from positions 2479 to 2491. The LNA/DNA gapmer (first strand) was annealed to a complementary strand (second strand) to prepare two double-stranded agents ("Overhang 26-mer" and "Overhang 22-mer"). The overhang regions of these double-stranded agents respectively have 13 and 9 DNA nucleosides. The sequences, chemical modifications, and structures of the polynucleotides used in Example 7 are shown in Table 1 and FIG. 17. The double-stranded agents were prepared similarly to Example 1.

(In Vivo Experiment)

Each nucleic acid agent was injected intravenously at a dose of 0.173 µmol/kg to mice (n=4) via tail vein. Mice used and a method of analyzing SRB1 mRNA expression are as described in Example 1, except for the primers used for quantitative RT-PCR to quantify SRB1 mRNA.

(Result)

Figure 18:
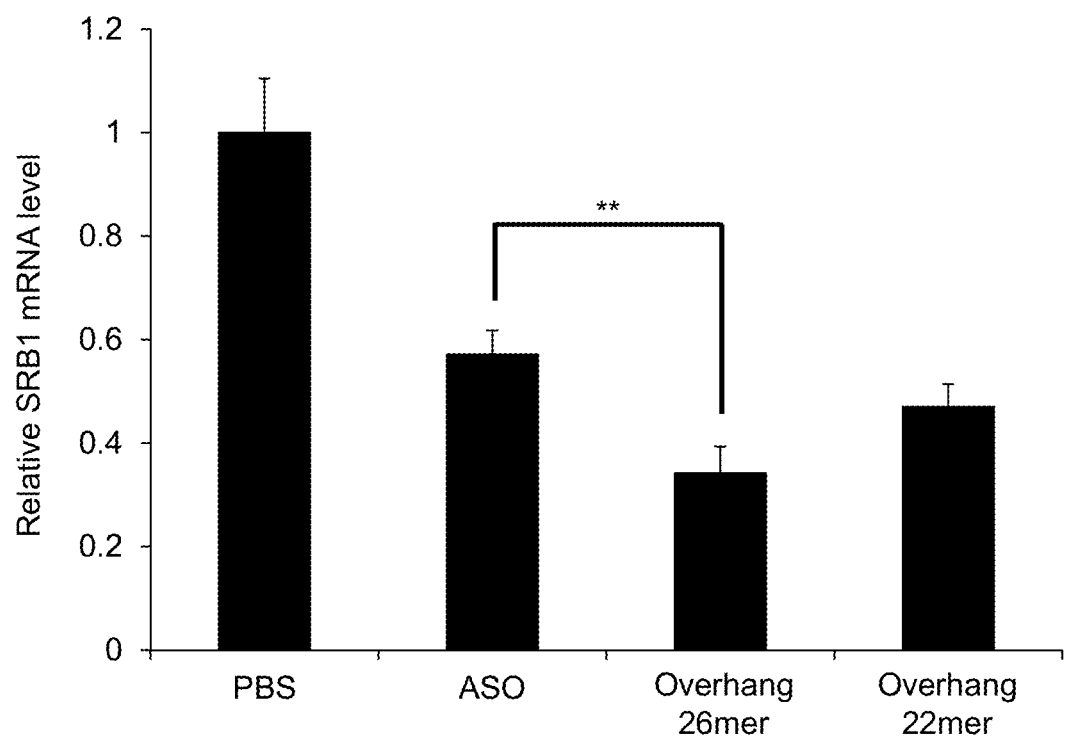
FIG. 18 shows a graph showing the result of an experiment described in Example 7, comparing the inhibitory effects on the expression of a target gene (SRB1) by a nucleic acid complex according to a particular embodiment. The double asterisk (**) indicates $p<0.01$.

The result of Example 7 is shown in the graph of FIG. 18. The double-stranded agent wherein the second strand is 26-mer or 22-mer showed a tendency of an enhanced inhibition of SRB1 expression as compared to the single-stranded ASO. In particular, in a case where the second strand is a double-stranded agent of 26-mer (namely, the overhang region of the second strand is 13 bases in length), the degree of SRB1 mRNA inhibition obtained was larger than that obtained by the single-stranded ASO, and the difference was statistically significant.

This result indicated that the effect of the double-stranded nucleic acid complex according to the present invention is not specific to ApoB and can target transcription products of various genes.

Example 8

Figure 19:
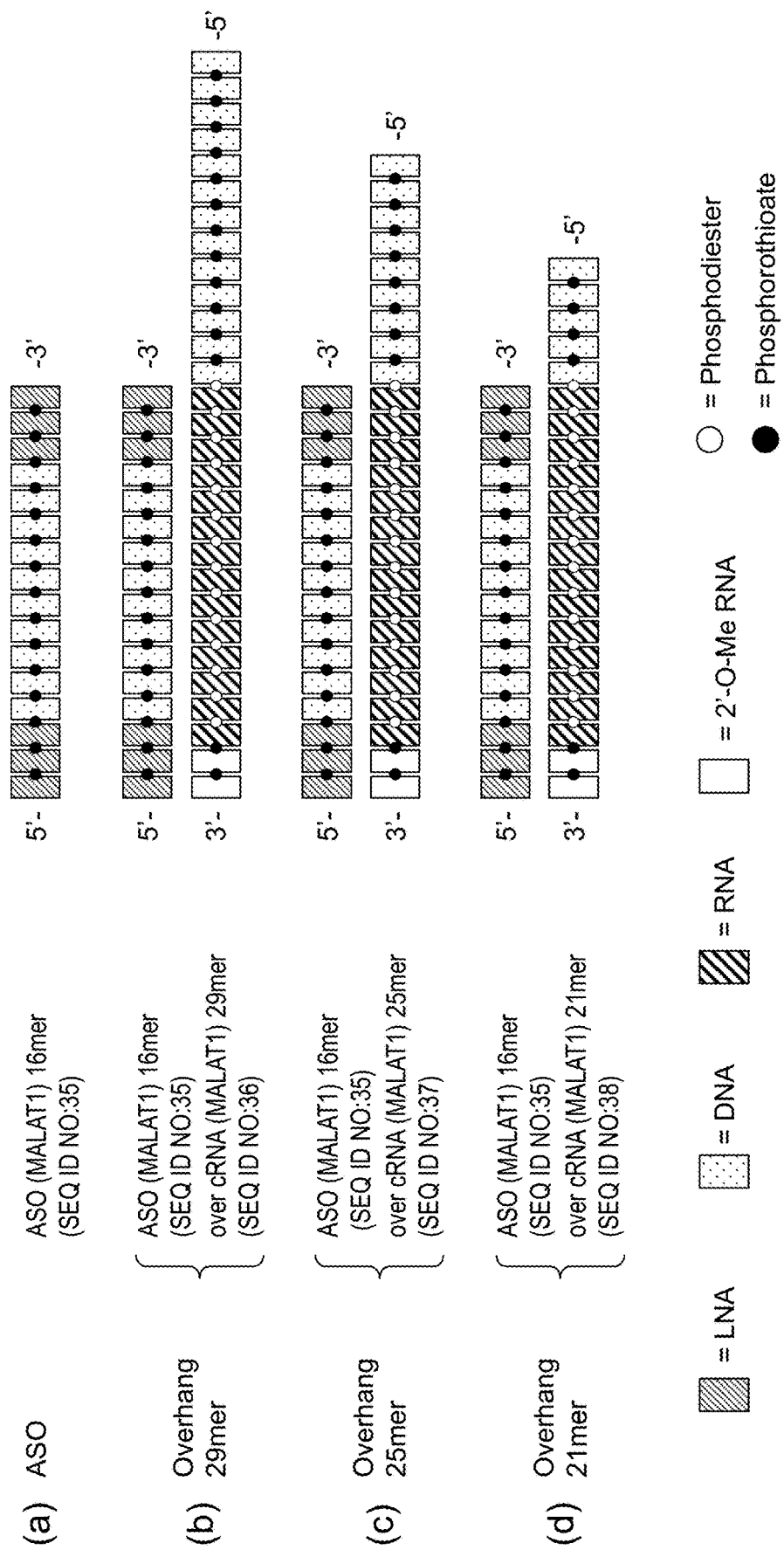
FIG. 19 shows a schematic diagram of the structures of nucleic acids used in Example 8. For each nucleic acid, the name of the nucleic acid, the name of each oligonucleotide, and the structure are shown in this order from left to right.

The usefulness of a double-stranded nucleic acid agent according to an embodiment wherein a non-coding RNA of metastasis associated lung adenocarcinoma transcript 1 (MALAT1), a gene different from ApoB and SRB1 targeted in Examples 1 to 7, is targeted and the second strand is 21-, 25-, or 29-mer (the overhang region of the second strand is 5, 9, or 13 bases in length) was tested by an in vivo experiment. The control (ASO) was a 16-mer single-stranded LNA/DNA gapmer. The LNA/DNA gapmer comprises three and three LNA nucleosides at the 5' and 3' ends, respectively, and in-between ten DNA nucleosides. The LNA/DNA gapmer was complementary to the mouse metastasis associated lung adenocarcinoma transcript 1 (MALAT1) non-coding RNA (SEQ ID NO: 3) from positions 1316 to 1331. The LNA/DNA gapmer (first strand) was annealed to a complementary strand (second strand) to prepare three double-stranded agents ("Overhang 29-mer," "Overhang 25-mer," and "Overhang 21-mer"). The overhang regions of these double-stranded agents respectively have 13, 9, and 5 DNA nucleosides. The sequences, chemical modifications, and structures of the polynucleotides used in Example 8 are shown in Table 1 and FIG. 19. The double-stranded agents were prepared similarly to Example 1.

(In Vivo Experiment)

Each nucleic acid agent was injected intravenously at a dose of 0.0692 µmol/kg to mice (n=4) via tail vein. Mice used and a method of analyzing RNA expression are as described in Example 1, except for the primers used for quantitative RT-PCR to quantify MALAT1 ncRNA.

(Result)

Figure 20:
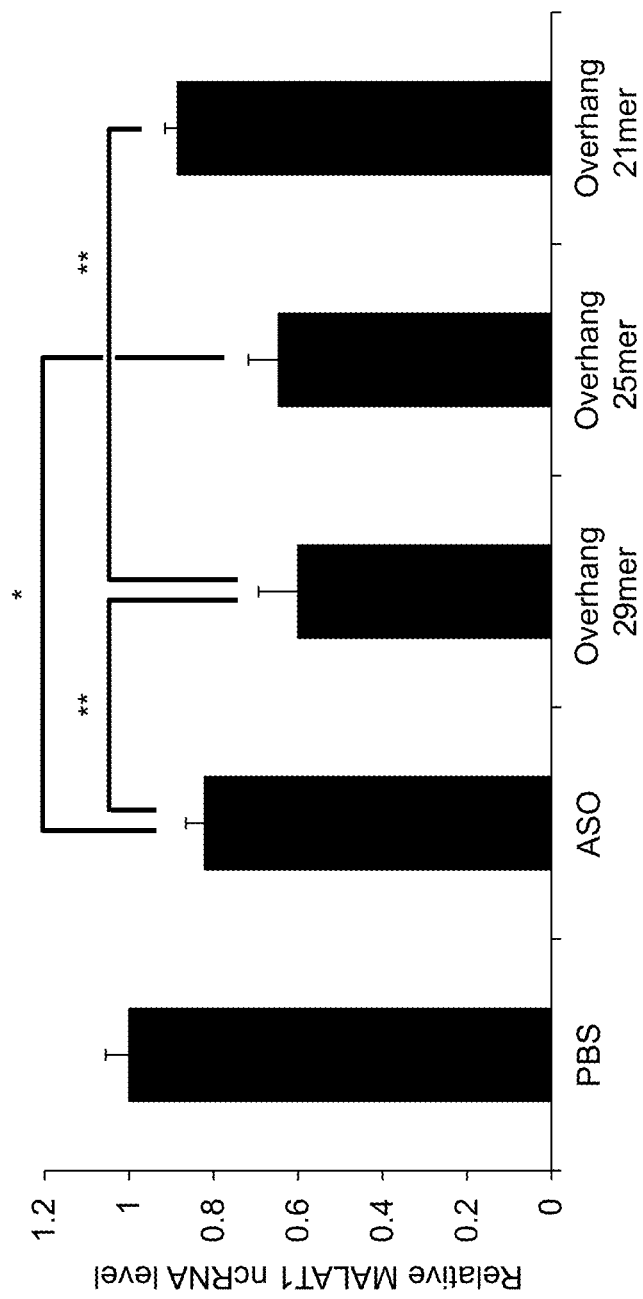
FIG. 20 shows a graph showing the result of an experiment described in Example 8, comparing the inhibitory effects on the level of a target transcription product (MALAT) by a nucleic acid complex according to a particular embodiment. The single asterisk (*) indicates p<0.05, and the double asterisk (**) indicates p<0.01.

The result of Example 8 is shown in the graph of FIG. 20. A double-stranded agent with a longer overhang region showed a tendency of enhanced inhibition of MALAT1 expression. In particular, in cases where the second strand is a double-stranded agent of 29- or 25-mer (namely, the overhang region of the second strand is 13 or 9 bases in length), the degree of MALAT1 ncRNA inhibition obtained was larger than that obtained by the single-stranded ASO, and the differences were statistically significant.

Example 9

Figure 21:
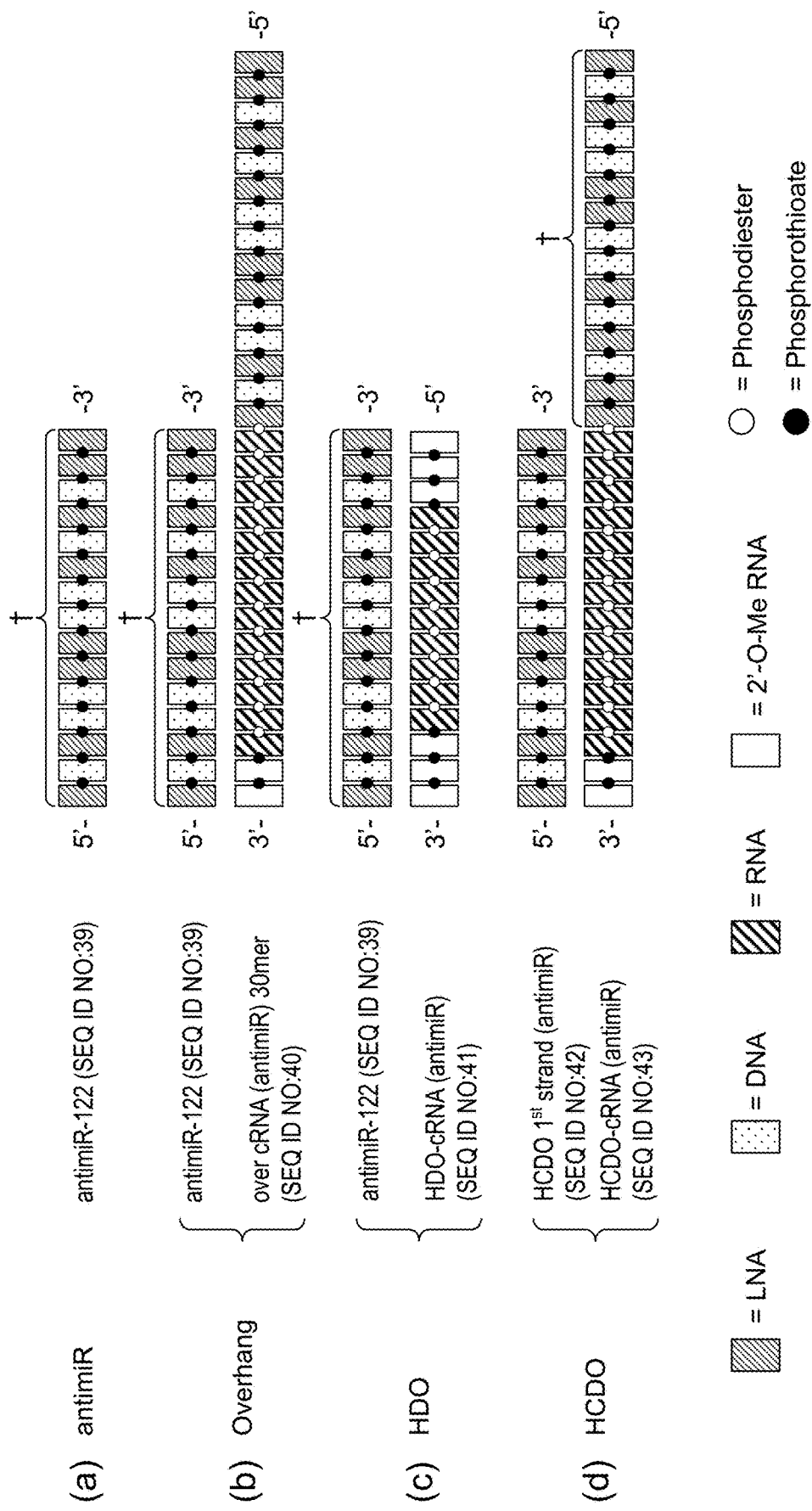
FIG. 21 shows a schematic diagram of the structures of nucleic acids used in Example 9. For each nucleic acid, the name of the nucleic acid, the name of each oligonucleotide, and the structure are shown in this order from left to right. The dagger "†" indicates a polynucleotide region of the same base sequence having an antisense effect.

The usefulness of a double-stranded nucleic acid agent according to an embodiment wherein microRNA-122 (miR122), which is different from ApoB, SRB1, and MALAT1 targeted in Examples 1 to 8, is targeted and the second strand is 30-mer (the overhang region of the second strand is 15 bases in length) was tested by an in vivo experiment. The control (antimiR) was a 15-mer single-stranded LNA/DNA mixmer. The LNA/DNA mixmer was complementary to the mouse miR122 (SEQ ID NO: 4) from positions 2 to 16. The LNA/DNA mixmer (first strand) was annealed to a complementary strand (second strand) to prepare double-stranded agents ("Overhang" and "HDO"). In the "Overhang," the second strand has an overhang region of 15 bases in length which consists of DNA nucleosides and LNA nucleosides and is located on the 5' terminal side of a region complementary to the first strand. In the "HDO", the second strand is completely complementary to the first strand. The "HDO" is an embodiment of the invention described in International Publication No. WO2013/089283. Additionally, a "HCDO" (hetero-chimera-duplex oligonucleotide) was prepared, which has a duplex nucleic acid structure of 15 bases in length located on the 3' terminal side of a sequence complementary to the mouse miR122 (SEQ ID NO: 4) from positions 2 to 16. The "HCDO" is an embodiment of the invention described in International Publication No. WO2014/192310. The sequences, chemical modifications, and structures of the polynucleotides used in Example 9 are shown in Table 1 and FIG. 21. The double-stranded agents were prepared similarly to Example 1.

(In Vivo Experiment)

Each nucleic acid agent was injected intravenously at a dose of 5.89 nmol/kg to mice (n=5) via tail vein. A method of analyzing the used mice is as described in Example 1. The IsogenII kit (GeneDesign, Inc.) was used according to the protocol to extract microRNA. Synthesis of cDNA and quantitative RT-PCR were performed using the TaqMan MicroRNA Assays (Thermo Fisher Scientific) according to the protocol. The primers used in the quantitative RT-PCR were designed according to various numbers of genes and produced by Thermo Fisher Scientific (former Life Technologies Corp). On the basis of the thus-obtained result of the quantitative RT-PCR, the ratio of the expression level of miR122 to U6 (an internal reference gene) was calculated individually. In addition, the results from the individual groups were compared and further evaluated by Bonferroni test.

(Result)

Figure 22:
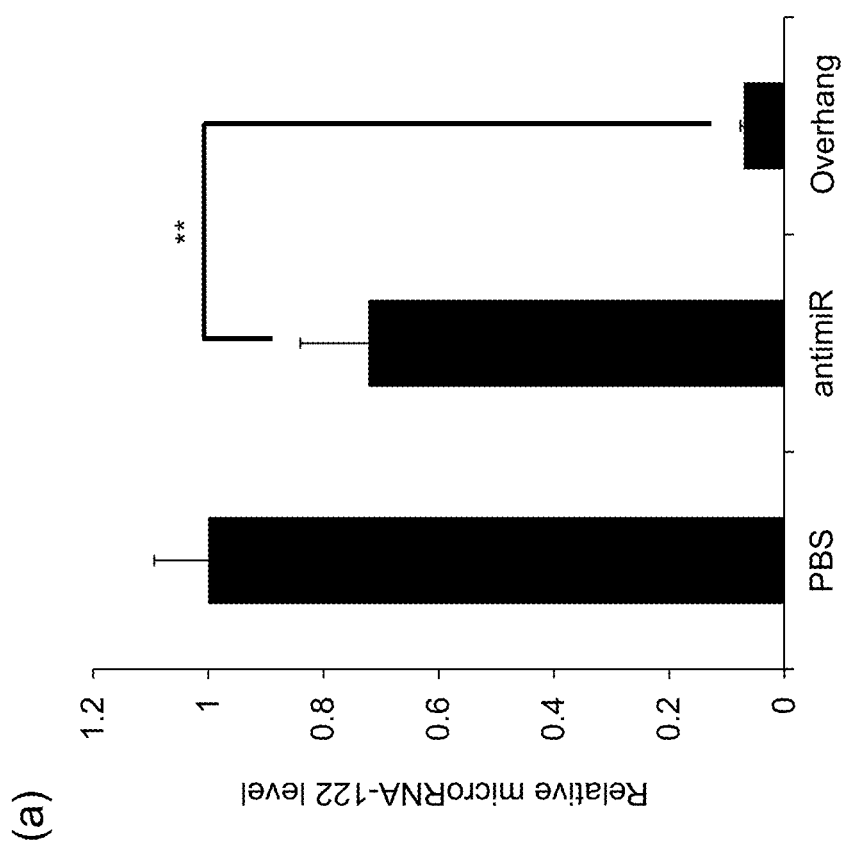
FIG. 22 shows graphs showing the result of an experiment described in Example 9, comparing the inhibitory effects on the level of a target transcription product (miR-122) by a nucleic acid complex according to a particular embodiment. The single asterisk (*) indicates p<0.05, and the double asterisk (**) indicates p<0.01.

The result of Example 9 is shown in the graph of FIG. 22. The degree of miR122 inhibition obtained by the double-stranded agent having an overhang region according to an embodiment of the present invention ("Overhang") was larger than that obtained by the single-stranded ASO ("anti-miR"), and the difference was statistically significant (FIG. 22a). Additionally, the degree of miR122 inhibition obtained by the double-stranded agent having an overhang region according to an embodiment of the present invention ("Overhang") was larger than those obtained by the "HDO" and the "HCDO," and the differences were statistically significant (FIG. 22b).

Example 10

Double-stranded and single-stranded nucleic acid agents were assumed to have different pharmacokinetics profiles due to different binding properties to serum proteins. To examine this assumption, the binding properties of the nucleic acid agents to serum proteins were evaluated using the gel shift assay.

(Gel Shift Assay)

The single-stranded ASO and double-stranded agent "Overhang" used in Example 1 were labeled with a fluorescent dye (Alexa-568). In an ex vivo experiment, the fluorescent dye-labeled single-stranded or double-stranded nucleic acid agent (15 μmol) was mixed with an undiluted solution of ICR mouse serum or the serum solution diluted 2 to 8 folds with PBS (22.5 μl), and 10% sucrose (6 μl) to prepare samples. Each of the mixture samples was electrophoresed (at 100 V, for 25 minutes) on a 2% agarose gel in Tris-borate-EDTA buffer. The fluorescent dye-labeled nucleic acid agents were detected under UV light using a ChemiDoc Touch Imaging System (BIO RAD).

(Result)

Figure 23:
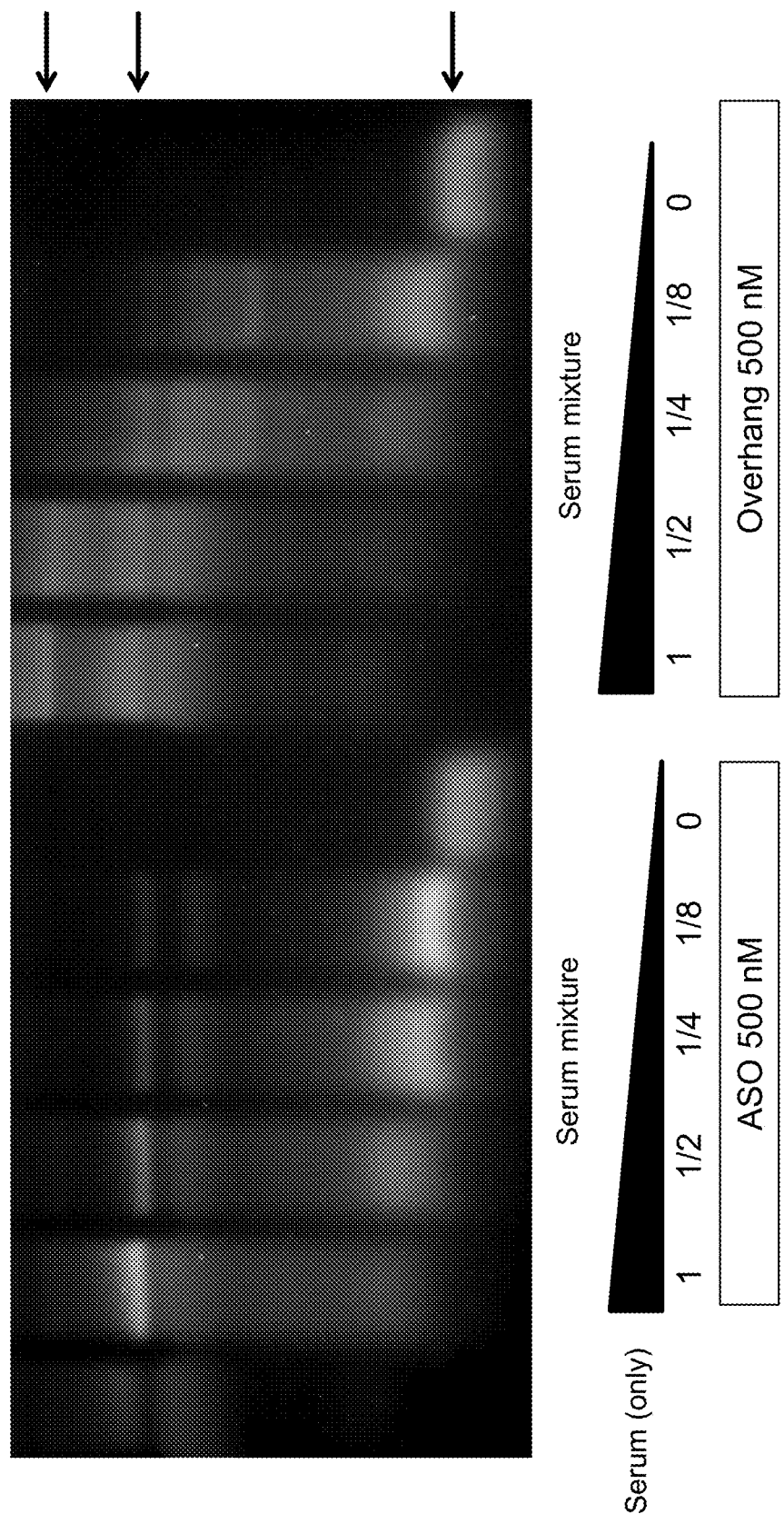
FIG. 23 shows the result of a gel shift assay described in Example 10.

As shown in FIG. 23, with respect to the single-stranded ASO and double-stranded agent according to an embodiment of the present invention ("Overhang"), the amount of the lower band (indicated by the arrow at the bottom), which represents the unbound nucleic acid agent, was increased by dilution of the serum, whereas the upper two bands (indicated by the upper two arrows), which represent the nucleic acid agents bound with serum proteins, were decreased by the dilution of the serum. In particular, the upper bands among the two bands indicating the binding with serum proteins showed a higher intensity in the double-stranded agent than in the single-stranded ASO. This result indicated that the double-stranded agent and single-stranded ASO have different properties with respect to binding with serum proteins.

Example 11

The result of Example 10 suggested that the double-stranded agent according to an embodiment of the present invention has a higher capability of binding to a serum protein with a large particle diameter, as compared to the single-stranded agent. To examine this, the diffusion time of a complex between a nucleic acid agent and serum proteins was measured using the fluorescence correlation spectroscopy (FCS). The diffusion time is proportional to the particle diameter of the complex. The diffusion time was used to evaluate the size of a protein bound to the nucleic acid agent.

(Fcs Assay)

The single-stranded ASO and double-stranded agent ("Overhang") used in Example 1 were labeled with a fluorescent dye (Alexa-647). In an ex vivo experiment, the fluorescent dye-labeled or unlabeled single-stranded or double-stranded nucleic acid agent was mixed with a undiluted solution of ICR mouse serum or the serum diluted 2 to 8 folds with PBS (22.5 μl) to prepare samples containing the nucleic acid agent at a final concentration of 10 nM. The diffusion time in each of the mixture samples was measured using a MF 20 (OLYMPUS).

(Result)

Figure 24:
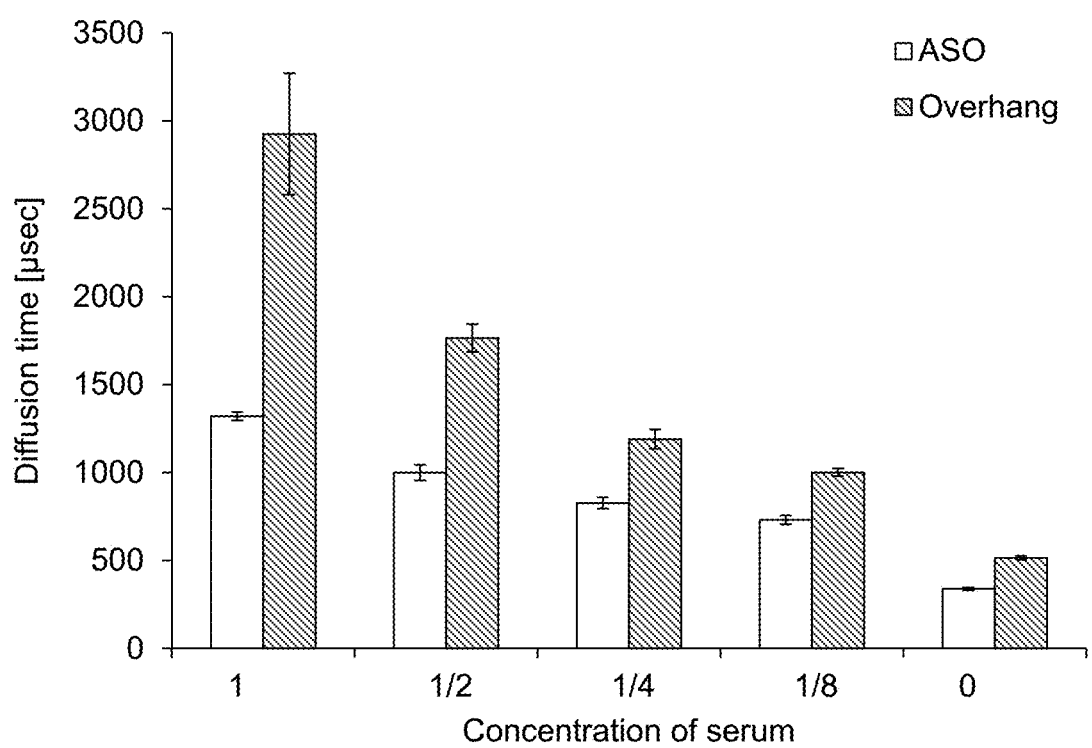
FIG. 24 shows a graph showing the result of an experiment described in Example 11, where the size of serum proteins binding to nucleic acid agents is evaluated by the fluorescence correlation spectroscopy (FCS).

As shown in FIG. 24, the double-stranded agent according to an embodiment of the present invention showed a significantly longer diffusion time in the serum mixture, as compared to the single-stranded ASO. This result indicated that the serum protein bound to the double-stranded agent is different from that bound to the single-stranded agent and the double-stranded agent binds to a serum protein of a larger size.

Example 12

Figure 25:
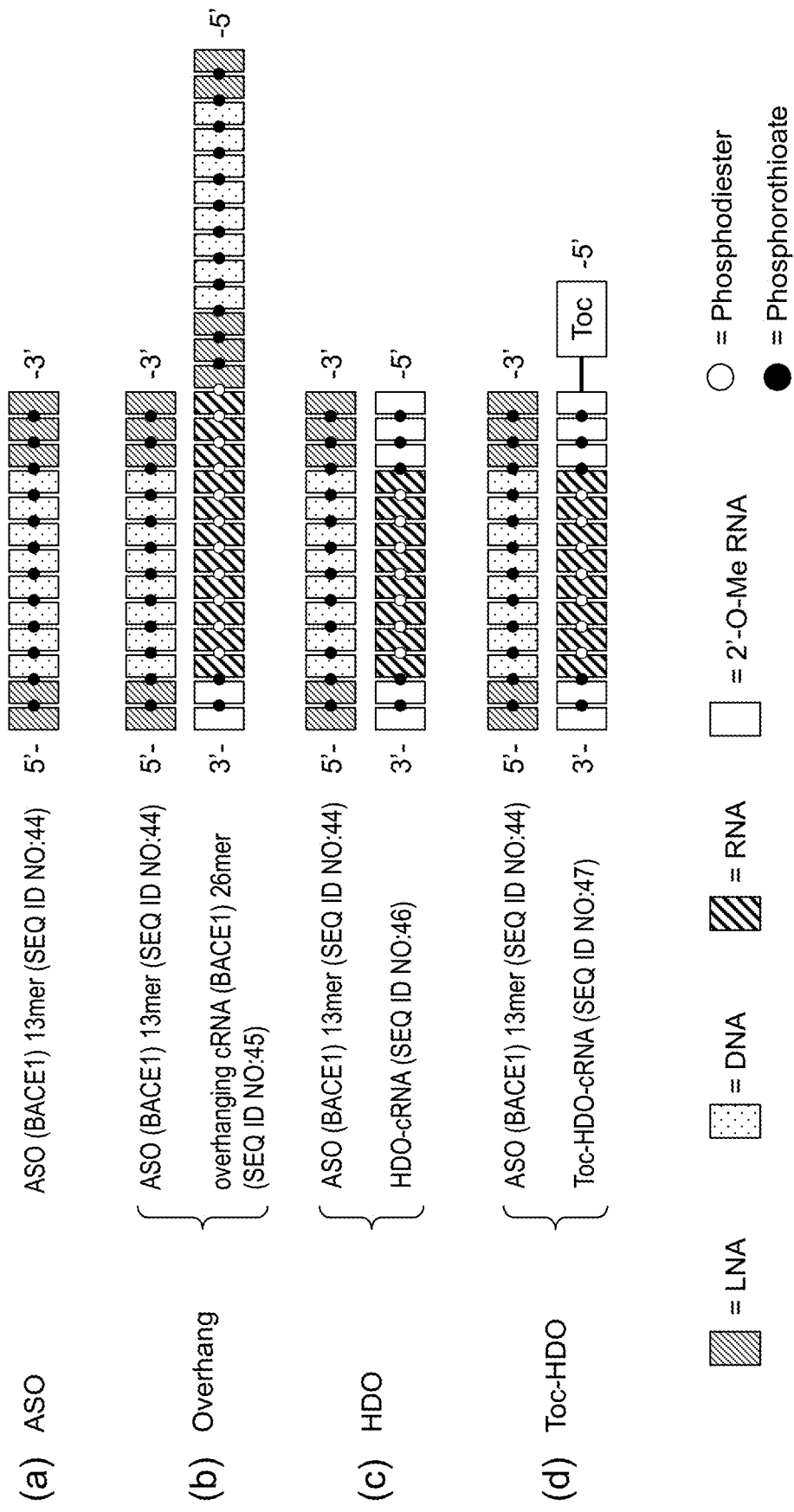
FIG. 25 shows a schematic diagram of the structures of nucleic acids used in Example 12. For each nucleic acid, the name of the nucleic acid, the name of each oligonucleotide, and the structure are shown in this order from left to right. The sign "Toc" means tocopherol.

The usefulness of an intraventricularly administered double-stranded nucleic acid agent according to an embodiment in the brain tissue was tested by an in vivo experiment. The control (ASO) was a 13-mer single-stranded LNA/DNA gapmer. The LNA/DNA gapmer comprises two and three LNA nucleosides at the 5' and 3' ends, respectively, and in-between eight DNA nucleosides. The LNA/DNA gapmer was complementary to the mouse beta-secretase 1 (BACE1) mRNA (SEQ ID NO: 5) from positions 1569 to 1581. The LNA/DNA gapmer (first strand) was annealed to a complementary strand (second strand) to prepare three double-stranded agents ("Overhang," "HDO," and "Toc-HDO"). In the "Overhang," the second strand has an overhang region of 13 bases in length located on the 5' terminal side of a region complementary to the first strand. In the "HDO," the second strand is completely complementary to the first strand. In the "Toc-HDO," the second strand has a tocopherol conjugated to the 5' end of the strand which is completely complementary to the first strand. The sequences, chemical modifications, and structures of the polynucleotides used in Example 12 are shown in Table 1 and FIG. 25. The double-stranded agents were prepared similarly to Example 1.

(In Vivo Experiment)

Seven-week-old female ICR mice were fixed on a stereotaxic apparatus under 2.5 to 4% isoflurane anesthesia. Then, the skin was excised between both ears in 2 to 3-cm in anteroposterior direction and a drill with a diameter of 1 mm was used to make a hole at 1 mm left and 0.2 mm posterior from bregma. A Hamilton syringe was filled with a nucleic acid agent. The syringe needle was inserted around 3 mm into the hole and the nucleic acid agent was administered intraventricularly at a dose of 6 or 12 μmol per mouse and a flow rate of 2 to 3 μl/minute (n=4 to 5 in the experiments of FIGS. 26a and 26b; n=3 in the experiment of FIG. 26c), and the skin was then sutured with a nylon thread. Seven days after the injection, mice were euthanized to collect the left hippocampus. Subsequently, the expression of BACE1 mRNA was analyzed in the same manner as described in Example 1, except for the primers used in the quantitative RT-PCR for quantification of BACE1 mRNA.

(Result)

Figure 26:
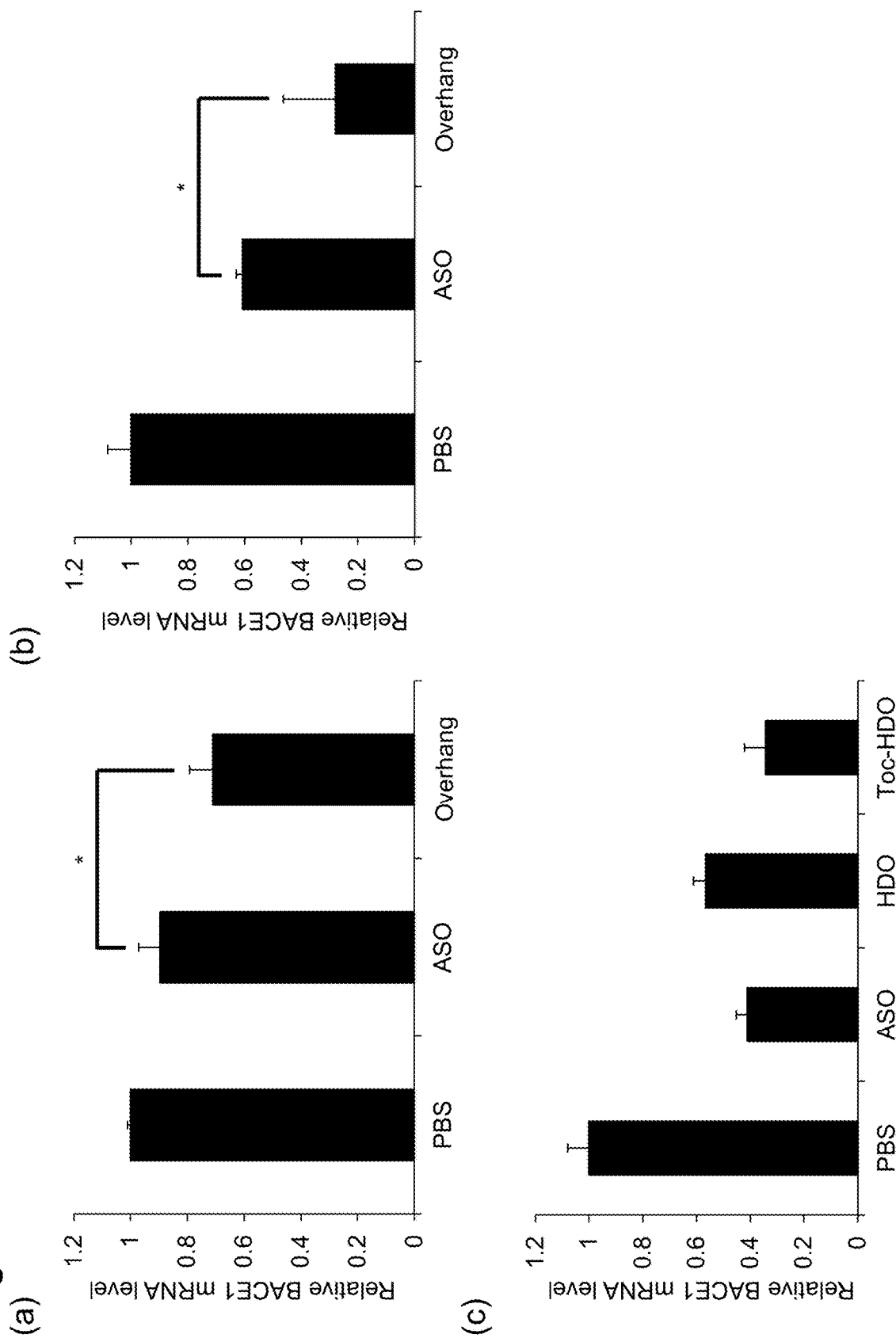
FIG. 26 shows graphs showing the result of an experiment described in Example 12, comparing the inhibitory effects on the expression of a target gene (BACE1) by a nucleic acid complex according to a particular embodiment, intraventricularly administered at a dose of (a) 6 μmol or (b and c) 12 μmol per mouse. The single asterisk (*) indicates p<0.05.

The result of Example 12 is shown in the graph of FIG. 26. The inhibition degrees obtained by the double-stranded agent according to an embodiment of the present invention ("Overhang") at both doses of 6 μmol (FIG. 26a) and 12 μmol (FIG. 26b) per mouse were larger than those obtained by the single-stranded ASO, and the differences were statistically significant. Additionally, the inhibition degrees obtained by the "HDO" and the "Toc-HDO" at a dose of 12 μmol per mouse, both of which have no overhang region, were comparable to that obtained by the single-stranded ASO (FIG. 26c).

This result indicated that the nucleic acid complex according to the present invention is efficiently delivered into the living body not only by intravenous administration but also by intraventricular administration and produce an antisense effect, and also indicated that the nucleic acid complex according to the present invention can produce an effect superior to that of conventionally known double-stranded agents.

Example 13

Figure 27:
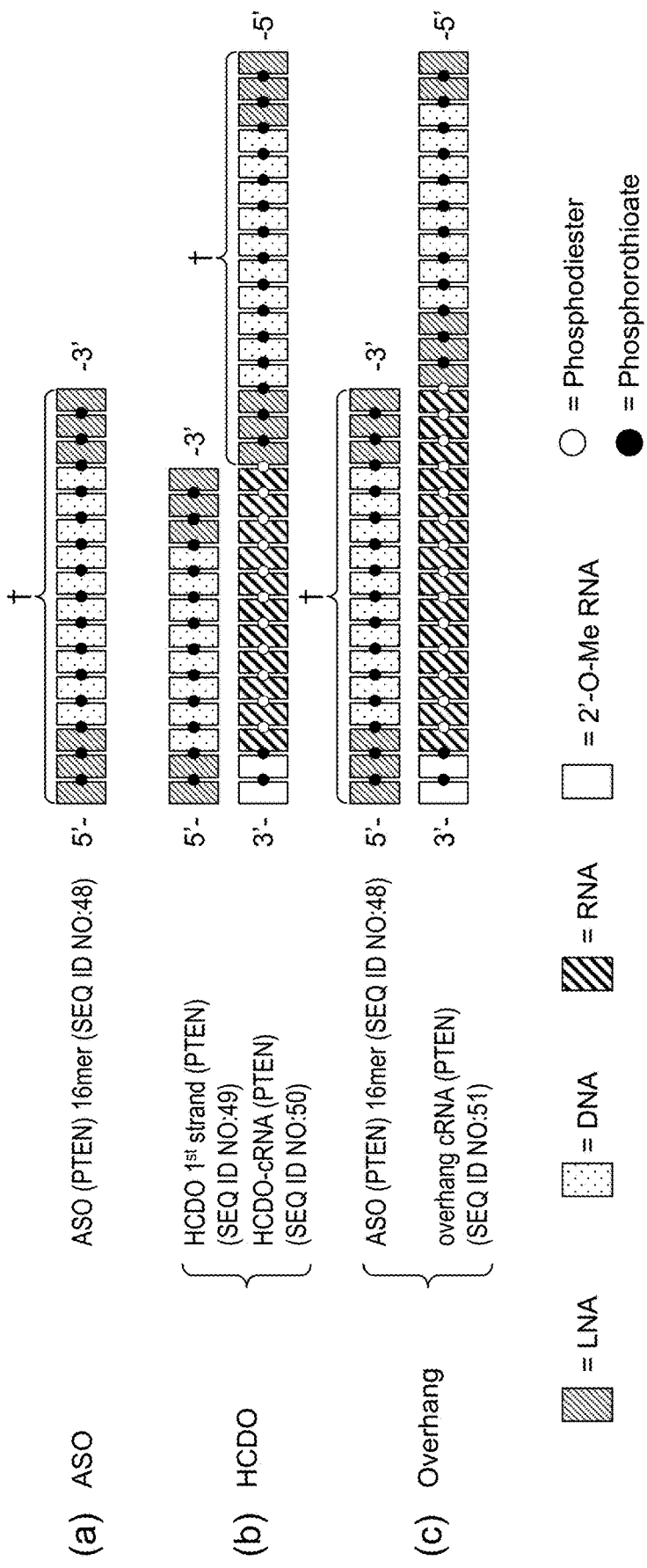
FIG. 27 shows a schematic diagram of the structures of nucleic acids used in Example 13. For each nucleic acid, the name of the nucleic acid, the name of each oligonucleotide, and the structure are shown in this order from left to right. The dagger "†" indicates a polynucleotide region of the same base sequence having an antisense effect.

The usefulness of a double-stranded nucleic acid agent according to an embodiment of the present invention targeting the mRNA of PTEN (phosphatase and tensin homolog deleted from chromosome 10), which is different from target genes used in Examples 1 to 12, was compared to that of an embodiment of the invention described in International Publication No. WO2014/192310 in an in vivo experiment and tested. The control (ASO) was a 16-mer single-stranded LNA/DNA gapmer. The LNA/DNA gapmer comprises three and three LNA nucleosides at the 5' and 3' ends, respectively, and in-between ten DNA nucleosides. The LNA/DNA gapmer is complementary to the mouse PTEN mRNA (SEQ ID NO: 6) from positions 59 to 74. The LNA/DNA gapmer (first strand) was annealed to a complementary (second strand) to prepare a double-stranded agent ("Overhang"). Additionally, a "HCDO" was prepared, which has a duplex nucleic acid structure of 13 bases in length located on the 3' terminal side of a sequence complementary to the mouse PTEN mRNA (SEQ ID NO: 6) from positions 59 to 74. The "HCDO" is an embodiment of the invention described in International Publication No. WO2014/192310. The sequences, chemical modifications, and structures of the polynucleotides used in Example 13 are shown in Table 1 and FIG. 27. The double-stranded agents were prepared similarly to Example 1.

(In Vivo Experiment)

Each nucleic acid agent was injected intravenously at a dose of 5.89 nmol/kg to mice (n=5) via tail vein. Mice used and a method of analyzing RNA expression are as described in Example 1, except for the primers used for quantitative RT-PCR to quantify PTEN mRNA.

(Result)

Figure 28:
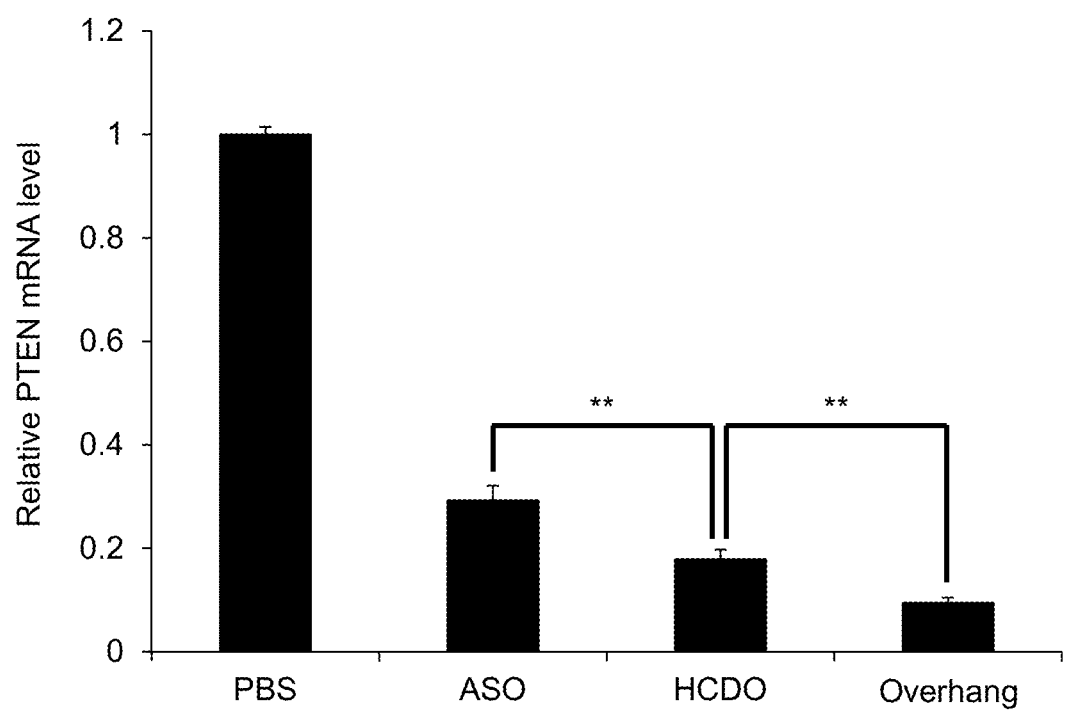
FIG. 28 shows a graph showing the result of an experiment described in Example 13, comparing the inhibitory effects on the expression of a target gene (PTEN) by a nucleic acid complex according to a particular embodiment. The double asterisk (**) indicates p<0.01.

The result of Example 13 is shown in the graph of FIG. 28. The degree of PTEN mRNA inhibition obtained by the double-stranded agent having an overhang region according to an embodiment of the present invention ("Overhang") was larger than those obtained by the "ASO" and the "HCDO," and the differences were statistically significant.

This result indicated that the nucleic acid complex according to the present invention can produce an effect superior to that of conventionally known double-stranded agents.

Example 14

Figure 29:
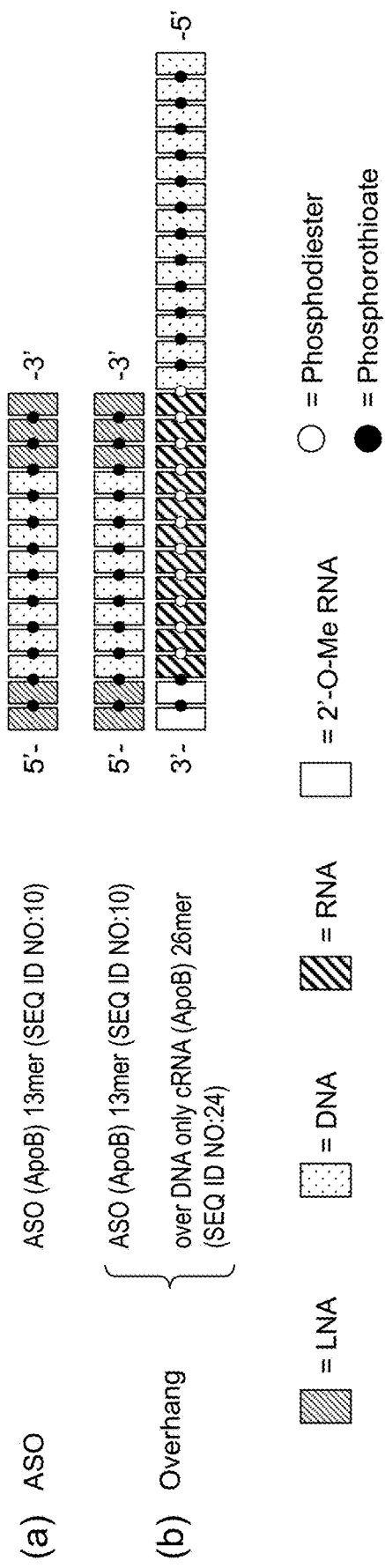
FIG. 29 shows a schematic diagram of the structures of nucleic acids used in Example 14. For each nucleic acid, the name of the nucleic acid, the name of each oligonucleotide, and the structure are shown in this order from left to right.

The usefulness of a subcutaneously administered double-stranded nucleic acid agent according to an embodiment was tested by an in vivo experiment. The target was ApoB mRNA, similarly to Examples 1 to 6. The control (ASO) was also the same single-stranded LNA/DNA gapmer as in Examples 1 to 6. The LNA/DNA gapmer (first strand) was annealed to a different complementary strand (second strand) to prepare a double-stranded agent ("Overhang"). The overhang region of the double-stranded agent has 13 DNA nucleosides. The sequences, chemical modifications, and structures of the polynucleotides used in Example 14 are shown in Table 1 and FIG. 29. The double-stranded agent was prepared similarly to Example 1.

(In Vivo Experiment)

Each nucleic acid agent was administered at a dose of 0.173 mol/kg to mice (n=4) by subcutaneous injection. Mice used and a method of analyzing ApoB mRNA expression are as described in Example 1.

(Result)

Figure 30:
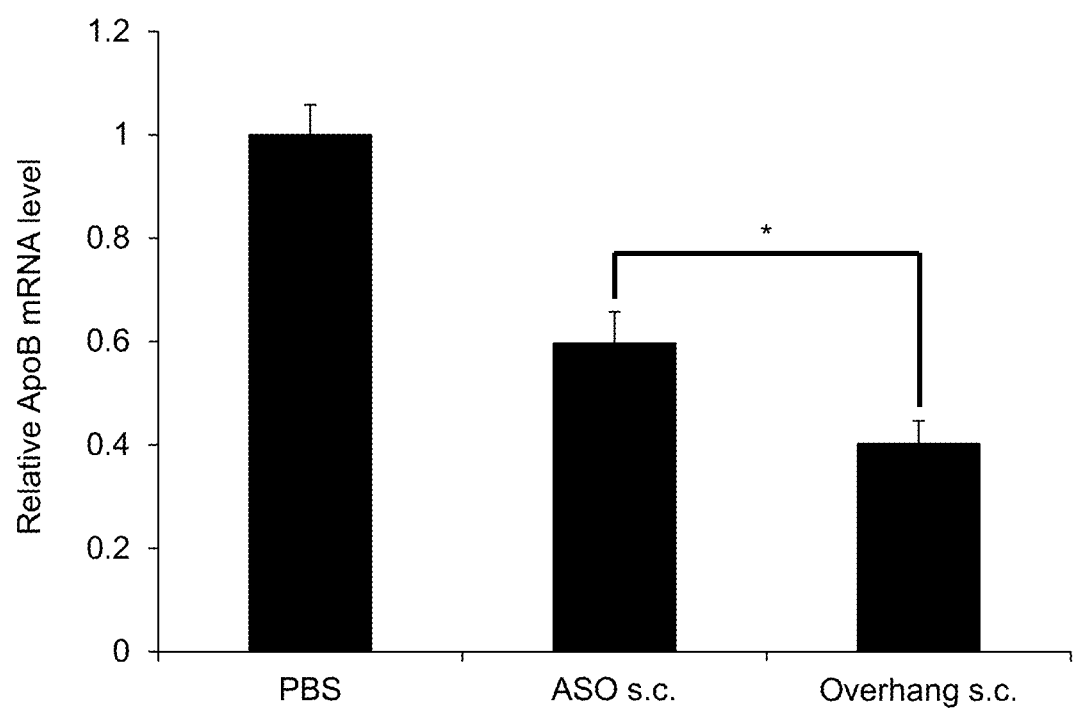
FIG. 30 shows a graph showing the result of an experiment described in Example 14, comparing the inhibitory effects on the expression of a target gene (ApoB) by subcutaneous administration of a nucleic acid complex according to a particular embodiment. The single asterisk (*) indicates p<0.05.

The result of Example 14 is shown in the graph of FIG. 30. An inhibition of ApoB mRNA expression was indicated in the both groups treated with the two nucleic acid agents, as compared to the negative control (PBS alone). The inhibition degree obtained by the double-stranded agent "Overhang" was larger than that obtained by the single-stranded ASO, and the difference was statistically significant.

This result indicated that the nucleic acid complex according to the present invention is efficiently delivered into the living body even by subcutaneous administration and produces an antisense effect.

Example 15

The usefulness of a double-stranded nucleic acid agent according to an embodiment of the present invention in a target organ (kidney), which is different from those in Examples 1 to 14, was tested by an in vivo experiment. The target RNA was PTEN mRNA, similarly to Example 13. The same single-stranded control ("ASO") and double-stranded agent ("Overhang") as in Example 13 were used. The double-stranded agent was prepared similarly to Example 1.
(In Vivo Experiment)

Each nucleic acid agent was injected intravenously at a dose of 5.65 µmol/kg to mice (n=4) via tail vein. Seventy-two hours after the injection, the mice were perfused with PBS and then dissected to isolate the kidney. Mice used and a method of analyzing RNA expression are as described in Example 1, except for the primers used for quantitative RT-PCR to quantify PTEN mRNA.
(Result)

Figure 31:
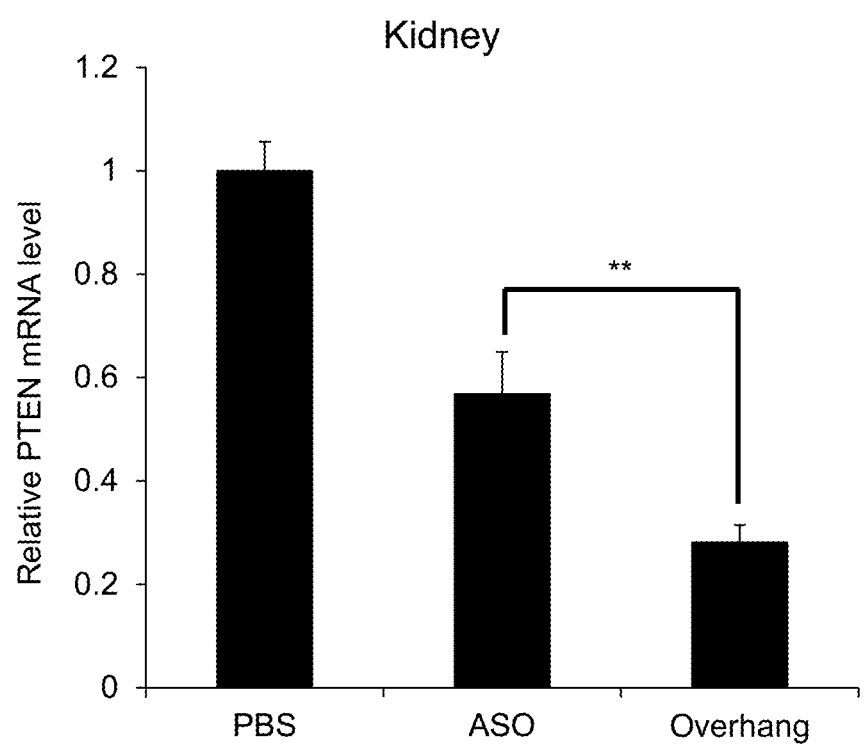
FIG. 31 shows a graph showing the result of an experiment in the kidney described in Example 15, comparing the inhibitory effects on the expression of a target gene (PTEN) by a nucleic acid complex according to a particular embodiment. The double asterisk (**) indicates p<0.01.

The result of Example 15 is shown in the graph of FIG. 31. The degree of PTEN mRNA inhibition obtained by the double-stranded agent according to an embodiment of the present invention ("Overhang") was larger than that obtained by the "ASO," and the difference was statistically significant.

This result indicated that the nucleic acid complex according to the present invention can produce an antisense effect superior to that of the single-stranded ASO even in the kidney.

Example 16

The usefulness of a double-stranded nucleic acid agent according to an embodiment of the present invention in a target organ or tissue (adrenal gland, skeletal muscle, and lung), which is different from those in Examples 1 to 15, was tested by an in vivo experiment. The target RNA was SRB1 mRNA, similarly to Example 7. The same single-stranded control (ASO) and double-stranded agent (Overhang 26-mer; see FIG. 17b) as in Example 7 were used. The double-stranded agent was prepared similarly to Example 1.
(In Vivo Experiment)

Each nucleic acid agent was injected intravenously at a dose of 7.02 µmol/kg to mice (n=4) via tail vein. Seventy-two hours after the injection, the mice were perfused with PBS and then dissected to isolate the left adrenal gland, quadriceps muscle of the left thigh (skeletal muscle), and the left lung. Mice used and a method of analyzing RNA expression are as described in Example 1, except for the primers used for quantitative RT-PCR to quantify SRB1 mRNA.
(Result)

Figure 32:
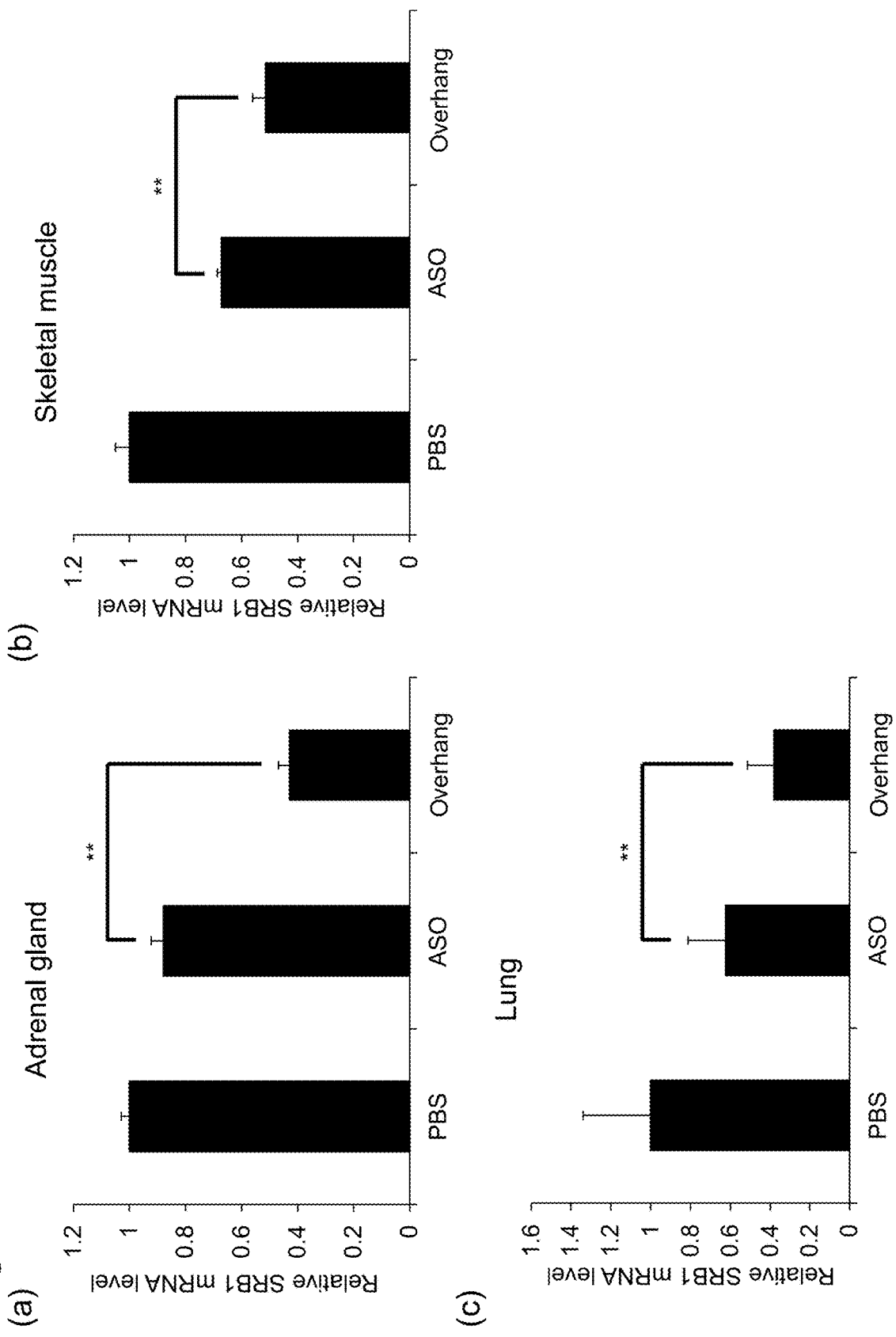
FIG. 32 shows graphs showing the results of an experiment described in Example 16, comparing the inhibitory effects on the expression of a target gene (SRB1) by a nucleic acid complex according to a particular embodiment. The double asterisk (**) indicates p<0.01. The results of the experiment in (a) the adrenal gland, (b) the skeletal muscle, and (c) the lung are shown.

The result of Example 16 is shown in the graph of FIG. 32. The degrees of SRB1 mRNA inhibition obtained by the double-stranded agent according to an embodiment of the present invention ("Overhang") were larger than those obtained by the "ASO," and the differences were statistically significant.

This result indicated that the nucleic acid complex according to the present invention can produce an antisense effect superior to that of the single-stranded ASO even in the adrenal gland, the muscle, and the lung.

All publications, patents, and patent applications cited herein are incorporated herein by reference in their entirety.

The invention claimed is:

1. A nucleic acid complex comprising a first nucleic acid strand and a second nucleic acid strand,
   wherein the first nucleic acid strand comprises a base sequence that is capable of hybridizing with at least part of a target transcription product;
   wherein the first nucleic acid strand has an antisense effect on the target transcription product;
   wherein the first nucleic acid strand is 13 to 20 bases in length;
   wherein the second nucleic acid strand comprises a complementary region comprising a base sequence complementary to the first nucleic acid strand and at least one overhang region located on the 5' terminal and/or 3' terminal side of the complementary region;
   wherein the overhang region in the second nucleic acid strand does not have an ability to substantially hybridize to transcription products in a cell and does not influence gene expression;
   wherein the first nucleic acid strand is annealed to the complementary region in the second nucleic acid strand, and
   wherein the first nucleic acid strand comprises a peptide nucleic acid and/or a morpholino nucleic acid.

2. The nucleic acid complex according to claim 1, wherein the second nucleic acid strand further comprises a functional moiety having a function selected from a labeling function, a purification function, and a target delivery function.

3. The nucleic acid complex according to claim 1, wherein the complementary region in the second nucleic acid strand does not comprise at least two consecutive ribonucleosides.

4. A nucleic acid complex comprising a first nucleic acid strand and a second nucleic acid strand,
   wherein the first nucleic acid strand comprises a base sequence that is capable of hybridizing with at least part of a target transcription product;
   wherein the first nucleic acid strand has an antisense effect on the target transcription product;
   wherein the first nucleic acid strand is 13 to 20 bases in length;
   wherein the second nucleic acid strand comprises a complementary region comprising a base sequence complementary to the first nucleic acid strand and at least one overhang region located on the 5' terminal and/or 3' terminal side of the complementary region;
   wherein the overhang region in the second nucleic acid strand does not have an ability to substantially hybridize to transcription products in a cell and does not influence gene expression;
   wherein the first nucleic acid strand is annealed to the complementary region in the second nucleic acid strand, and
   wherein the overhang region in the second nucleic acid strand comprises a modified nucleoside comprising a bicyclic sugar and is at least bases in length.

5. The nucleic acid complex according to claim 1, wherein the overhang region in the second nucleic acid strand does not comprise a modified nucleoside comprising a bicyclic sugar and is 9 to 17 bases in length.

6. A composition comprising the nucleic acid complex according to claim 1, and a pharmaceutically acceptable carrier.

7. The composition according to claim 6, wherein the composition is for intravenous administration, intraventricular administration, intrathecal administration, intramuscular injection administration, continuous infusion administration, intraperitoneal administration, inhalation, skin patch, or subcutaneous administration.

8. The nucleic acid complex according to claim 4, wherein at least one internucleoside linkage from the free end of the overhang region in the second nucleic acid strand is a modified internucleoside linkage.

9. The nucleic acid complex according to claim 4, wherein at least 50% of the internucleoside linkages within the overhang region in the second nucleic acid strand are modified internucleoside linkages.

10. The nucleic acid complex according to claim 9, wherein the modified internucleoside linkage is a phosphorothioate linkage.

11. The nucleic acid complex according to claim 1, wherein at least one nucleoside from the free end of the overhang region in the second nucleic acid strand is a modified nucleoside.

12. The nucleic acid complex according to claim 11, wherein the modified nucleoside comprises a bicyclic sugar.

* * * * *

UNITED STATES PATENT AND TRADEMARK OFFICE
CERTIFICATE OF CORRECTION

PATENT NO. : 11,260,134 B2
APPLICATION NO. : 16/337808
DATED : March 1, 2022
INVENTOR(S) : Takanori Yokota and Kotaro Yoshioka It is certified that error appears in the above-identified patent and that said Letters Patent is hereby corrected as shown below:

In the Claims

Column 131 Line 42-Column 132 Line 22, Claim 4 should read:
A nucleic acid complex comprising a first nucleic acid strand and a second nucleic acid strand,
    wherein the first nucleic acid strand comprises a base sequence that is capable of hybridizing with at least part of a target transcription product;
    wherein the first nucleic acid strand has an antisense effect on the target transcription product;
    wherein the first nucleic acid strand is 13 to 20 bases in length;
    wherein the second nucleic acid strand comprises a complementary region comprising a base sequence complementary to the first nucleic acid strand and at least one overhang region located on the 5' terminal and/or 3' terminal side of the complementary region;
    wherein the overhang region in the second nucleic acid strand does not have an ability to substantially hybridize to transcription products in a cell and does not influence gene expression;
    wherein the first nucleic acid strand is annealed to the complementary region in the second nucleic acid strand, and
wherein the overhang region in the second nucleic acid strand comprises a modified nucleoside comprising a bicyclic sugar and is at least 9 bases in length.

Signed and Sealed this
Twenty-first Day of June, 2022

Katherine Kelly Vidal
*Director of the United States Patent and Trademark Office*

SEQUENCE LISTING

```
<160> NUMBER OF SEQ ID NOS: 56

<210> SEQ ID NO 1
<211> LENGTH: 13931
<212> TYPE: DNA
<213> ORGANISM: Mus musculus

<400> SEQUENCE: 1
tacctgcctg agctccgcct ccgaagaccc tgtagagcaa gcagcagggg ctaggcccgt      60
ggccaggcca cagccaggaa gccacccac  catccatccg ccatgggccc acgaaagcct     120
gccctgcgga cgccgttact gctgctgttc ctgctactgt tcttggacac cagcgtctgg     180
gctcaagatg aagtcctgga aaacttaagc ttcagctgtc caaaagatgc aactcgattc     240
aagcacctcc gaaagtacgt gtacaactat gaagctgaaa gttccagcgg tgtccagggc     300
acagctgact ccagaagcgc caccaagatc aactgtaagg tagagctgga ggtcccccaa     360
atctgtggtt tcatcatgag gaccaaccag tgtaccctta aagaggtgta tggcttcaac     420
cctgagggca aggccttgat gaagaaaacc aagaactctg aagagtttgc agctgccatg     480
tccaggtacg aactcaagct ggccattcct gaagggaaac aaattgttct ttaccctgac     540
aaggatgaac ctaaatatat cctgaacatc aagaggggca tcatctctgc tcttctggtt     600
cccccagaga cagaagagga ccaacaagag ttgttcctgg ataccgtgta tggaaactgc     660
tcaactcagg ttaccgtgaa ttcagaaaag ggaaccgtac caacagaaat gtccacagag     720
agaaacctgc agcaatgtga cggcttccag cccatcagta caagtgtcag ccctctcgct     780
ctcatcaaag gcctggtcca ccccttgtca actcttatca gcagcagcca aacttgccag     840 tacacccctgg atcctaagag gaagcatgtg tctgaagctg tctgtgatga gcagcatctt     900
ttcctgcctt tctcctacaa gaataagtat gggatcatga cacgtgttac acagaaactg     960
```

```
agtcttgaag acacacctaa gatcaacagt cgcttcttca gtgaaggtac caaccggatg      1020
ggtctggcct ttgagagcac caagtccacg tcatccccaa agcaggctga tgctgttttg      1080
aagacccttc aagaactgaa aaaattgtcc atctcagagc agaatgctca gagagcaaat      1140
ctcttcaata aactggttac tgagctgaga ggcctcactg gtgaagcaat cacatccctc      1200
ttgccacagc tgattgaagt gtccagcccc atcactttac aagccttggt tcagtgtgga      1260
cagccacagt gctatactca catcctccag tggctgaaaa ctgagaaggc tcaccccctc      1320
ctggttgaca ttgtcaccta cctgatggct ctgatcccaa atccctcaac acagaggctg      1380
caggaaatct ttaatactgc caaggagcag cagagccgag ccactctgta tgcactgagc      1440
cacgcagtta acagctattt tgatgtggac cattcaagga gcccagttct gcaggatatc      1500
gctggttacc tgttgaaaca gatcgacaat gaatgcacgg gcaatgaaga ccacaccttc      1560
ttgattctga gggtcattgg aaatatggga agaaccatgg aacaagtaat gccagccctc      1620
aagtcctcag tcctgagctg tgtacgaagt acaaaaccat ctctgctgat tcagaaagct      1680
gctctccagg ccctgaggaa gatggaactg gaagatgagg tccggacgat ccttttttgat      1740 acatttgtaa atggtgtcgc tcccgtggag aagagactgg ctgcctatct cttgctgatg      1800 aagaacccctt cctcatcaga tattaacaaa attgcccaac ttctccaatg ggaacagagt      1860
gagcaggtga agaacttcgt ggcatctcac attgccaaca tcttgaactc ggaagaactg      1920
tatgtccaag atctgaaagt tttgatcaaa aatgctctgg agaattctca atttccaacg      1980
atcatggact tcagaaaatt ttcccgaaac tatcagattt ccaaatctgc ttctctccca      2040
atgttcgacc cagtctcagt caaaatagaa gggaatctta tatttgatcc aagcagttat      2100
cttcccagag aaagcttgct gaaaacaacc ctcacagtct ttggacttgc ttcacttgat      2160
ctctttgaga ttggtttaga aggaaaaggg tttgagccaa cactagaagc tcttttttggt      2220 aagcaaggat tcttcccaga cagtgtcaac aaggctttgt attgggtcaa tggccgagtt      2280
ccagatggtg tctccaaggt cttggtggac cactttggct atactacaga tggcaagcat      2340
gaacaggaca tggtgaatgg aatcatgccc attgtggaca agttgatcaa agatctgaaa      2400
tctaaagaaa ttcctgaagc cagggcctat ctccgcatcc taggaaaaga gctaagcttt      2460
gtcagactcc aagacctcca agtcctgggg aagctgttgc tgagtggtgc acaaactttg      2520
cagggaatcc cccagatggt tgtacaggcc atcagagaag ggtcaaagaa tgacttgttt      2580
ctccactaca tcttcatgga caatgccttt gagctcccca ctggagcagg ttacagctg       2640 caagtgtcct cgtctggagt cttcacccccc gggatcaagg ctggtgtaag actggaatta      2700
gccaacatac aggcagagct agtggcaaag ccctctgtgt ccttggagtt tgtgacaaat      2760
atgggcatca tcatcccaga cttcgctaag agcagtgtcc agatgaacac caacttcttc      2820
cacgagtcag gcctggaggc gcgagtggcc ctgaaggctg ggcagctgaa ggtcatcatt      2880
ccttctccaa agaggccagt caagctgttc agtggcagca acacactgca tctggtctct      2940
accaccaaaa cagaagtgat cccacctctg gttgagaaca ggcagtcctg gtcaacttgc      3000
aagcctctct tcactggaat gaactactgt accacaggag cttactccaa cgccagctcc      3060
acggagtctg cctcttacta cccactgaca ggggacacaa ggtatgagct ggagctgagg      3120
cccacgggag aagtggagca gtattctgcc actgcaacct atgaactcct aaaagaggac      3180
aagtctttgg ttgacacatt gaagttccta gttcaagcag aaggagtgca gcagtctgaa      3240
gctactgtac tgttcaaata taatcggaga agcaggacct tatctagtga agtcctaatt      3300
ccagggtttg atgtcaactt cgggacaata ctaagagtta atgatgaatc tgctaaggac      3360
```

```
aaaaacactt acaaactcat cctggacatt cagaacaaga aaatcactga ggtctctctc    3420
gtgggccact tgagttatga taaaaaggga gatggcaaga tcaaaggtgt tgtttccata    3480
ccacgtttgc aagcagaagc caggagtgag gtccacaccc actggtcctc caccaaactg    3540
ctcttccaaa tggactcatc tgctacagct tacggctcaa caatttccaa gagagtgaca    3600
tggcgttacg ataatgagat aatagaattt gattggaaca cgggaaccaa tgtggatacc    3660 aaaaagtgg cctccaattt ccctgtggat ctttcccatt atcctagaat gttgcatgag    3720
tatgccaatg gtctcctgga tcacagagtc cctcaaacag atgtgacttt tcgggacatg    3780
ggttccaaat taattgttgc aacaaacaca tggcttcaga tggcaaccag ggtcttcct    3840 taccccaaa ctctacagga tcacctcaat agcctctcag agttgaacct cctgaaaatg    3900
ggactgtctg acttccatat tccagacaac ctcttcctaa agactgatgg cagagtcaaa    3960
tacacaatga acaggaacaa aataaacatt gacatccctt gcctttgggg tggcaagtct    4020
tcaaaagacc tcaagatgcc agagagtgtg aggacaccag ccctcaactt caagtctgtg    4080
ggattccatc tgccatctcg agaggtccag gtccccactt ttacaatccc caagacacat    4140
cagcttcaag tgcctctctt gggtgttcta gacctttcca caaatgtcta cagcaatttg    4200
tacaactggt cagcctccta cactggtggc aacaccagca gagaccactt cagccttcag    4260
gctcagtacc gcatgaagac tgactctgtg gttgacctgt tttcctacag tgtgcaagga    4320
tctggagaaa caacatatga cagcaagaac acatttacat tgtcctgtga tggatctcta    4380
caccataaat ttctagactc aaaattcaaa gtcagccacg tagaaaaatt tggaaacagc    4440
ccagtctcaa aaggtttact aacatttgaa acatctagtg ccttgggacc acagatgtct    4500
gctactgttc acctagactc aaaaaagaaa caacatctat acgtcaaaga tatcaaggtt    4560
gatggacagt tcagagcttc ttcatttat gctcaaggca aatatggcct gtcttgtgag    4620
agagatgtta caactggcca gctgagcggc gaatccaaca tgagatttaa ctccacctac    4680
ttccagggca ccaaccagat cgtgggaatg taccaggatg gagccctgtc catcacctcc    4740
acttctgacc tgcaagatgg catattcaag aacacagctt ccttgaaata tgaaaactat    4800
gagctgactc tgaaatctga tagcagtggg cagtatgaga acttcgctgc ttccaacaag    4860
ctggatgtga ccttctctac gcaaagtgca ctgctgcgtt ctgaacacca ggccaattac    4920
aagtccctga ggcttgtcac ccttctttca ggatccctca cttcccaggg tgtagaatta    4980
aatgctgaca tcttgggcac agacaaaatt aatactggtg ctcacaaggc aacactaaag    5040
attgcacgtg atggactatc aaccagtgcg accaccaact gaagtacag ccccctgctg    5100 ctggagaatg agttgaatgc agagcttggg ctctctgggg catccatgaa attatcaaca    5160 aacgccgct tcaagaacca ccatgcaaaa ttcagtcttg atgggagagc tgccctcaca    5220
gaggtgtcac tggggagcat ttaccaggcc atgattctgg gtgcagacag caaaaacatc    5280
ttcaacttca aactcagccg agaagggctg aggctgtcca atgatttgat gggctcctat    5340
gctgagatga acttgaccaa cacacacagt ctgaacattg caggtctctc actggacttc    5400
ttctcaaaaa tggacaatat ttacagtgga gacaagttct ataagcagaa tttttaactta    5460 cagctacagc cctattcttt cataactact ttaagcaacg acctgagata tggtgctcta    5520
gatttgacca acaatggaag gtttcggctg agccactga agctgaatgt gggtggcaac    5580
tttaaaggaa cctatcaaaa taatgagctg aaacatatct ataccatatc ttatactgac    5640
ctggtagtag caagttacag agcagacact gtggctaagg ttcagggtgt cgaattcagc    5700
```

```
cataggctaa atgcagacat tgaaggactg acttcctctg ttgatgtcac taccagctac    5760
aattcagatc cactgcattt taacaatgtt ttccactttt ctctggcacc ttttaccttg    5820
ggcatcgaca cacatacaag tggtgatggg aaactgtcct tctggggaga acacactggg    5880
cagctatata gtaagtttct gttgaaagca gaacctctgg cacttattgt ctctcatgac    5940
tacaaaggat ccacaagcca cagtctcccg tacgagagca gcatcagcac ggctcttgaa    6000
cacacagtca gtgccttgct gacgccagct gagcagacaa gcacctggaa attcaagacc    6060
aaactgaatg acaaagtata cagccaggac tttgaagcct acaacactaa agacaaaatc    6120
ggtgttgagc ttagtggacg ggctgacctc tctgggctgt attctccaat taaactaccg    6180
tttttctaca gtgagcctgt caatgtcctt aatggcttag aggtaaatga tgctgttgac    6240
aagccccaag aattcacaat tattgctgtg gtgaagtacg ataagaacca ggatgttcac    6300
accatcaacc tcccattctt caaaagcctg ccagactatt ggagagaaa tcgaagagga    6360 atgataagtc tactggaagc catgcgaggg gaattgcaac gcctcagtgt tgatcagttt    6420
gtgaggaaat acagagcggc cctgagcaga cttcctcagc agattcatca ttatctgaat    6480
gcatctgact gggagagaca agtagctggt gccaaggaaa aaataacttc tttcatggaa    6540
aattatagaa ttacagataa tgatgtacta attgccatag atagtgccaa aatcaacttc    6600
aatgaaaaac tctctcaact tgagacatac gcgatacaat ttgatcagta tattaaagat    6660
aattatgatc cacatgactt aaaaagaact attgctgaga ttattgatcg aatcattgaa    6720
aagttaaaaa ttcttgatga acagtatcat atccgtgtaa atctagcaaa atcaatccat    6780
aatctctatt tatttgttga aacgttgat cttaaccaag tcagtagtag taacacctct    6840
tggatccaaa atgtggattc caattatcaa gtcagaatcc aaattcaaga aaaactacag    6900
cagctcagga cacaaattca gaatatagac attcagcagc ttgctgcaga ggtaaaacga    6960
cagatggacg ctattgatgt cacaatgcat ttagatcaat tgagaactgc aattctattc    7020
caaagaataa gtgacattat tgaccgtgtc aaatactttg ttatgaatct tattgaagat    7080
tttaaagtaa ctgagaaaat caatactttt agagttatag tccgtgagct aattgagaaa    7140
tatgaagtag accaacacat ccaggtttta atggataaat cagtagagtt ggcccacaga    7200
tatagcctga gcgagcctct tcagaaactc agtaatgtgc tacagcgaat tgagataaaa    7260
gattactatg agaaattggt tgggtttatt gatgatactg ttgagtggct taaagcattg    7320
tctttcaaaa ataccattga agaactaaat agattgactg acatgttggt gaagaagttg    7380
aaagcatttg attatcacca gtttgtagac aaaaccaaca gcaaaatccg tgagatgact    7440
cagagaatca atgctgaaat ccaagctctc aaacttccac aaaaaatgga agcattaaaa    7500
ctgttggtag aagacttcaa aaccacagtc tccaattccc tggaaagact caaggacacc    7560
aaagtaactg tggtcattga ttggctgcag gatattttga ctcaaatgaa agaccatttc    7620
caagatactc tggaagatgt aagagaccga atttatcaaa tggacattca gagggaactg    7680
gagcacttct tgtctctggt aaaccaagtt tacagtacac tggtcaccta tatgtctgac    7740
tggtggactc tgactgctaa aaacataaca gactttgcag agcaatattc catccaaaac    7800
tgggctgaga gtataaaagt actggtggaa caaggattca tagttcctga aatgcaaaca    7860
tttctgtgga ccatgcctgc ttttgaggtc agtctccgtg ctctccaaga aggtaacttt    7920 cagaccctg tctttatagt cccttgaca gatttgagga ttccatcaat tcggataaac    7980
tttaaaatgt taaagaatat aaaaatccca ttgagatttt ccactccaga attcactctt    8040
ctcaacacct tccatgtcca ttcctttaca attgacttgc tggaaataaa agcaaagatc    8100
```

```
attagaacta tcgaccaaat tttgagcagt gagctacagt ggcctcttcc agaaatgtat   8160
ttgagagacc tggatgtagt gaacattcct cttgcaagac tgactctgcc agacttccat   8220
gtaccagaaa tcacaattcc agaattcaca atcccaaatg tcaatctcaa agatttacac   8280
gttcctgatc ttcacatacc agaattccaa cttcctcacc tctcacatac aattgaaata   8340
cctgcttttg gcaaactgca tagcatcctt aagatccaat ctcctctctt tatattagat   8400
gctaatgcca acatacagaa tgtaacaact tcagggaaca aagcagagat tgtggcttct   8460
gtcactgcta aaggagagtc ccaatttgaa gctctcaatt ttgattttca agcacaagct   8520
caattcctgg agttaaatcc tcatcctcca gtcctgaagg aatccatgaa cttctccagt   8580
aagcatgtga aatggagca tgagggtgag atagtatttg atggaaaggc cattgagggg   8640
aaatcagaca cagtcgcaag tttacacaca gagaaaaatg aagtagagtt taataatggt   8700
atgactgtca aagtaaacaa tcagctcacc cttgacagtc acacaaagta cttccacaag   8760
ttgagtgttc ctaggctgga cttctccagt aaggcttctc ttaataatga aatcaagaca   8820
ctattagaag ctggacatgt ggcattgaca tcttcaggga cagggtcatg gaactgggcc   8880
tgtcccaact tctcggatga aggcatacat tcgtcccaaa ttagctttac tgtggatggt   8940
cccattgctt ttgttggact atccaataac ataaatggca aacacttacg ggtcatccaa   9000
aaactgactt atgaatctgg cttcctcaac tattctaagt ttgaagttga gtcaaaagtt   9060
gaatctcagc acgtgggctc cagcattcta acagccaatg gtcgggcact gctcaaggac   9120
gcaaaggcag aaatgactgg tgagcacaat gccaacttaa atggaaaagt tattggaact   9180
ttgaaaaatt ctctcttctt ttcagcacaa ccatttgaga ttactgcatc cacaaataat   9240
gaaggaaatt tgaaagtggg ttttccacta aagctgactg ggaaaataga cttcctgaat   9300
aactatgcat tgtttctgag tccccgtgcc caacaagcaa gctggcaagc gagtaccaga   9360
ttcaatcagt acaaatacaa tcaaaacttt tctgctataa acaatgaaca caacatagaa   9420
gccagtatag aatgaatgg agatgccaac ctggatttct taaacatacc tttaacaatt   9480
cctgaaatta acttgcctta cacggagttc aaaactccct tactgaagga tttctccata   9540
tgggaagaaa caggcttgaa agaattttg aagacaacaa agcaatcatt tgatttgagt   9600
gtaaaggctc aatataaaaa gaacagtgac aagcattcca ttgttgtccc tctgggtatg   9660
ttttatgaat ttattctcaa caatgtcaat tcgtgggaca gaaaatttga gaaagtcaga   9720
aacaatgctt tacattttct taccacctcc tataatgaag caaaattaag gttgataag   9780 tacaaaactg aaaattccct taatcagccc tctgggacct tcaaaatca tggctacact   9840 atcccagttg tcaacattga agtatctcca tttgctgtag agacactggc ttccagccat   9900
gtgatcccca cagcaataag caccccaagt gtcacaatcc ctggtcctaa catcatggtg   9960
ccttcataca gttagtgct gccaccctg gagttgccag ttttccatgg tcctgggaat  10020
ctattcaagt ttttcctccc agatttcaag ggattcaaca ctattgacaa tatttatatt  10080
ccagccatgg gcaactttac ctatgacttt tcttttaaat caagtgtcat cacactgaat  10140
accaatgctg gactttataa ccaatcagat atcgttgccc atttcctttc ttcctcttca  10200
tttgtcactg acgccctgca gtacaaatta gagggaacat cacgtctgat gcgaaaaagg  10260
ggattgaaac tagccacagc tgtctctcta actaacaaat ttgtaaaggg cagtcatgac  10320
agcaccatta gttaaccaa gaaaacatg gaagcatcag tgagaacaac tgccaacctc  10380
catgctccca tattctcaat gaacttcaag caggaactta atggaaatac caagtcaaaa  10440
```

```
cccactgttt catcatccat tgaactaaac tatgacttca attcctcaaa gctgcactct    10500
actgcaacag gaggcattga tcacaagttc agcttagaaa gtctcacttc ctacttttcc    10560
attgagtcat tcaccaaagg aaatatcaag agttccttcc tttctcagga atattcagga    10620
agtgttgcca atgaagccaa tgtatatctg aattccaagg gtactcggtc ttcagtgagg    10680
ctacaaggag cttccaaagt tgatggtatc tggaacgttg aagtaggaga aaattttgct    10740
ggagaagcca ccctccaacg catctacacc acatgggagc acaatatgaa aaaccatttg    10800
caggtatata gctacttctt cacaaaagga aagcaaacat gcagagctac tttggagctc    10860
tccccatgga ccatgtcaac cttgctacag gttcatgtga gtcaactcag ttccctcctt    10920
gacctccatc actttgacca ggaagtgatc ctaaaagcta acactaagaa ccagaagatc    10980
agctggaaag gtggggtcca ggttgaatca cgggttcttc agcacaatgc acagttctcc    11040
aatgaccaag aagaaatacg gcttgacctt gcaggatcct tagacggaca gctgtgggac    11100
cttgaagcta tcttttttacc agtatatggc aagagcttgc aggaactcct acaaatggat    11160
ggaaagcgac agtatcttca agcttcaact tctcttctat ataccaaaaa ccctaatggc    11220
tatctcctct cactccccgt gcaagaactg gctgatagat ttattatacc agggataaaa    11280
ctaaatgact tcagtggagt aaaaatctat aagaagttaa gtacttcacc atttgccctc    11340
aacctaacaa tgctccccaa agtaaaattc cctgggattg atctgttaac acagtactct    11400
acaccagagg gctcctctgt ccctattttt gaggcaacta tacctgaaat tcatttaact    11460
gtatcccagt ttacacttcc aaagagccctt ccagttggca acacagtctt tgatctgaat    11520
aagttggcca acatgattgc cgatgttgac ctgcctagtg tcaccctgcc tgagcagact    11580
attgtaatcc caccttgga gttctctgta cctgctggga ttttttattcc tttctttgga    11640 gaactgactg cacgtgctgg gatggcttct ccctgtata atgtcacttg gagcgctggt    11700
tggaaaacca agcagatca tgttgaaacg ttcctagatt ccatgtgcac ttcaaccttg    11760
cagtttctgg agtatgcttt aaaagttgta gaaacacaca aaattgaaga agatctgtta    11820
acctataata tcaaaggaac acttcaacac tgtgacttca atgtggagta taatgaagat    11880
ggtctattta aaggactttg ggactggcag ggagaggctc acctggacat caccagccca    11940
gcactgactg actttcatct gtactacaaa gaagacaaga caagtctgtc tgcctcagca    12000
gcctcctcga ccatcggcac tgtgggtctg gattcgagca cagatgacca gagtgtggag    12060
ctgaatgtct acttccaccc acagtcccct ccagagaaga aactcagcat attcaaaact    12120
gagtggaggt acaaggagtc tgatggtgaa aggtacatca aaattaattg ggaagaagag    12180
gcagcttcca gattgctagg ctccctaaaa agcaatgtgc ccaaggcttc taaggctatt    12240
tatgattatg ccaataagta ccacctggaa tacgtttctt cagaactaag aaaaagtcta    12300
caggtcaatg ctgaacatgc cagaaggatg gttgatgaaa tgaacatgag tttccagaga    12360
gtagcccgtg atacctacca gaatctctat gaggagatgt tggctcagaa gagcctgagc    12420
atccctgaga atctcaagaa gagggtgtta gacagtatag tacatgttac tcagaagtac    12480
cacatggcag tcatgtggct gatggactca ttcattcatt ttctgaaatt caatagagtc    12540
cagttcccag ggtacgctgg aacatatact gtggacgaac tctacactat agtcatgaag    12600
gaaaccaaga agtcactgtc tcagctgttt aatgggttag gaaacctact ttcctacgtt    12660
caaaaccaag tagagaaatc aagattaatc aatgacataa catttaaatg tccttttttc    12720
tcaaaacctt gtaaactaaa agatctcata ttgattttca gggaggagtt aaacatttta    12780
tcaaacatag gccaacagga tatcaagttt acaacaatac taagtagtct tcagggcttt    12840
```

```
ttggagagag ttttagacat catagaagaa caaattaaat gcctaaagga caatgaatct    12900
acttgtgttg ctgaccatat caacatggtt ttcaaaatac aggtcccata tgcttttaaa    12960
tccctaagag aagacatata ctttgtcctc ggtgagttca atgactttct tcaatccata    13020
cttcaggagg ggtcctacaa gctacagcag gtccatcagt atatgaaggc ccttcgtgaa    13080
gagtattttg atccgagcat ggttgggtgg acagtgaaat attatgaaat agaagaaaat    13140
atggttgagc tgatcaagac cctttagtt tcctttaggg atgtctactc tgaatatagt     13200
gtgacagctg ctgatttgc ttccaaaatg tcaactcaag ttgaacaatt tgtgtccagg      13260
gatatcagag agtatcttag catgcttact gatataaatg gaaagtggat ggaaaagatt    13320
gcagagcttt ctattgtggc aaaggaaaca atgaaaagct gggtcactgc cgtggccaaa    13380
ataatgtctg attacccca gcagttccac tccaatctgc aggattttc agaccaactc       13440
tctagctact atgaaaaatt tgttggtgag tccacaagat tgattgacct gtccattcaa    13500
aactaccacg tgtttctcag atacatcacc gagttactga aaagctgca ggtggccaca      13560
gccaataatg tgagcccta tataaagctt gctcaaggag agctgatgat caccttctga     13620
ttcatctact aacaaattca aattaaacct tcacatagta ggagactttg tagactacta    13680
taaagaccat cctgagccag acctgcagtc aacagcaaga gcaagaagca cataggaact    13740
atacctgcaa ccaagctggc ataagaacca agaccttcaa agcagcctga actcaagatg    13800
acatatttta caagttagag taaagtcaag agctgagttg ttttgtccaa ctcaggatgg    13860
agggagggag ggaagggaa ataaataaat acttccttat tgtgcagcaa aaaaaaaaa       13920
aaaaaaaaaa a                                                         13931

<210> SEQ ID NO 2
<211> LENGTH: 2534
<212> TYPE: DNA
<213> ORGANISM: Mus musculus

<400> SEQUENCE: 2
ggaatcccgc gccgaactcg ggggcgggct gcccgggcca tggcgcataa agcctctggc      60
cacctgcagg gctactgctg ctccggccac cgccaggcac acaccttgct gctgagggag     120
tctcggcttc tgtcatctct gtggcctccg tcacctctgt ctccgtctcc ttcaggtcct     180
gagccccgag agccccttcc gcgcacgcgg acatgggcgg cagctccagg gcgcgctggg     240
tggccttggg gttgggcgcc ctggggctgc tgtttgctgc gctcggcgtt gtcatgatcc     300
tcatggtgcc ctccctcatc aagcagcagg tgctcaagaa tgtccgcata gacccgagca    360
gcctgtcctt cgggatgtgg aaggagatcc ccgtcccttt ctacttgtct gtctacttct    420
tcgaagtggt caaccaaaac gaggtcctca acggccagaa gccagtagtc cgggagcgtg    480
gacccctatgt ctacagggag ttcagacaaa aggtcaacat caccttcaat gacaacgaca   540
ccgtgtcctt cgtggagaac cgcagcctcc atttccagcc tgacaagtcg catggctcag    600
agagtgacta cattgtactg cctaacatct tggtcctggg gggctcgata ttgatggaga    660
gcaagcctgt gagcctgaag ctgatgatga ccttggcgct ggtcaccatg gccagcgtg     720
cttttatgaa ccgcacagtt ggtgagatcc tgtgggcta tgacgatccc ttcgtgcatt     780
ttctcaacac gtacctccca gacatgcttc ccataaaggg caaatttggc ctgtttgttg    840
ggatgaacaa ctcgaattct ggggtcttca ctgtcttcac gggcgtccag aatttcagca    900
ggatccatct ggtggacaaa tggaacggac tcagcaagat cgattattgg cattcagagc    960
```

```
agtgtaacat gatcaatggg acttccgggc agatgtgggc acccttcatg acacccgaat    1020
cctcgctgga attcttcagc ccggaggcat gcaggtccat gaagctgacc tacaacgaat    1080
caagggtgtt tgaaggcatt cccacgtatc gcttcacggc ccccgatact ctgtttgcca    1140
acgggtccgt ctaccaccc aacgaaggct tctgcccatg ccgagagtct ggcattcaga     1200
atgtcagcac ctgcaggttt ggtgcgcctc tgtttctctc ccaccccac ttttacaacg     1260 ccgaccctgt gttgtcagaa gctgttcttg gtctgaaccc taacccaaag gagcattcct    1320
tgttcctaga catccatccg gtcactggga tccccatgaa ctgttctgtg aagatgcagc    1380
tgagcctcta catcaaatct gtcagggca tcgggcaaac agggaagatc gagccagtag     1440
ttctgccgtt gctgtggttc aacagagcg gagcaatggg tggcaagccc ctgagcacgt     1500
tctacacgca gctggtgctg atgccccagg ttcttcacta cgcgcagtat gtgctgctgg    1560
ggcttggagg cctcctgttg ctggtgccca tcatctgcca actgcgcagc caggagaaat    1620 gcttttttgtt ttggagtggt agtaaaaagg ctcccagga taaggaggcc attcaggcct    1680
actctgagtc cctgatgtca ccagctgcca agggcacggt gctgcaagaa gccaagctat    1740
agggtcctga agacactata agcccccaa acctgatagc ttggtcagac cagccaccca    1800
gtccctacac cccgcttctt gaggactctc tcagcggaca gcccaccagt gccatggcct    1860
gagcccccag atgtcacacc tgtccgcacg cacggcacat ggatgcccac gcatgtgcaa    1920
aaacaactca gggaccaggg acagacctgc tgccaagtga gcctgatggg ccacaggtgt    1980
gctcttctaa atggcctgtg agccaggctg tgggaactct agctgctgtc agcccctcct    2040
gtaggagctg gccctgccca ggctcctgac ttccctcagg aagtctttct gtctttctcc    2100
atcagtctga aagccttagt tcccacagag gacggatctg tcactcctag gggctgggca    2160
tatgtcggcc tcttgtgcca aggccaggca agcagctcca ggtcctgacc agtttgcaca    2220
cacactctgg agctgtatct ggcgcttttt ctatcgtctc tgctatgtca ctgaattaac    2280
cactgtacgt ggcagaggtg gcaggcccct cagggtcctt attttttcagg catgggtca    2340 aagctagagg tatgggccgt ctacacccccc ccgcccccg gcatctagtg tacctcacca   2400
gagggtattc ggaggcccag catcctgcaa ccgacccctt ttttctactg aagagaaat    2460 tttatcatct tttgaaagga agtcatgact gaagcaataa accttttcac tgattcaaca   2520
aaaaaaaaaa aaaa                                                      2534

<210> SEQ ID NO 3
<211> LENGTH: 6982
<212> TYPE: DNA
<213> ORGANISM: Mus musculus

<400> SEQUENCE: 3
aggcattcag gcagcgagag cagagcagcg tagagcagca cagctgagct cgtgaggcag      60
gagactcagc ccgaggaaat cgcagataag ttttttaatta aaaagattga gcagtaaaaa    120
gaattagaac tctaaactta agctaataga gtagcttatc gaaatattac ttagtcttaa    180
taatctaaga agatcttaag agataacatg aaggcttatt taaacagttt gaaaaaggaa    240
atgaggagaa aagtatttgt actgtataat ggaggctgac cagagcagtt taggagattg    300
taaagggagg ttttgtgaag ttctaaaagg ttctagtttg aaggtcggcc ttgtagatta    360
aaacgaaggt tacctaaata gaatctaagt ggcatttaaa acagtaaagt tgtagagaat    420
agtttgaaaa tgaggtgtag ttttaaaaga ttgagaaaag taggttaagt tgacggccgt    480
tataaaaatc cttcgactgg cgcatgtacg tttgaaggca tgagttggaa acaggaaga    540
```

```
tggaagtgtt aggctagccg ggcgatggtg gcgcacgcct ttaatcctag cacttgggag    600
gcagaggcag gcggatttct gagttcgagg ccagcctggt ctacagagtg agttccagga    660
cagccagggc tacacagaga aaccctgtct tgaaaaaaca aaaggttag gctagtattt     720 ggagaaagaa gattagaaaa tggaagtgaa agacgaagaa gacatacagg aaggtgaaga    780
aaaagctgtt agagaagata ggaaaataga agacaaagca tctttagaag acagaaaagg    840
tacttaaagg cacaggtagt aggaagccga agaatagaag atagaaagaa gcaagataga    900
aaaacaaaat ggaagttaag acaactttgg atgccagcat tcaagatagg caaagaagat    960
aagattgagg ccaaaaggtt ggataagata taaagtcaga aggaaattat ctttaaagcc   1020
ataagttcaa atttctgatg gagcgagcag tttagaagag tctttagaca gccacataca   1080
agattgaagc tagcaatcaa agctactagg actgaagtaa aaagttaagg cagaatgcct   1140
ttgaagagtt agaagaatat taaaagcctt aacttgtagc ttaattttgc ttgatgacaa   1200
aaggactttt gataacagtt tcaagattgt cagcattttg cattggactt gagctgaggt   1260
gcttttaaaa tcctaacgac tagcattggc agctgaccca ggtctacaca gaagtgcatt   1320
cagtgaacta ggaagacagg agcggcagac aggagtcccg aagccagttt ggtgaagcta   1380
ggaaggactg aggagccagc agcagcagtg catggtgaag atagcccagg aaagagtgcg   1440
gttcggtgga ggaagctagg aagaaggagc catacggatg tggtggtgaa gctgggaaag   1500
ggttccagga tggtggagcg agagcgagtt ggtgatgaag ctagctggcg gcttggcttg   1560
tcaactgcgc ggaggaggcg agcaggcatt gtggagagga tagatagcgg ctcctagacc   1620
agcatgccag tgtgcaagaa aggctgcagg gagagcatgc ggtgcggtaa cattccttga   1680
ggtcggcaac atggtggtgg ttttctgtaa cttggatggt aacttgttta ctttgtctta   1740
atagttatgg gggagttgta ggcttctgtg taaagagata tatctggggc tgtatgtagg   1800
cctttgcggg tgttgtaggt ttttcttttt caggggttatg tcctcttgca tcttgtcaga   1860
agcttttgag ggctgactgc caaggcccag aaagaagaat ggtagatggc aagttgtctt   1920
taaccgctca gaggggaatg aatggtagag ccagcacaac ctcccagttt tgtaagacgt   1980
tgtagtttga acagatgacc taccacaagc ctcactcctg tgtaggggag gtaattgggc   2040
aaagtgcttt tggggggaatg ggggcaaaat atattttgag ttcttttccc cttaggtctg   2100
tctagaatcc taaaggcaga tgactcaagg gaaccagaaa aaaggaaatc cactctcagg   2160
ataagcagag ctcgccaggt ttacagtttg taggaagtag aggatggatg ctagctttca   2220
cactgagtgt ggaggagctg gccatggcgg aattgctggt agtttactct ttcccccctcc   2280 cttaatgaga tttgtaaaat cctaaacact tttacttgaa atatttggga gtggtcttaa   2340
cagggaggag tgggtggggg aaacgttttt tttctaagat tttccacaga tgctatagtt   2400
gtgttgacac actgggttag agaaggcgtg tactgctatg ctgttggcac gacaccttca   2460
gggactggag ctgcctttg tccttggaag agttttccca gttgccgctg aagtcagcac   2520
agtgcggctt tggttcacag tcacctcagg agaacctcag gagcttggct aggccagagg   2580
ttgaagttaa gttttacagc accgtgattt aaaatatttc attaaagggg aggggtaaaa   2640
cttagttggc tgtggccttg tgtttgggtg ggtgggggtg ttaggtaatt gtttagttta   2700
tgatttcaga taatcatacc agagaactta atatttggaa aaacaggaa atctcagctt    2760 tcaagttggc aagtaactcc caatccagtt tttgcttctt ttttcctttt tctttttttg   2820
aggcgggcag ctaaggaagg ttggttcctc tgccggtccc tcgaaagcgt agggcttggg   2880
```

```
ggttggtctg gtccactggg atgatgtgat gctacagtgg ggactcttct gaagctgttg    2940
gatgaatata gattgtagtg tgtggttctc ttttgaaatt ttttcaggt gacttaatgt     3000 atcttaataa ctactatagg aacaaaggaa gtggctttaa tgaccctgaa ggaatttctt    3060
ctggtgatag cttttatatt atcaagtaag agatactatc tcagttttgt ataagcaagt    3120
cttttcccta gtgtaggaga atgattttc cttgtgacta aacaagatgt aaaggtatgc     3180
ttttttcctt cttgtgcatt gtatacttgt gtttatttgt aacttataat ttaagaatta    3240
tgataattca gcctgaatgt cttttagagg gtgggctttt gttgatgagg gaggggaaac    3300
cttttttttt ctgtagacct ttttcagata acaccatctg agtcataacc agcctggcag    3360
tgtgatgacg tagatgcaga gggagcagct ccttggtgaa tgagtgataa gtaaaggcag    3420
aaaaaataat gtcatgtctc catggggaat gagcatgagc cagagattgt tcctactgat    3480
gaaaagctgc atatgcaaaa atttaagcaa atgaaagcaa ccagtataaa gttatggcaa    3540
tacctttaaa agttatggct tatctaccaa gctttatcca caaagtaaa gaattgatga     3600 aaaacagtga agatcaaatg ttcatctcaa aactgctttt acaaaagcag aatagaaatg    3660
aagtgaaaat gctgcattaa gcctggagta aaaagaagct gagcttgttg agatgagtgg    3720
gatcgagcgg ctgcgaggcg gtgcagtgtg ccaatgtttc gtttgcctca gacaggttc     3780 tcttcataag cagaagagtt gcttcattcc atctcggagc aggaaacagc agactgctgt    3840
tgacagataa gtgtaacttg gatctgcagt attgcatgtt agggatagat aagtgccttt    3900
tttctctttt tccaaaaaga cctgtagagc tgttgaatgt ttgcagctgg cccctcttag    3960
gcagttcaga attttgagta gttttcccat ccagcctctt aaaaattcct aagccttgca    4020
ccgatgggct ttcatgatgg gatagctaat aggcttttgc atcgtaaact tcaacacaaa    4080
agcctacatg attaatgcct actttaatta cattgcttac aagattaagg aatctttatc    4140
ttgaagaccc catgaaaggg atcattatgt gctgaaaatt agatgttcat attgctaaaa    4200
tttaaatgtg ctccaatgta cttgtgctta aaatcattaa attatacaaa ttaataaaat    4260
acttcactag agaatgtatg tatttagaag gctgtctcct tatttaaata agtcttgtt     4320 tgttgtctgt agttagtgtg ggcaattttg gggggatgtt cttctctaat cttttcagaa    4380
acttgacttc gaacacttaa gtggaccaga tcaggatttg agccagaaga ccgaaattaa    4440
ctttaaggca ggaaagacaa attttattct ccatgcagtg atgagcattt aataattgca    4500
ggcctggcat agaggccgtc taactaagga ctaagtacct taggcaggtg ggagatgatg    4560
gtcagagtaa aaggtaacta catattttgt ttccagaaag tcagggggtct aatttgacca   4620 tggctaaaca tctagggtaa gacactttc ccccacattt ccaaatatgc atgttgagtt     4680
taaatgctta cgatcatctc atccacttta gccttttgtc acctcacttg agccacgagt    4740
ggggtcaggc atgtgggttt aaagagtttt cctttgcaga gcctcatttc atccttcatg    4800
gagctgctca ggactttgca tataagcgct tgcctctgtc ttctgttctg ctagtgagtg    4860
tgtgatgtga gaccttgcag tgagtttgtt tttcctggaa tgtggaggga ggggggatg    4920 gggcttactt gttctagctt ttttttaca gaccacacag aatgcaggtg tcttgacttc    4980
aggtcatgtc tgttctttgg caagtaatat gtgcagtact gttccaatct gctgctatta    5040
gaatgcattg tgacgcgact ggagtatgat taaagaaagt tgtgtttccc caagtgtttg   5100
gagtagtggt tgttggagga aaagccatga gtaacaggct gagtgttgag gaaatggctc   5160
tctgcagctt taagtaaccc gtgtttgtga ttggagccga gtcccctttgc tgtgctgcct   5220 taggtaaatg ttttttgttca tttctggtga ggggggttgg gagcactgaa gcctttagtc   5280
```

```
tcttccagat tcaacttaaa atctgacaag aaataaatca gacaagcaac attcttgaag    5340
aaattttaac tggcaagtgg aaatgttttg aacagttccg tggtctttag tgcattatct    5400
ttgtgtaggt gttctctctc ccctcccttg gtcttaattc ttacatgcag gaacattgac    5460
aacagcagac atctatctat tcaaggggcc agagaatcca gacccagtaa ggaaaaatag    5520
cccatttact ttaaatcgat aagtgaagca gacatgccat tttcagtgtg gggattggga    5580
agccctagtt ctttcagatg tacttcagac tgtagaagga gcttccagtt gaattgaaat    5640
tcaccagtgg acaaaatgag gacaacaggt gaacgagcct tttcttgttt aagattagct    5700
actggtaatc tagtgttgaa tcctctccag cttcatgctg gagcagctag catgtgatgt    5760
aatgttggcc ttggggtgga ggggtgaggt gggcgctaag cctttttttta agattttttca    5820 ggtacccctc actaaaggca ctgaaggctt aatgtaggac agcggagcct tcctgtgtgg    5880
caagaatcaa gcaagcagta ttgtatcgag accaaagtgg tatcatggtc ggttttgatt    5940
agcagtgggg actaccctac cgtaacacct tgttggaatt gaagcatcca agaaaatac     6000 ttgagaggcc ctgggcttgt tttaacatct ggaaaaaagg ctgttttat agcagcggtt     6060 accagcccaa acctcaagtt gtgcttgcag gggagggaaa aggggggaaag cgggcaacca   6120 gtttccccag ctttcccaga atcctgttac aaggtctccc cacaagtgat ttctctgcca    6180
catcgccacc atgggccttt ggcctaatca cagacccttc accctcacc ttgatgcagc     6240 cagtagctgg atccttgagg tcacgttgca tatcggtttc aaggtaacca tggtgccaag    6300
gtcctgtggg ttgcaccaga aaaggccatc aattttcccc ttgcctgtaa tttaacatta    6360
aaaccatagc taagatgttt tatacatagc acctatgcag agtaaacaaa ccagtatggg    6420
tatagtatgt ttgataccag tgctgggtgg gaatgtagga agtcggatga aaagcaagcc    6480
tttgtaggaa gttgttgggg tgggattgca aaaattctct gctaagactt tttcaggtgg    6540
acataacaga cttggccaag ctagcatctt agtggaagca gattcgtcag tagggttgta    6600 aaggttttc ttttcctgag aaaacaacct tttgttttct caggttttgc ttttttggcct     6660 ttccctagct ttaaaaaaaa aaaagcaaaa gacgctggtg gctggcactc ctggtttcca    6720
ggacggggtt caagtccctg cggtgtcttt gcttgactct tatatcatga ggccattaca    6780
tttttcttgg aggttctaa aggctctggg tatggtagct gatatcactg gaacactccc     6840
cagcctcagt gttgaactct tgataattaa ctgcattgtc tttcaggtta tgcccaattc    6900
gtcttattac ctctgagtcg acacacctcc tactatttat tgaatacttt gattttatga    6960
aataaaaact aaatatctct ca                                             6982

<210> SEQ ID NO 4
<211> LENGTH: 22
<212> TYPE: RNA
<213> ORGANISM: Mus musculus

<400> SEQUENCE: 4
uggagugugu ga caauggugu uu ug                                              22

<210> SEQ ID NO 5
<211> LENGTH: 4178
<212> TYPE: DNA
<213> ORGANISM: Mus musculus

<400> SEQUENCE: 5
ggaaaagcaa aaccccttttg gctttgacag ccaccgccac aagcctttcc gcctccccag        60
```

```
cctgcctagg tgctgggagc tgggagctgg attatggtgg cctgagcagc cgacgcagcc      120
gtaggagccc ggagtccctg tcggtcccca agctgcaaag cccgcctgga agaccccgaa      180
agctacgggc tcggatagcc atgcccgccc ctcccagccc acaaggggcc ccgatccccc      240
cgctggcggc cggcgtccag atgtagctgg gtccctgga tcgccatcgt cgtctcctct      300
cgtgcgctac ggatttctcc tgcccactct ccgccgcctg gaccgggaac tgagcgaggg      360
gcctgcagac tctgcagtcc tgatgccgcc gaggccgctc tcctgagaga agccaccacc      420
acccagactt aggggcaggc aagagggaca gtcaccaacc ggaccacaag gcccgggctc      480
actatggccc cagcgctgca ctggctcctg ctatgggtgg gctcgggaat gctgcctgcc      540
cagggaaccc atctcggcat ccggctgccc cttcgcagcg gcctggcagg gccacccctg      600
ggcctgaggc tgccccggga gaccgacgag gaatcggagg agcctggccg agagaggcagc    660 tttgtggaga tggtggacaa cctgagggga aagtccggcc agggctacta tgtggagatg      720
accgtaggca gccccccaca gacgctcaac atcctggtgg acacgggcag tagtaacttt      780
gcagtggggg ctgccccaca cccttttcctg catcgctact accagaggca gctgtccagc      840
acatatcgag acctccgaaa gggtgtgtat gtgccctaca cccagggcaa gtgggagggg      900
gaactgggca ccgacctggt gagcatccct catggcccca acgtcactgt gcgtgccaac      960
attgctgcca tcactgaatc ggacaagttc ttcatcaatg gttccaactg ggagggcatc    1020
ctagggctgg cctatgctga gattgccagg cccgacgact ctttggagcc cttctttgac    1080
tccctggtga agcagaccca cattcccaac atcttttccc tgcagctctg tggcgctggc    1140
ttccccctca accagaccga ggcactggcc tcggtgggag ggagcatgat cattggtggt    1200
atcgaccact cgctatacac gggcagtctc tggtacacac ccatccggcg ggagtggtat    1260
tatgaagtga tcattgtacg tgtggaaatc aatggtcaag atctcaagat ggactgcaag    1320
gagtacaact acgacaagag cattgtggac agtgggacca ccaaccttcg cttgcccaag    1380
aaagtatttg aagctgccgt caagtccatc aaggcagcct cctcgacgga gaagttcccg    1440
gatggctttt ggctagggga gcagctggtg tgctggcaag caggcacgac cccttggaac    1500
attttcccag tcatttcact ttacctcatg ggtgaagtca ccaatcagtc cttccgcatc    1560
accatccttc ctcagcaata cctacggccg gtggaggacg tggccacgtc ccaagacgac    1620
tgttacaagt tcgctgtctc acagtcatcc acgggcactg ttatgggagc cgtcatcatg    1680
gaaggtttct atgtcgtctt cgatcgagcc cgaaagcgaa ttggctttgc tgtcagcgct    1740
tgccatgtgc acgatgagtt caggacgcg gcagtggaag gtccgtttgt tacggcagac    1800
atggaagact gtggctacaa cattccccag acagatgagt caacacttat gaccatagcc    1860
tatgtcatgg cggccatctg cgccctcttc atgttgccac tctgcctcat ggtatgtcag    1920
tggcgctgcc tgcgttgcct cgccaccag cacgatgact ttgctgatga catctccctg    1980
ctcaagtaag gaggcccgtg ggcagatgat ggagacgccc ctggaccaca tctgggtggt    2040
tccctttggt cacatgagtt ggagctatgg atggtacctg tggccagagc acctcaggac    2100
cctcaccaac ctgccaatgc ttctggcgtg acagaacaga gaaatcaggc aagctggatt    2160
acagggcttg cacctgtagg acacaggaga gggaaggaag cagcgttctg gtggcaggaa    2220
tatccttaga caccacaaac ttgagttgga aattttgctg cttgaagctt cagccctgac    2280
cctctgccca gcatccttta gagtctccaa cctaaagtat tctttatgtc cttccagaag    2340
tactggcgtc atactcaggc tacccggcat gtgtccctgt ggtaccctgg cagagaaagg    2400
gccaatctca ttccctgctg gccaaagtca gcagaagaaa gtgaagtttg ccagttgctt    2460
```

```
tagtgatagg gactgcagac tcaagcctac actggtacaa agactgcgtc ttgagataaa    2520
caagaaccta tgcgatgcga atgtttatac tcctgggggc agtcaagatg aggagacagg    2580
ataggataga gacaggaagg agatggtagc aaaactggga aaggcagaac tctgatcact    2640
ttctagttcc aagtttagac tcatctccaa gacagaagcc catctggact aagaggtatc    2700
attccccaat gtgcctgtgg ttgtagtctg aactgaaatg aaatggggga aaaagggctt    2760
attagccaaa gagctctttt taacactctt agaggaacag tgctcatgag aaaagtccca    2820
ctggacagat gaattcctat cttgttaatt ctgtctctct ctgcttcttc aacatgctaa    2880
gtggcaccaa aatgacccaa ccccaaggtc ttaggtgccc tatgggacaa cagttagaat    2940
attgtagggc tagggatggt cttcccagca taggttcact ccaaccaagg tgctaaaagg    3000
aacagacagg agagtcctcc tctctgatcc acaaaggcag agccctcaag attcatccag    3060
cagggttagg gctgatgcat ttgcctctgc ctggattttg ttttattttt ctttctttt     3120 gcccagtggt acaaaacgat aagctcttta tggaatactg agtgggttca ttcctctctt    3180
gccctctcca atggcccctc tatttatctg gctaaggaaa caccacgcat tggctagtat    3240
taaacagcaa ctgtaagata gagggctttc tgttctatgt cattgccttc agtatcaagg    3300
ctgcctggag aaaggatggc agcctcaggg cttccttact ttcttctcct ttcctgacag    3360
agcagccttt ctgtcctgct ctctgctgcc cctcccaata taatccatgg gtacccaggc    3420
tggttcttgg gctaggttgt gggggccaca ctcacctctt ccctgccagt ctaacacga    3480 cagacatgaa gccagtgtta gtgggaagag ctgggttttc ccaggatgac cactgcatcc    3540
tctcctggta cgctctacac tgctttcagg ctggggacct gccaagtgtg ggacagttga    3600
tgaggaagag acattagcag ggcctctgga gttgctggcc cagccagctg cccacaagcc    3660
ataaaccaat aaaataagaa tcctgcgtca cagtttccag ctgggtcctc ttccttgccc    3720
tcgcactggt gctgctctgg ctgagtagga atacacccac agactgccag gaagatggag    3780
actgtccgct tccggctcag aactacagtg taattaagct tccaggatca ctaccatgaa    3840
aacgccgcat tctgctttat catttctacc catgttggga aaaactggct ttttccccat    3900
ttctttacag ggcaaaaaaa aaaaaaaaaa aagggagaga gagagagaac tcaacctagt    3960
tgttatttac cctagtaact ggtgttctat tttttttaa aggggaaaa tttgcattta      4020 tttttctttt gatggttaac tcctttgtat cataaaatta tgaactctga tatgtaaaac    4080
agaaaaaaat cttgacaaca gcttctcgct tgtaaaaata tgtattatac agctctattt    4140
tcaaagtctc ctgaaaaatg actgacctat ctccactg                             4178

<210> SEQ ID NO 6
<211> LENGTH: 8229
<212> TYPE: DNA
<213> ORGANISM: Mus musculus

<400> SEQUENCE: 6
gcggcaggat acgcgcttgg gcgtcgggac gcggctgcgc tcagctctct cctctcggaa      60
gctgcagcca tgatggaagt ttgagagttg agccgctgtg aggccaggcc cggcgcaggc     120
gagggagatg agagacggcg gcggccacgg cccagagccc ctctcagcgc ctgtgagcag     180 ccgcggggggc agcgcccctcg gggagccggc cgggcggcgg cggcggcagc ggcggcgggc    240
ctcgcctcct cgtcgtctgt tctaaccggg cagcttctga gcagcttcgg agagagacgg     300
tggaagaagc cgtgggctcg agcgggagcc ggcgcaggct cggcggctgc acctcccgct    360
```

| | |
|---|---|
| cctggagcgg gggggagaag cggcggcggc ggccgcggct ccggggaggg ggtcggagtc | 420 |
| gcctgtcacc attgccaggg ctgggaacgc cggagagttg ctctctcccc ttctcctgcc | 480 |
| tccaacacgg cggcggcggc ggcggcacgt ccagggaccc gggccggtgt taagcctccc | 540 |
| gtccgccgcc gccgcacccc ccctggcccg ggctccggag gccgcggag gaggcagccg | 600 |
| ctgcgaggat tatccgtctt ctccccattc cgctgcctcg gctgccaggc ctctggctgc | 660 |
| tgaggagaag caggcccagt ctctgcaacc atccagcagc cgccgcagca gccattaccc | 720 |
| ggctgcggtc cagggccaag cggcagcaga gcgaggggca tcagcgaccg ccaagtccag | 780 |
| agccatttcc atcctgcaga agaagcctcg ccaccagcag cttctgccat ctctctcctc | 840 |
| cttttcttc agccacaggc tcccagacat gacagccatc atcaaagaga tcgttagcag | 900 |
| aaacaaaagg agatatcaag aggatggatt cgacttagac ttgacctata tttatccaaa | 960 |
| tattattgct atgggatttc ctgcagaaag acttgaaggt gtatacagga acaatattga | 1020 |
| tgatgtagta aggttttttgg attcaaagca taaaaaccat tacaagatat acaatctatg | 1080 |
| tgctgagaga cattatgaca ccgccaaatt taactgcaga gttgcacagt atccttttga | 1140 |
| agaccataac ccaccacagc tagaacttat caaaccctcc tgtgaagatc ttgaccaatg | 1200 |
| gctaagtgaa gatgacaatc atgttgcagc aattcactgt aaagctggaa agggacggac | 1260 |
| tggtgtaatg atttgtgcat atttattgca tcggggcaaa ttttttaaagg cacaagaggc | 1320 |
| cctagatttt tatggggaag taaggaccag agacaaaaag ggagtcacaa ttcccagtca | 1380 |
| gaggcgctat gtatattatt atagctacct gctaaaaaat cacctggatt acagacccgt | 1440 |
| ggcactgctg tttcacaaga tgatgtttga aactattcca atgttcagtg cggaacttg | 1500 |
| caatcctcag tttgtggtct gccagctaaa ggtgaagata tattcctcca attcaggacc | 1560 |
| cacgcggcgg gaggacaagt tcatgtactt tgagttccct cagccattgc ctgtgtgtgg | 1620 |
| tgatatcaaa gtagagttct tccacaaaca gaacaagatg ctcaaaaagg acaaaatgtt | 1680 |
| tcacttttgg gtaaatacgt tcttcatacc aggaccagag gaaacctcag aaaaagtgga | 1740 |
| aaatggaagt ctttgtgatc aggaaatcga tagcatttgc agtatagagc gtgcagataa | 1800 |
| tgacaaggag tatcttgtac tcaccctaac aaaaaacgat cttgacaaag caaacaaaga | 1860 |
| caaggccaac cgatacttct ctccaaattt taaggtgaaa ctatacttta caaaaacagt | 1920 |
| agaggagcca tcaaatccag aggctagcag ttcaacttct gtgactccag atgttagtga | 1980 |
| caatgaacct gatcattata gatattctga caccactgac tctgatccag agaatgaacc | 2040 |
| ttttgatgaa gatcagcatt cacaaattac aaaagtctga ttttttttttt cttatcaaga | 2100 |
| gggataaaat accatgaaaa aaaaaaaact tgaataaact gaaatggacc tttttttttt | 2160 |
| tttttttttt ttaaatggca ataggacatt gtgtcagatt gcagttatag gaacaattct | 2220 |
| cttctcctga ccaatcttgt tttaccctat acatccacag ggttttgaca cttgttgtcc | 2280 |
| agttaaaaaa aggttgtgta gctgtgtcat gtatatacct ttttgtgtca aaaggacatt | 2340 |
| taaaattcaa ttaggataaa taaaagatgg cactttccca ttttattcca gttttataaa | 2400 |
| aagtggagac aggctgatgt gtatacgcag gagttttttcc tttattttct gtcaccagct | 2460 |
| gaagtggctg aagagctctg attcccgggt tcacgtccta cccctttgca cttgtggcaa | 2520 |
| cagataagtt tgcagttggc taaggaagtt tctgcagggt tttgttagat tctaatgcat | 2580 |
| gcacttgggt tgggaatgga gggaatgctc agaaaggaat gttctacct gggctctgga | 2640 |
| ccatacacca tctccagctc cttagatgca ccttttcttta gcatgctcca cttactaatc | 2700 |
| tggacatccg agagattggc tgctgtcctg ctgtttgttt gtgcatttta aagagcatat | 2760 |

```
tggtgctaga caaggcagct agagtgagta tatttgtagt ggggtacagg aatgaaccat    2820
ctacagcatc ttaagaatcc acaaaggaag ggatataaaa aaagtggtca tagatagata    2880
aaagacacag cagcaatgac ttaaccatac aaatgtggag gctttcaaca aaggatgggc    2940
tggaaacaga aaatttgaca atgatttatt cagtatgctt tctcagttgt aatgactgct    3000
ccatctccta tgtaatcaag gccagtgcta agagtcagat gctattagtc cctacatcag    3060
tcaacacctt acctttattt ttattaattt tcaatcatat acctactgtg gatgcttcat    3120
gtgctggctg ccagtttgtt tttctcctta aatattttat aattcttcac aggaaatttc    3180
aacttgagat tcaacagtaa gcaggttttg tttttttttt ttcctagaga ttgatgatgc    3240
gcgtcctcag tccagtggct gtcagacgtt cagccccttt gaccttacac attctattac    3300
aatgagtttt gcagttttgc acattttttt taaatgtcat taactgttag ggaattttac    3360
ttgaatactg aatacatata atgtgtatat taaaaaagtc attgtttgtg ttaaaaaaga    3420
aattagagtt gcagtaaatt tacagcactg cacgaataat aaggcattga agtttttcag    3480
tagaaattgt cctacagatg ctttatcgac ttgctattgg aagaatagat cttcttaaat    3540
gtgcagtgtt gagtcacttc gttatagtgg tagagttggg attagggctt caattttact    3600
tcttaaatat cattctatgt ttgatatgcc cagactgcat acaatttaaa gcaagagtac    3660
aactactatc gtaatggtaa tgtgaagatg ctattacaaa ggatctcctc ccaaccccctc   3720 gggaatttgg tgtctttcaa attatatctt gaccttgaca tttgaatatc cagccattat    3780
tagatttctt aatggtgtga agtcccattt tcaataactt attggtgctg aaattgttca    3840
ctagctgtgg tctgacctag ttaatttaca agtacagatt gcataggacc cactagagaa    3900
gcatttatag tttgatggta agtagattag gcagaacgcc atctaaaata ttcttagaaa    3960
ataatgttga tgtattttcc atacctcatc agtttcactc aaccaataaa gttttttaaaa   4020 ttgtaacaaa gctcttagga tttacacatt tatatttaaa cattgataca tgaatattga    4080
ctgactgttg ataaagtcag agacaacttt tcctgagatc tcaccatgga aatctgtaca    4140
cccccttgtc tttcctaaaa gctgaaagtg gctgactaaa atgcaaagca gctgttgatg    4200
ttttgaagat agtgataaac actgttcttt gttagttttg ggcacagcat gctaaactat    4260
aacttgtatt gttccaatat gtaacacaga gggccaggtc atgaataatg acattacaat    4320
gggctgttgc actgttaata ttttttccttt ggaatgtgaa ggtctgaatg agggttttga    4380
ttttgaatgt ttcagtgttt ttgagaagcc ttgcttacat tttatggtgt agtcattgga    4440
aatgaaaaaa tggcattata tatatattat atatatataa atatatatat tatacatact    4500
ctccttactt tatttcagtt accatcccca tagaatttga caagaattgc tatgactgaa    4560 agggtttttga gtcctaattc aaactttctt tatgacagta ttcacgatta gcctgaagtg    4620
cattctgtag gtgatctctc ccgtgtttct ggaatgcttt cttagactct tggatgtgca    4680
gcagcttatg tgtctgaaat gacttgaagg catcaccttt aagaaggctt acagttgggc    4740
cccgtacatc ccaagtcctc tgtaattcct cttggacatt tttgccataa ttgtaaaagg    4800
gtagttgaat taaatagcgt caccattctt tgctgtggca caggttataa acttaagtgg    4860
agtttaccgg cagcatcaaa tgtttcagct ttaaaaataa aagtaggtta caagttacat    4920
gtttagtttt agaaaatttg tgcaatatgt tcataacgat ggctgtggtt gccacaaagt    4980
gcctcgttta cctttaaata ctgttaatgt gtcgtgcatg cagacggaag gggtggatct    5040
gtgcactaaa cggggggctt ttactctagt attcggcaga gttgccttct acctgccagc    5100
```

```
tcaaaagttc gatctgtttt catatagaat atatatacta aaaccatcca gtctgtaaaa    5160
cagccttacc ccgattcagc ctcttcagat actcttgtgc tgtgcagcag tggctctgtg    5220
tgtaaatgct atgcactgag gatacacaaa tatgacgtgt acaggataat gcctcatacc    5280
aatcagatgt ccatttgtta ctgtgtttgt taacaaccct ttatctctta gtgttataaa    5340
ctccacttaa aactgattaa agtctcattc ttgtcattgt gtgggtgttt tattaaatga    5400
gagtatttat aattcaaatt gcttaaatcc attaaaatgt tcagtaatgg gcagccacat    5460
atgattacaa agttcctgtg cattttctta ttttccccc tccttgctat ccttccaagc     5520
aaagcatctt tctgtcatct tggtagacac ataccatgtct actcatggtt aagaagagca   5580
ctttaagcct tagtcatcac ttaataagtt attccaggca cagtaaaaag ttcaaggttc    5640
ttggaaaacg gtgcttattt ctcttcttat aagccagatg tctgaagata gccctaaccc    5700
caagaacggg cttgatgtct caggtctgtt ctgtggcttt ctgtttttt  taacactgca    5760 gttggccatc agcacatggg aggtttcatc gggacttgtc cagagtagta ggctcaaata    5820
tactatctcc tttctaatat tcttaaaggc taaggagtcc tttcaatata acagtaagat    5880
aacttgtgat gttttagaag taagcagacc attaatgtca atgtggagtc ttaatgttac    5940
atgaagttga tagtttctct gtgacccatt taaaaataca aaccgagtag catgcaatta    6000
tgtaaagaaa tatgaagatt atatgtagtc acacattttc tttagaattc ttagtttggt    6060
gaaaacttga atataaaggt attttgattt atatgacatt ttgatgatat ttgaaaaaaa    6120
ggaatttcct gacattttgc ttttagatca tgtcccccat tgtgctgtaa tttaagccaa    6180
cttggttcag tgaatgccat caccatttcc attgagaatt taaaactcac cagtgtttaa    6240
catgcaggct tctgagggct cccggagaat cagaccttaa gcccagttga tttacttcta    6300
acgtgaaact tcgagttcct gtatactttg ctagataatt tgtggtacat ctaaagctta    6360
gtcttaagtg gcttgtgtgt ggatttttatt caacattctt gttgctaggg tagagagaaa   6420
tgttgctgag tagaaacaag agtacccagt tcaatgtggt acagagagca gtccctaaaa    6480
tctgtacaca gtgtaatgga ccactttagg agtcaagagg ctgattttc  ctatgaaatt    6540 acattgcaac aggaagcctt ctagtatagt tccttttact gttagaatat gttttatgc     6600 atacgctata gctgctttcc catcttccaa caacaggtat caggatgtaa gcaagcttta    6660
aacagtgtga agatggcagg atagtgtcat cggtaacagt cctctgactc taaatgtagt    6720
tgctctgtaa cactttgtga atataacatc acaattctca tgtccttggg ggggggggggc   6780 atacccagta ttagtatgtt ttagtgacta agcaatcatt tttctgttta ctcatgtaca    6840
ttttctcttt aaaactaaaa cctgtactgt gtatgtctcc aaagccttt  agcttagttt    6900 ttaggaaatg aacactgaat ggatcacttt ttagtgtagc aggtatggga tatgtgcatt    6960
atagagagac cttgtcagct ctctgggcct atttgaatgt ttattgttgg tgtgaggatg    7020
gtaggggaat cagtaaatac aagttacgtt ggtttagcag agcaagctca gtgtgggtat    7080
ttctctttga agcgtggtgc gtgacgcact gtgagtagag aatttggtca ccctttgagt    7140
cctcttgcat tttgcaaact tgctcagcaa atgcgtacct accttgcccc ctaggtaaaa    7200
gcaggaacta ctactgattt atctgtcact cagctgtctt tatatgtgtg cttctgtgac    7260
ttgtatcaca caagaatctt aaagatttca caaattgtta cctttagct  ctgaatgttg    7320 agtattctgg tgggctaaca acaagacaaa ctccttgacag tcatttgaga attttcatga   7380
aacatttagc tgaaaacatt ttataattta tgaaaaaaat gtgttacctt aaactttac     7440 atatgtggga gacattaact gccatatttg agcatactga atttaaaatt taaaataaag    7500
```

```
ctgcatattt ttaaatgaaa tgtttaacaa ggattcatat tttttgtttt ttaagattaa      7560
aaataattta tgtcttctca tgtggaacct catctgtcac aatggttaga ttatacagaa      7620
tggagcaagg cttgtagtgg tttagcttac agtaaaattc ttaatgttta gatgtgttta      7680
cttactggct gttatgtata cttttgagat tttccacctg ttctgtgtag ttttctaaat      7740
gatactccta cttaaaaaca gcatttagt atctattttc tgtctccatt aaatggtcct       7800
cattttctat tgagtttgga agtgtgcaca ttgtgtgtgt gtgtgtgtgt gtgtgtgtgc      7860
acacgtgtgc gcgcccgtgc gtgtgtctat ttgtggagtt tgtatgggag aattagtttt      7920
gaaagtgcta gaatagagat gaaatttggt tcaagtaaaa ttttcccact gggattttac      7980
agtttattgt aataaaatgt taattttgga tgaccttgaa tattaatgaa tttgttagcc      8040
tcttgatgtg tgcattaatg agatatatca aagttgtata ttaaaccaaa gttggagttg      8100
tggaagtgtt tttatgaagt tccgtttggc taccaatgga cataagacta gaaataccrt      8160
cctgtggaga atattttcc tttaaacaat taaaaggtt cattatttt gaaaaaaaaa         8220 aaaaaaaaa                                                              8229
```

<210> SEQ ID NO 7
<211> LENGTH: 13
<212> TYPE: DNA
<213> ORGANISM: Artificial
<220> FEATURE:
<223> OTHER INFORMATION: Synthetic

<400> SEQUENCE: 7
ctaggtcatg cgt                                                         13

<210> SEQ ID NO 8
<211> LENGTH: 15
<212> TYPE: DNA
<213> ORGANISM: Artificial
<220> FEATURE:
<223> OTHER INFORMATION: Synthetic

<400> SEQUENCE: 8
cgcattggta ttcgc                                                       15

<210> SEQ ID NO 9
<211> LENGTH: 13
<212> TYPE: DNA
<213> ORGANISM: Artificial
<220> FEATURE:
<223> OTHER INFORMATION: Synthetic

<400> SEQUENCE: 9
gtaggtcatg cgt                                                         13

<210> SEQ ID NO 10
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1), (11)..(11), (13)..(13)
<223> OTHER INFORMATION: LNA
<220> FEATURE:
<221> NAME/KEY: misc_feature
<222> LOCATION: (2)..(2), (12)..(12)
<223> OTHER INFORMATION: 5-methylcytosine LNA

```
<400> SEQUENCE: 10
gcattggtat tca                                                             13

<210> SEQ ID NO 11
<211> LENGTH: 13
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3), (12)..(13)
<223> OTHER INFORMATION: 2'-O-Me RNA

<400> SEQUENCE: 11
ugaauaccaa ugc                                                             13

<210> SEQ ID NO 12
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 12
ctaggtcatg cgtugaauac caaugc                                               26

<210> SEQ ID NO 13
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA

<400> SEQUENCE: 13
ctaggtcatg cgt                                                             13

<210> SEQ ID NO 14
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
```

```
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 14
ctaggtcatg cgtugaauac caaugc                                            26

<210> SEQ ID NO 15
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (15)..(15), (25)..(26)
<223> OTHER INFORMATION: LNA
<220> FEATURE:
<221> NAME/KEY: misc_feature
<222> LOCATION: (14)..(14), (24)..(24)
<223> OTHER INFORMATION: 5-methylcytosine LNA
<220> FEATURE:
<221> NAME/KEY: misc_feature
<222> LOCATION: (3)..(13)
<223> OTHER INFORMATION: RNA
<220> FEATURE:
<221> NAME/KEY: misc_feature
<222> LOCATION: (1)..(2)
<223> OTHER INFORMATION: 2'-O-Me RNA

<400> SEQUENCE: 15
ugaauaccaa ugcctaggtc atgcgt                                            26

<210> SEQ ID NO 16
<211> LENGTH: 26
<212> TYPE: DNA
<213> ORGANISM: Artificial
<220> FEATURE:
<223> OTHER INFORMATION: DNA/RNA molecule
<220> FEATURE:
<223> OTHER INFORMATION: Synthetic
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (25)..(26)
<223> OTHER INFORMATION: 2'-O-Me RNA

<400> SEQUENCE: 16
ctaggtcatg cgttgaatac caatgc                                            26

<210> SEQ ID NO 17
```

```
<211> LENGTH: 26
<212> TYPE: DNA
<213> ORGANISM: Artificial
<220> FEATURE:
<223> OTHER INFORMATION: DNA/RNA molecule
<220> FEATURE:
<223> OTHER INFORMATION: Synthetic
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (14)..(26)
<223> OTHER INFORMATION: 2'-O-Me RNA

<400> SEQUENCE: 17
ctaggtcatg cgtugaauac caaugc                                              26

<210> SEQ ID NO 18
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 18
ctaggtcatg cgtugaauac caaugc                                              26

<210> SEQ ID NO 19
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 19
ctaggtcatg cgtugaauac caaugc                                              26

<210> SEQ ID NO 20
<211> LENGTH: 26
```

```
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (25)..(26)
<223> OTHER INFORMATION: 2'-O-Me RNA

<400> SEQUENCE: 20
cuaggucaug cguugaauac caaugc                                          26

<210> SEQ ID NO 21
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 21
ctaggtcatg cgtugaauac caaugc                                          26

<210> SEQ ID NO 22
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 22
```
ctaggtcatg cgtugaauac caaugc                                              26

<210> SEQ ID NO 23
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 23
ctaggtcatg cgtugaauac caaugc                                              26

<210> SEQ ID NO 24
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 24
ctaggtcatg cgtugaauac caaugc                                              26

<210> SEQ ID NO 25
<211> LENGTH: 24
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (12)..(22)
<223> OTHER INFORMATION: RNA
<220> FEATURE:
<221> NAME/KEY: misc_feature
<222> LOCATION: (23)..(24)
<223> OTHER INFORMATION: 2'-O-Me RNA

<400> SEQUENCE: 25
ctaggtcatg cugaauacca augc                                                24

<210> SEQ ID NO 26
<211> LENGTH: 22

-continued

```
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (10)..(20)
<223> OTHER INFORMATION: RNA
<220> FEATURE:
<221> NAME/KEY: misc_feature
<222> LOCATION: (21)..(22)
<223> OTHER INFORMATION: 2'-O-Me RNA

<400> SEQUENCE: 26
ctaggtcatu gaauaccaau gc                                          22

<210> SEQ ID NO 27
<211> LENGTH: 20
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (8)..(18)
<223> OTHER INFORMATION: RNA
<220> FEATURE:
<221> NAME/KEY: misc_feature
<222> LOCATION: (19)..(20)
<223> OTHER INFORMATION: 2'-O-Me RNA

<400> SEQUENCE: 27
ctaggtcuga auaccaaugc                                             20

<210> SEQ ID NO 28
<211> LENGTH: 18
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (6)..(16)
<223> OTHER INFORMATION: RNA
<220> FEATURE:
<221> NAME/KEY: misc_feature
<222> LOCATION: (17)..(18)
<223> OTHER INFORMATION: 2'-O-Me RNA

<400> SEQUENCE: 28
ctaggugaau accaaugc                                               18

<210> SEQ ID NO 29
<211> LENGTH: 15
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (3)..(13)
<223> OTHER INFORMATION: RNA
<220> FEATURE:
<221> NAME/KEY: misc_feature
<222> LOCATION: (14)..(15)
```

```
<223> OTHER INFORMATION: 2'-O-Me RNA

<400> SEQUENCE: 29
ctugaauacc aaugc                                                      15

<210> SEQ ID NO 30
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 30
ctaggtcatg cgtugaauac caaugc                                          26

<210> SEQ ID NO 31
<211> LENGTH: 24
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (2)..(2), (10)..(11)
<223> OTHER INFORMATION: LNA
<220> FEATURE:
<221> NAME/KEY: misc_feature
<222> LOCATION: (1)..(1), (9)..(9)
<223> OTHER INFORMATION: 5-methylcytosine LNA
<220> FEATURE:
<221> NAME/KEY: misc_feature
<222> LOCATION: (12)..(22)
<223> OTHER INFORMATION: RNA
<220> FEATURE:
<221> NAME/KEY: misc_feature
<222> LOCATION: (23)..(24)
<223> OTHER INFORMATION: 2'-O-Me RNA

<400> SEQUENCE: 31
ctaggtcacg tugaauacca augc                                            24

<210> SEQ ID NO 32
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2), (11)..(12)
<223> OTHER INFORMATION: LNA
<220> FEATURE:
<221> NAME/KEY: misc_feature
```

```
<222> LOCATION: (1)..(1), (13)..(13)
<223> OTHER INFORMATION: 5-methylcytosine LNA

<400> SEQUENCE: 32
cagtcatgac ttc                                                         13

<210> SEQ ID NO 33
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 33
ctaggtcatg cgtgaaguca ugacug                                           26

<210> SEQ ID NO 34
<211> LENGTH: 22
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (10)..(20)
<223> OTHER INFORMATION: RNA
<220> FEATURE:
<221> NAME/KEY: misc_feature
<222> LOCATION: (21)..(22)
<223> OTHER INFORMATION: 2'-O-Me RNA

<400> SEQUENCE: 34
ctaggtcgtg aagucaugac ug                                               22

<210> SEQ ID NO 35
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(3), (14)..(15)
<223> OTHER INFORMATION: LNA
<220> FEATURE:
<221> NAME/KEY: misc_feature
<222> LOCATION: (1)..(1), (16)..(16)
<223> OTHER INFORMATION: 5-methylcytosine LNA

<400> SEQUENCE: 35
ctagttcact gaatgc                                                      16

<210> SEQ ID NO 36
<211> LENGTH: 29
<212> TYPE: DNA
<213> ORGANISM: Artificial
<220> FEATURE:
<223> OTHER INFORMATION: Synthetic
<220> FEATURE:
```

```
<223> OTHER INFORMATION: DNA/RNA molecule
<220> FEATURE:
<221> NAME/KEY: misc_feature
<222> LOCATION: (14)..(27)
<223> OTHER INFORMATION: RNA
<220> FEATURE:
<221> NAME/KEY: misc_feature
<222> LOCATION: (28)..(29)
<223> OTHER INFORMATION: 2'-O-Me RNA

<400> SEQUENCE: 36
ctaggtcatg cgtgcauuca gugaacuag                                29

<210> SEQ ID NO 37
<211> LENGTH: 25
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (10)..(23)
<223> OTHER INFORMATION: RNA
<220> FEATURE:
<221> NAME/KEY: misc_feature
<222> LOCATION: (24)..(25)
<223> OTHER INFORMATION: 2'-O-Me RNA

<400> SEQUENCE: 37
ctaggtcgtg cauucaguga acuag                                    25

<210> SEQ ID NO 38
<211> LENGTH: 21
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (6)..(19)
<223> OTHER INFORMATION: RNA
<220> FEATURE:
<221> NAME/KEY: misc_feature
<222> LOCATION: (20)..(21)
<223> OTHER INFORMATION: 2'-O-Me RNA

<400> SEQUENCE: 38
ctcgtgcauu cagugaacua g                                        21

<210> SEQ ID NO 39
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(3), (6)..(7)
<223> OTHER INFORMATION: LNA
<220> FEATURE:
<221> NAME/KEY: misc_feature
<222> LOCATION: (1)..(1), (10)..(10),(12)..(12), (14)..(15)
<223> OTHER INFORMATION: 5-methylcytosine LNA

<400> SEQUENCE: 39
ccattgtcac actcc                                               15
```

<210> SEQ ID NO 40
<211> LENGTH: 30
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (6)..(7), (10)..(10), (12)..(12), (14)..(14)
<223> OTHER INFORMATION: LNA
<220> FEATURE:
<221> NAME/KEY: misc_feature
<222> LOCATION: (1)..(1), (3)..(3), (15)..(15)
<223> OTHER INFORMATION: 5-methylcytosine LNA
<220> FEATURE:
<221> NAME/KEY: misc_feature
<222> LOCATION: (16)..(28)
<223> OTHER INFORMATION: RNA
<220> FEATURE:
<221> NAME/KEY: misc_feature
<222> LOCATION: (29)..(30)
<223> OTHER INFORMATION: 2'-O-Me RNA

<400> SEQUENCE: 40
cgcattggta ttcgcggagu gugacaaugg                                30

<210> SEQ ID NO 41
<211> LENGTH: 15
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3), (13)..(15)
<223> OTHER INFORMATION: 2'-O-Me RNA

<400> SEQUENCE: 41
ggagugugac aaugg                                                15

<210> SEQ ID NO 42
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (6)..(7), (10)..(10), (12)..(12), (14)..(14)
<223> OTHER INFORMATION: LNA
<220> FEATURE:
<221> NAME/KEY: misc_feature
<222> LOCATION: (1)..(1), (3)..(3), (15)..(15)
<223> OTHER INFORMATION: 5-methylcytosine LNA

<400> SEQUENCE: 42
cgcattggta ttcgc                                                15

<210> SEQ ID NO 43
<211> LENGTH: 30
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (3)..(3), (6)..(7)
<223> OTHER INFORMATION: LNA
<220> FEATURE:

```
<221> NAME/KEY: misc_feature
<222> LOCATION: (1)..(1), (10)..(10), (12)..(12), (14)..(15)
<223> OTHER INFORMATION: 5-methylcytosine LNA
<220> FEATURE:
<221> NAME/KEY: misc_feature
<222> LOCATION: (16)..(28)
<223> OTHER INFORMATION: RNA
<220> FEATURE:
<221> NAME/KEY: misc_feature
<222> LOCATION: (29)..(30)
<223> OTHER INFORMATION: 2'-O-Me RNA

<400> SEQUENCE: 43
ccattgtcac actccgcgaa uaccaaugcg                                    30

<210> SEQ ID NO 44
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (11)..(13)
<223> OTHER INFORMATION: LNA

<400> SEQUENCE: 44
gtattgctga gga                                                      13

<210> SEQ ID NO 45
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2), (12)..(13)
<223> OTHER INFORMATION: LNA
<220> FEATURE:
<221> NAME/KEY: misc_feature
<222> LOCATION: (11)..(11)
<223> OTHER INFORMATION: 5-methylcytosine LNA
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 45
gtaggtcatg cgtuccucag caauac                                        26

<210> SEQ ID NO 46
<211> LENGTH: 13
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3), (12)..(13)
<223> OTHER INFORMATION: 2'-O-Me RNA

<400> SEQUENCE: 46
uccucagcaa uac                                                      13
```

```
<210> SEQ ID NO 47
<211> LENGTH: 13
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (2)..(3), (12)..(13)
<223> OTHER INFORMATION: 2'-O-Me RNA
<220> FEATURE:
<221> NAME/KEY: misc_feature
<222> LOCATION: (1)..(1)
<223> OTHER INFORMATION: Tocopherol-conjugated 2'-O-Me RNA

<400> SEQUENCE: 47
uccucagcaa uac                                                        13

<210> SEQ ID NO 48
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (15)..(16)
<223> OTHER INFORMATION: LNA
<220> FEATURE:
<221> NAME/KEY: misc_feature
<222> LOCATION: (3)..(3), (14)..(14)
<223> OTHER INFORMATION: 5-methylcytosine LNA

<400> SEQUENCE: 48
atcatggctg cagctt                                                     16

<210> SEQ ID NO 49
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA

<400> SEQUENCE: 49
ctaggtcatg cgt                                                        13

<210> SEQ ID NO 50
<211> LENGTH: 29
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2), (15)..(16)
<223> OTHER INFORMATION: LNA
<220> FEATURE:
<221> NAME/KEY: misc_feature
<222> LOCATION: (3)..(3), (14)..(14)
<223> OTHER INFORMATION: 5-methylcytosine LNA
<220> FEATURE:
<221> NAME/KEY: misc_feature
<222> LOCATION: (17)..(27)
```

```
<223> OTHER INFORMATION: RNA
<220> FEATURE:
<221> NAME/KEY: misc_feature
<222> LOCATION: (28)..(29)
<223> OTHER INFORMATION: 2'-O-Me RNA

<400> SEQUENCE: 50
atcatggctg cagcttacgc augaccuag                                29

<210> SEQ ID NO 51
<211> LENGTH: 29
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (2)..(2), (12)..(13)
<223> OTHER INFORMATION: LNA
<220> FEATURE:
<221> NAME/KEY: misc_feature
<222> LOCATION: (1)..(1), (11)..(11)
<223> OTHER INFORMATION: 5-methylcytosine LNA
<220> FEATURE:
<221> NAME/KEY: misc_feature
<222> LOCATION: (14)..(27)
<223> OTHER INFORMATION: RNA
<220> FEATURE:
<221> NAME/KEY: misc_feature
<222> LOCATION: (28)..(29)
<223> OTHER INFORMATION: 2'-O-Me RNA

<400> SEQUENCE: 51
ctaggtcatg cgtaagcugc agccaugau                                29

<210> SEQ ID NO 52
<211> LENGTH: 14121
<212> TYPE: DNA
<213> ORGANISM: Homo sapiens

<400> SEQUENCE: 52
attcccaccg ggacctgcgg ggctgagtgc ccttctcggt tgctgccgct gaggagcccg      60
cccagccagc cagggccgcg aggccgaggc caggccgcag cccaggagcc gccccaccgc     120
agctggcgat ggacccgccg aggcccgcgc tgctggcgct gctggcgctg cctgcgctgc     180
tgctgctgct gctggcgggc gccagggccg aagaggaaat gctggaaaat gtcagcctgg     240
tctgtccaaa agatgcgacc cgattcaagc acctccggaa gtacacatac aactatgagg     300
ctgagagttc cagtggagtc cctgggactg ctgattcaag aagtgccacc aggatcaact     360
gcaaggttga gctggaggtt ccccagctct gcagcttcat cctgaagacc agccagtgca     420
ccctgaaaga ggtgtatggc ttcaaccctg agggcaaagc cttgctgaag aaaaccaaga     480
actctgagga gtttgctgca gccatgtcca ggtatgagct caagctggcc attccagaag     540
ggaagcaggt tttcctttac ccggagaaag atgaacctac ttacatcctg aacatcaaga     600
ggggcatcat ttctgccctc ctggttcccc agagacaga agaagccaag caagtgttgt     660
ttctggatac cgtgtatgga aactgctcca ctcactttac cgtcaagacg aggaagggca     720
atgtggcaac agaaatatcc actgaaagag acctggggca gtgtgatcgc ttcaagccca     780
tccgcacagg catcagccca cttgctctca tcaaaggcat gacccgcccc ttgtcaactc     840
tgatcagcag cagccagtcc tgtcagtaca cactggacgc taagaggaag catgtggcag     900
aagccatctg caaggagcaa caccttcttcc tgcctttctc ctacaagaat aagtatggga     960
```

```
tggtagcaca agtgacacag actttgaaac ttgaagacac accaaagatc aacagccgct    1020
tctttggtga aggtactaag aagatgggcc tcgcatttga gagcaccaaa tccacatcac    1080
ctccaaagca ggccgaagct gttttgaaga ctctccagga actgaaaaaa ctaaccatct    1140
ctgagcaaaa tatccagaga gctaatctct tcaataagct ggttactgag ctgagaggcc    1200
tcagtgatga agcagtcaca tctctcttgc cacagctgat tgaggtgtcc agccccatca    1260
ctttacaagc cttggttcag tgtggacagc ctcagtgctc cactcacatc ctccagtggc    1320
tgaaacgtgt gcatgccaac ccccttctga tagatgtggt cacctacctg gtggccctga    1380
tccccgagcc ctcagcacag cagctgcgag agatcttcaa catggcgagg gatcagcgca    1440
gccgagccac cttgtatgcg ctgagccacg cggtcaacaa ctatcataag acaaacccta    1500
cagggaccca ggagctgctg acattgctaa ttacctgat ggaacagatt caagatgact    1560
gcactgggga tgaagattac acctatttga ttctgcgggt cattggaaat atgggccaaa    1620
ccatggagca gttaactcca gaactcaagt cttcaatcct gaaatgtgtc caaagtacaa    1680
agccatcact gatgatccag aaagctgcca tccaggctct gcggaaaatg agcctaaag    1740 acaaggacca ggaggttctt cttcagactt tccttgatga tgcttctccg ggagataagc    1800
gactggctgc ctatcttatg ttgatgagga gtccttcaca ggcagatatt aacaaaattg    1860
tccaaattct accatgggaa cagaatgagc aagtgaagaa ctttgtggct tcccatattg    1920
ccaatatctt gaactcagaa gaattggata tccaagatct gaaaaagtta gtgaaagaag    1980
ctctgaaaga atctcaactt ccaactgtca tggacttcag aaaattctct cggaactatc    2040
aactctacaa atctgtttct cttccatcac ttgacccagc ctcagccaaa atagaaggga    2100
atcttatatt tgatccaaat aactaccttc ctaaagaaag catgctgaaa actaccctca    2160
ctgcctttgg atttgcttca gctgacctca tcgagattgg cttggaagga aaaggctttg    2220
agccaacatt ggaagctctt tttgggaagc aaggattttt cccagacagt gtcaacaaag    2280
ctttgtactg ggttaatggt caagttcctg atggtgtctc taaggtctta gtggaccact    2340
ttggctatac caaagatgat aaacatgagc aggatatggt aaatggaata atgctcagtg    2400
ttgagaagct gattaaagat ttgaaatcca agaagtccc ggaagccaga gcctacctcc    2460
gcatcttggg agaggagctt ggttttgcca gtctccatga cctccagctc ctgggaaagc    2520
tgcttctgat gggtgcccgc actctgcagg ggatccccca gatgattgga gaggtcatca    2580
ggaagggctc aaagaatgac tttttcttc actacatctt catggagaat gcctttgaac    2640
tccccactgg agctggatta cagttgcaaa tatcttcatc tggagtcatt gctcccggag    2700
ccaaggctgg agtaaaactg gaagtagcca acatgcaggc tgaactggtg caaaaccct    2760 ccgtgtctgt ggagtttgtg acaaatatgg gcatcatcat tccggacttc gctaggagtg    2820
gggtccagat gaacaccaac ttcttccacg agtcgggtct ggaggctcat gttgccctaa    2880
aagctgggaa gctgaagttt atcattcctt ccccaaagag accagtcaag ctgctcagtg    2940
gaggcaacac attacatttg gtctctacca ccaaaacgga ggtgatccca cctctcattg    3000
agaacaggca gtcctggtca gtttgcaagc aagtctttcc tggcctgaat tactgcacct    3060
caggcgctta ctccaacgcc agctccacag actccgcctc ctactatccg ctgaccgggg    3120
acaccagatt agagctggaa ctgaggccta caggagagat tgagcagtat tctgtcagcg    3180
caacctatga gctccagaga gaggacagag ccttggtgga tacccctgaag tttgtaactc    3240 aagcagaagg tgcgaagcag actgaggcta ccatgacatt caaatataat cggcagagta    3300
```

```
tgaccttgtc cagtgaagtc caaattccgg attttgatgt tgacctcgga acaatcctca    3360
gagttaatga tgaatctact gagggcaaaa cgtcttacag actcaccctg gacattcaga    3420
acaagaaaat tactgaggtc gccctcatgg gccacctaag ttgtgacaca aaggaagaaa    3480
gaaaaatcaa gggtgttatt tccataccccc gtttgcaagc agaagccaga agtgagatcc    3540
tcgcccactg gtcgcctgcc aaactgcttc tccaaatgga ctcatctgct acagcttatg    3600
gctccacagt ttccaagagg gtggcatggc attatgatga agagaagatt gaatttgaat    3660
ggaacacagg caccaatgta gataccaaaa aaatgacttc caatttccct gtggatctct    3720
ccgattatcc taagagcttg catatgtatg ctaatagact cctggatcac agagtccctc    3780
aaacagacat gactttccgg cacgtgggtt ccaaattaat agttgcaatg agctcatggc    3840
ttcagaaggc atctgggagt cttccttata cccagacttt gcaagaccac ctcaatagcc    3900
tgaaggagtt caacctccag aacatgggat tgccagactt ccacatccca gaaaacctct    3960
tcttaaaaag cgatggccgg gtcaaatata ccttgaacaa gaacagtttg aaaattgaga    4020
ttcctttgcc ttttggtggc aaatcctcca gagatctaaa gatgttagag actgttagga    4080
caccagccct ccacttcaag tctgtgggat tccatctgcc atctcgagag ttccaagtcc    4140
ctacttttac cattcccaag ttgtatcaac tgcaagtgcc tctcctgggt gttctagacc    4200
tctccacgaa tgtctacagc aacttgtaca actggtccgc ctcctacagt ggtggcaaca    4260
ccagcacaga ccatttcagc cttcgggctc gttaccacat gaaggctgac tctgtggttg    4320
acctgctttc ctacaatgtg caaggatctg agaaacaac atatgaccac aagaatacgt    4380
tcacactatc atgtgatggg tctctacgcc acaaatttct agattcgaat atcaaattca    4440
gtcatgtaga aaaacttgga aacaacccag tctcaaaagg tttactaata ttcgatgcat    4500
ctagttcctg gggaccacag atgtctgctt cagttcattt ggactccaaa agaaacagc    4560
atttgtttgt caaagaagtc aagattgatg ggcagttcag agtctcttcg ttctatgcta    4620
aaggcacata tggcctgtct tgtcagaggg atcctaacac tggccggctc aatggagagt    4680
ccaacctgag gtttaactcc tcctacctcc aaggcaccaa ccagataaca ggaagatatg    4740
aagatggaac cctctcccctc acctccacct ctgatctgca aagtggcatc attaaaaata    4800
ctgcttccct aaagtatgag aactacgagc tgactttaaa atctgacacc aatgggaagt    4860
ataagaactt tgccacttct aacaagatgg atatgacctt ctctaagcaa aatgcactgc    4920
tgcgttctga atatcaggct gattacgagt cattgaggtt ctttcagcctg ctttctggat    4980
cactaaattc ccatggtctt gagttaaatg ctgacatctt aggcactgac aaaattaata    5040
gtggtgctca caaggcgaca ctaaggattg gccaagatgg aatatctacc agtgcaacga    5100
ccaacttgaa gtgtagtctc ctggtgctgg agaatgagct gaatgcagag cttggcctct    5160
ctggggcatc tatgaaatta caacaaatg gccgcttcag ggaacacaat gcaaaattca    5220
gtctggatgg gaaagccgcc ctcacagagc tatcactggg aagtgcttat caggccatga    5280
ttctgggtgt cgacagcaaa aacatttca acttcaaggt cagtcaagaa ggacttaagc    5340
tctcaaatga catgatgggc tcatatgctg aaatgaaatt tgaccacaca aacagtctga    5400
acattgcagg cttatcactg gacttctctt caaaacttga acacatttac agctctgaca    5460
agttttataa gcaaactgtt aatttacagc tacagcccta ttctctggta actactttaa    5520
acagtgacct gaaatacaat gctctggatc tcaccaacaa tgggaaacta cggctagaac    5580
ccctgaagct gcatgtggct ggtaacctaa aaggagccta ccaaaataat gaaataaaac    5640
acatctatgc catctcttct gctgcctat cagcaagcta taaagcagac actgttgcta    5700
```

```
aggttcaggg tgtggagttt agccatcggc tcaacacaga catcgctggg ctggcttcag    5760
ccattgacat gagcacaaac tataattcag actcactgca tttcagcaat gtcttccgtt    5820
ctgtaatggc cccgtttacc atgaccatcg atgcacatac aaatggcaat gggaaactcg    5880
ctctctgggg agaacatact gggcagctgt atagcaaatt cctgttgaaa gcagaacctc    5940
tggcatttac tttctctcat gattacaaag gctccacaag tcatcatctc gtgtctagga    6000
aaagcatcag tgcagctctt gaacacaaag tcagtgccct gcttactcca gctgagcaga    6060
caggcacctg gaaactcaag acccaattta acaacaatga atacagccag gacttggatg    6120
cttacaacac taaagataaa attggcgtgg agcttactgg acgaactctg gctgacctaa    6180
ctctactaga ctccccaatt aaagtgccac ttttactcag tgagcccatc aatatcattg    6240
atgctttaga gatgagagat gccgttgaga agccccaaga atttacaatt gttgcttttg    6300
taaagtatga taaaaaccaa gatgttcact ccattaacct cccatttttt gagaccttgc    6360
aagaatattt tgagaggaat cgacaaacca ttatagttgt actggaaaac gtacagagaa    6420
acctgaagca catcaatatt gatcaatttg taagaaaata cagagcagcc ctgggaaaac    6480
tcccacagca agctaatgat tatctgaatt cattcaattg ggagagacaa gtttcacatg    6540
ccaaggagaa actgactgct ctcacaaaaa agtatagaat tacagaaaat gatatacaaa    6600
ttgcattaga tgatgccaaa atcaacttta atgaaaaact atctcaactg cagacatata    6660
tgatacaatt tgatcagtat attaaagata gttatgattt acatgatttg aaaatagcta    6720
ttgctaatat tattgatgaa atcattgaaa aattaaaaag tcttgatgag cactatcata    6780
tccgtgtaaa tttagtaaaa acaatccatg atctacattt gtttattgaa aatattgatt    6840
ttaacaaaag tggaagtagt actgcatcct ggattcaaaa tgtggatact aagtaccaaa    6900
tcagaatcca gatacaagaa aaactgcagc agcttaagag acacatacag aatatagaca    6960
tccagcacct agctggaaag ttaaacaac acattgaggc tattgatgtt agagtgcttt    7020
tagatcaatt gggaactaca atttcatttg aaagaataaa tgacgttctt gagcatgtca    7080
aacactttgt tataaatctt attggggatt ttgaagtagc tgagaaaatc aatgccttca    7140
gagccaaagt ccatgagtta atcgagaggt atgaagtaga ccaacaaatc caggttttaa    7200
tggataaatt agtagagttg gcccaccaat acaagttgaa ggagactatt cagaagctaa    7260
gcaatgtcct acaacaagtt aagataaaag attactttga gaaattggtt ggatttattg    7320
atgatgctgt caagaagctt aatgaattat cttttaaaac attcattgaa gatgttaaca    7380
aattccttga catgttgata aagaaattaa agtcatttga ttaccaccag tttgtagatg    7440
aaaccaatga caaaatccgt gaggtgactc agagactcaa tggtgaaatt caggctctgg    7500
aactaccaca aaaagctgaa gcattaaaac tgtttttaga ggaaaccaag gccacagttg    7560
cagtgtatct ggaaagccta caggacacca aaataacctt aatcatcaat tggttacagg    7620
aggctttaag ttcagcatct ttggctcaca tgaaggccaa attccgagag ccctagaag    7680 atacacgaga ccgaatgtat caaatggaca ttcagcagga acttcaacga tacctgtctc    7740
tggtaggcca ggtttatagc acacttgtca cctacatttc tgattggtgg actcttgctg    7800
ctaagaacct tactgacttt gcagagcaat attctatcca agattgggct aaacgtatga    7860
aagcattggt agagcaaggg ttcactgttc ctgaaatcaa gaccatcctt gggaccatgc    7920
ctgcctttga agtcagtctt caggctcttc agaaagctac cttccagaca cctgattta    7980 tagtcccccct aacagatttg aggattccat cagttcagat aaacttcaaa gacttaaaaa    8040
```

```
atataaaaat cccatccagg ttttccacac cagaatttac catccttaac accttccaca    8100
ttccttcctt tacaattgac tttgtagaaa tgaaagtaaa gatcatcaga accattgacc    8160
agatgctgaa cagtgagctg cagtggcccg ttccagatat atatctcagg gatctgaagg    8220
tggaggacat tcctctagcg agaatcaccc tgccagactt ccgtttacca gaaatcgcaa    8280
ttccagaatt cataatccca actctcaacc ttaatgattt tcaagttcct gaccttcaca    8340
taccagaatt ccagcttccc cacatctcac acacaattga agtacctact tttggcaagc    8400
tatacagtat tctgaaaatc caatctcctc ttttcacatt agatgcaaat gctgacatag    8460
ggaatggaac cacctcagca aacgaagcag gtatcgcagc ttccatcact gccaaaggag    8520
agtccaaatt agaagttctc aattttgatt ttcaagcaaa tgcacaactc tcaaacccta    8580
agattaatcc gctggctctg aaggagtcag tgaagttctc cagcaagtac ctgagaacgg    8640
agcatgggag tgaaatgctg ttttttggaa atgctattga gggaaaatca aacacagtgg    8700
caagtttaca cacagaaaaa aatacactgg agcttagtaa tggagtgatt gtcaagataa    8760
acaatcagct taccctggat agcaacacta aatacttcca caaattgaac atccccaaac    8820
tggacttctc tagtcaggct gacctgcgca acgagatcaa gacactgttg aaagctggcc    8880
acatagcatg gacttcttct ggaaaagggt catggaaatg ggcctgcccc agattctcag    8940
atgagggaac acatgaatca caaattagtt tcaccataga aggacccctc acttcctttg    9000
gactgtccaa taagatcaat agcaaacacc taagagtaaa ccaaaacttg gtttatgaat    9060
ctggctccct caacttttct aaacttgaaa ttcaatcaca agtcgattcc cagcatgtgg    9120
gccacagtgt tctaactgct aaaggcatgg cactgtttgg agaagggaag gcagagttta    9180
ctgggaggca tgatgctcat ttaaatggaa aggttattgg aactttgaaa aattctcttt    9240
tcttttcagc ccagccattt gagatcacgg catccacaaa caatgaaggg aatttgaaag    9300
ttcgttttcc attaaggtta acagggaaga tagacttcct gaataactat gcactgtttc    9360
tgagtcccag tgcccagcaa gcaagttggc aagtaagtgc taggttcaat cagtataagt    9420
acaaccaaaa tttctctgct ggaaacaacg agaacattat ggaggcccat gtaggaataa    9480
atggagaagc aaatctggat ttcttaaaca ttccttaaac aattcctgaa atgcgtctac    9540
cttacacaat aatcacaact cctccactga agatttctc tctatgggaa aaaacaggct    9600
tgaaggaatt cttgaaaacg acaaagcaat catttgattt aagtgtaaaa gctcagtata    9660
agaaaaacaa acacaggcat tccatcacaa atcctttggc tgtgctttgt gagtttatca    9720
gtcagagcat caaatccttt gacaggcatt ttgaaaaaaa cagaaacaat gcattagatt    9780
ttgtcaccaa atcctataat gaaacaaaaa ttaagtttga taagtacaaa gctgaaaaat    9840
ctcacgacga gctccccagg acctttcaaa ttcctggata cactgttcca gttgtcaatg    9900
ttgaagtgtc tccattcacc atagagatgt cggcattcgg ctatgtgttc ccaaaagcag    9960
tcagcatgcc tagtttctcc atcctaggtt ctgacgtccg tgtgccttca tacacattaa   10020
tcctgccatc attagagctg ccagtccttc atgtccctag aaatctcaag ctttctcttc   10080
cagatttcaa ggaattgtgt accataagcc atatttttat tcctgccatg gcaatatta   10140
cctatgattt ctccttttaaa tcaagtgtca tcacactgaa taccaatgct gaacttttta   10200
accagtcaga tattgttgct catctccttt cttcatcttc atctgtcatt gatgcactgc   10260
agtacaaatt agagggcacc acaagattga caagaaaaag gggattgaag ttagccacag   10320
ctctgtctct gagcaacaaa tttgtggagg gtagtcataa cagtactgtg agcttaacca   10380
cgaaaaatat ggaagtgtca gtggcaacaa ccacaaaagc ccaaattcca attttgagaa   10440
```

```
tgaatttcaa gcaagaactt aatggaaata ccaagtcaaa acctactgtc tcttcctcca  10500
tggaatttaa gtatgatttc aattcttcaa tgctgtactc taccgctaaa ggagcagttg  10560
accacaagct tagcttggaa agcctcacct cttactttc cattgagtca tctaccaaag   10620
gagatgtcaa gggttcggtt ctttctcggg aatattcagg aactattgct agtgaggcca  10680
acacttactt gaattccaag agcacacggt cttcagtgaa gctgcagggc acttccaaaa  10740
ttgatgatat ctggaacctt gaagtaaaag aaaattttgc tggagaagcc acactccaac  10800
gcatatattc cctctgggag cacagtacga aaaccactt acagctagag ggcctctttt   10860
tcaccaacgg agaacataca agcaaagcca ccctggaact ctctccatgg caaatgtcag  10920
ctcttgttca ggtccatgca agtcagccca gttccttcca tgatttccct gaccttggcc  10980
aggaagtggc cctgaatgct aacactaaga accagaagat cagatggaaa atgaagtcc   11040 ggattcattc tgggtctttc cagagccagg tcgagctttc caatgaccaa gaaaaggcac  11100
accttgacat tgcaggatcc ttagaaggac acctaaggtt cctcaaaaat atcatcctac  11160
cagtctatga caagagctta tgggatttcc taaagctgga tgtaaccacc agcattggta  11220
ggagacagca tcttcgtgtt tcaactgcct tgtgtacac caaaaacccc aatggctatt   11280
cattctccat ccctgtaaaa gttttggctg ataaattcat tattcctggg ctgaaactaa  11340
atgatctaaa ttcagttctt gtcatgccta cgttccatgt cccatttaca gatcttcagg  11400
ttccatcgtg caaacttgac ttcagagaaa tacaaatcta taagaagctg agaacttcat  11460
catttgccct caacctacca acactccccg aggtaaaatt ccctgaagtt gatgtgttaa  11520
caaaatattc tcaaccagaa gactccttga ttcccttttt tgagataacc gtgcctgaat  11580
ctcagttaac tgtgtcccag ttcacgcttc caaaaagtgt ttcagatggc attgctgctt  11640
tggatctaaa tgcagtagcc aacaagatcg cagactttga gttgcccacc atcatcgtgc  11700
ctgagcagac cattgagatt ccctccatta agttctctgt acctgctgga attgtcattc  11760
cttcctttca agcactgact gcacgctttg aggtagactc tcccgtgtat aatgccactt  11820
ggagtgccag tttgaaaaac aaagcagatt atgttgaaac agtcctggat tccacatgca  11880
gctcaaccgt acagttccta gaatatgaac taaatgtttt gggaacacac aaaatcgaag  11940
atggtacgtt agcctctaag actaaaggaa catttgcaca ccgtgacttc agtgcagaat  12000
atgaagaaga tggcaaatat gaaggacttc aggaatggga aggaaaagcg cacctcaata  12060
tcaaaagccc agcgttcacc gatctccatc tgcgctacca gaaagacaag aaaggcatct  12120
ccacctcagc agcctcccca gccgtaggca ccgtgggcat ggatatggat gaagatgacg  12180
acttttctaa atggaacttc tactacagcc ctcagtcctc tccagataaa aaactcacca  12240
tattcaaaac tgagttgagg gtccgggaat ctgatgagga aactcagatc aaagttaatt  12300
gggaagaaga ggcagcttct ggcttgctaa cctctctgaa agacaacgtg cccaaggcca  12360 cagggggtcct ttatgattat gtcaacaagt accactggga acacacaggg ctcaccctga  12420
gagaagtgtc ttcaaagctg agaagaaatc tgcagaacaa tgctgagtgg gtttatcaag  12480
gggccattag gcaaattgat gatatcgacg tgaggttcca gaaagcagcc agtggcacca  12540
ctgggaccta ccaagagtgg aaggacaagg cccagaatct gtaccaggaa ctgttgactc  12600
aggaaggcca agccagtttc cagggactca aggataacgt gtttgatggc ttggtacgag  12660
ttactcaaga attccatatg aaagtcaagc atctgattga ctcactcatt gattttctga  12720 acttcccag attccagttt ccggggaaac ctgggatata cactagggag gaactttgca  12780
```

```
ctatgttcat aagggaggta gggacggtac tgtcccaggt atattcgaaa gtccataatg    12840
gttcagaaat actgttttcc tatttccaag acctagtgat tacacttcct ttcgagttaa    12900
ggaaacataa actaatagat gtaatctcga tgtataggga actgttgaaa gatttatcaa    12960
aagaagccca agaggtattt aaagccattc agtctctcaa gaccacagag gtgctacgta    13020
atcttcagga ccttttacaa ttcattttcc aactaataga agataacatt aaacagctga    13080
aagagatgaa atttacttat cttattaatt atatccaaga tgagatcaac acaatcttca    13140
gtgattatat cccatatgtt tttaaattgt tgaaagaaaa cctatgcctt aatcttcata    13200
agttcaatga atttattcaa aacgagcttc aggaagcttc tcaagagtta cagcagatcc    13260
atcaatacat tatggcccct cgtgaagaat attttgatcc aagtatagtt ggctggacag    13320
tgaaatatta tgaacttgaa gaaaagatag tcagtctgat caagaacctg ttagttgctc    13380
ttaaggactt ccattctgaa tatattgtca gtgcctctaa ctttacttcc caactctcaa    13440
gtcaagttga gcaatttctg cacagaaata ttcaggaata tcttagcatc cttaccgatc    13500
cagatggaaa agggaaagag aagattgcag agctttctgc cactgctcag gaaataatta    13560
aaagccaggc cattgcgacg aagaaaataa tttctgatta ccaccagcag tttagatata    13620
aactgcaaga ttttttcagac caactctctg attactatga aaaatttatt gctgaatcca    13680
aaagattgat tgacctgtcc attcaaaact accacacatt tctgatatac atcacggagt    13740
tactgaaaaa gctgcaatca accacagtca tgaaccccta catgaagctt gctccaggag    13800
aacttactat catcctctaa ttttttaaaa gaaatcttca tttattcttc ttttccaatt    13860
gaactttcac atagcacaga aaaaattcaa actgcctata ttgataaaac catacagtga    13920
gccagccttg cagtaggcag tagactataa gcagaagcac atatgaactg gacctgcacc    13980 aaaagctggca ccagggctcg gaaggtctct gaactcagaa ggatggcatt ttttgcaagt    14040
taaagaaaat caggatctga gttatttgc taaacttggg ggaggaggaa caaataaatg    14100
gagtctttat tgtgtatcat a                                             14121

<210> SEQ ID NO 53
<211> LENGTH: 2759
<212> TYPE: DNA
<213> ORGANISM: Homo sapiens

<400> SEQUENCE: 53
gctcaggccc cgcccctgcc gccggaatcc tgaagcccaa ggctgccgg gggcggtccg      60 gcggcgccgg cgatggggca taaaaccact ggccacctgc cgggctgctc ctgcgtgcgc    120
tgccgtcccg gatccaccgt gcctctgcgg cctgcgtgcc cggagtcccc gcctgtgtcg    180
tctctgtcgc cgtccccgtc tcctgccagg cgcggagccc tgcgagccgc gggtgggccc    240
caggcgcgca gacatgggct gctccgccaa agcgcgctgg gctgccgggg cgctgggcgt    300 cgcgggggcta ctgtgcgctg tgctgggcgc tgtcatgatc gtgatggtgc cgtcgctcat    360
caagcagcag gtccttaaga acgtgcgcat cgaccccagt agcctgtcct tcaacatgtg    420
gaaggagatc cctatcccct tctatctctc cgtctacttc tttgacgtca tgaaccccag    480
cgagatcctg aagggcgaga gccgcaggt gcggagcgc gggccctacg tgtacaggga    540
gttcaggcac aaaagcaaca tcaccttcaa caacaacgac accgtgtcct tcctcgagta    600
ccgcaccttc cagttccagc cctccaagtc ccacggctcg gagagcgact acatcgtcat    660
gcccaacatc ctggtcttgg gtgcggcggt gatgatggag aataagccca tgaccctgaa    720
gctcatcatg accttggcat tcaccaccct cggcgaacgt gccttcatga accgcactgt    780
```

```
gggtgagatc atgtggggct acaaggaccc ccttgtgaat ctcatcaaca agtactttcc      840
aggcatgttc cccttcaagg acaagttcgg attatttgct gagctcaaca actccgactc      900
tgggctcttc acggtgttca cgggggtcca gaacatcagc aggatccacc tcgtggacaa      960
gtggaacggg ctgagcaagg ttgacttctg gcattccgat cagtgcaaca tgatcaatgg     1020
aacttctggg caaatgtggc cgcccttcat gactcctgag tcctcgctgg agttctacag     1080
cccggaggcc tgccgatcca tgaagctaat gtacaaggag tcaggggtgt ttgaaggcat     1140
ccccacctat cgcttcgtgg ctcccaaaac cctgtttgcc aacgggtcca tctacccacc     1200
caacgaaggc ttctgcccgt gcctggagtc tggaattcag aacgtcagca cctgcaggtt     1260
cagtgccccc ttgtttctct cccatcctca cttcctcaac gctgaccggg ttctggcaga     1320
agcggtgact ggcctgcacc ctaaccagga ggcacactcc ttgttcctgg acatccaccc     1380
ggtcacggga atccccatga actgctctgt gaaactgcag ctgagcctct acatgaaatc     1440
tgtcgcagga attggacaaa ctgggaagat tgagcctgtg gtcctgccgc tgctctggtt     1500
tgcagagagc ggggccatgg agggggagac tcttcacaca ttctacactc agctggtgtt     1560
gatgcccaag gtgatgcact atgcccagta cgtcctcctg gcgctgggct gcgtcctgct     1620
gctggtccct gtcatctgcc aaatccggag ccaagagaaa tgctatttat tttggagtag     1680
tagtaaaaag ggctcaaagg ataaggaggc cattcaggcc tattctgaat ccctgatgac     1740
atcagctccc aagggctctg tgctgcagga agcaaaactg tagggtcctg aggacaccgt     1800
gagccagcca ggcctggccg ctgggcctga ccggcccccc agcccctaca cccgcttct      1860 cccggactct cccagcggac agcccccag ccccacagcc tgagcctccc agctgccatg      1920
tgcctgttgc acacctgcac acacgccctg gcacacatac acacatgcgt gcaggcttgt     1980
gcagacactc agggatggag ctgctgctga agggacttgt agggagaggc tcgtcaacaa     2040
gcactgttct ggaaccttct ctccacgtgg cccacaggcc tgaccacagg gctgtgggt      2100 cctgcgtccc cttcctcggg tgagcctggc ctgtcccgtt cagccgttgg gcccaggctt     2160
cctcccctcc aaggtgaaac actgcagtcc cggtgtggtg gctccccatg caggacgggc     2220
caggctggga gtgccgcctt cctgtgccaa attcagtggg gactcagtgc ccaggccctg     2280
gccacgagct ttggccttgg tctacctgcc aggccaggca aagcgccttt acacaggcct     2340
cggaaaacaa tggagtgagc acaagatgcc ctgtgcagct gcccgagggt ctccgcccac     2400
cccggccgga cttgatcccc ccgaagtctt cacaggcac tgcatcgggt tgtctggcgc      2460
ccttttcctc cagcctaaac tgacatcatc ctatggactg agccggccac tctctggccg     2520
aagtggccgc aggctgtgcc cccgagctgc ccccacccc tcacagggtc cctcagatta      2580
taggtgccca ggctgaggtg aagaggcctg ggggccctgc cttccgggcg ctcctggacc     2640
ctggggcaaa cctgtgaccc ttttctactg gaatagaaat gagttttatc atctttgaaa     2700
aataattcac tcttgaagta ataaacgttt aaaaaatgg gaaaaaaaa aaaaaaaa        2759
```

<210> SEQ ID NO 54
<211> LENGTH: 8758
<212> TYPE: DNA
<213> ORGANISM: Homo sapiens

<400> SEQUENCE: 54

```
gtaaaggact ggggcccgc aactggcctc tcctgccctc ttaagcgcag cgccatttta      60
gcaacgcaga agcccggcgc cgggaagcct cagctcgcct gaaggcaggt cccctctgac    120
```

-continued

| | |
|---|---|
| gcctccggga gcccaggttt cccagagtcc ttgggacgca gcgacgagtt gtgctgctat | 180 |
| cttagctgtc cttataggct ggccattcca ggtggtggta tttagataaa accactcaaa | 240 |
| ctctgcagtt tggtcttggg gtttggagga aagcttttat ttttcttcct gctccggttc | 300 |
| agaaggtctg aagctcatac ctaaccaggc ataacacaga atctgcaaaa caaaaacccc | 360 |
| taaaaagca gacccagagc agtgtaaaca cttctgggtg tgtccctgac tggctgccca | 420 |
| aggtctctgt gtcttcggag acaaagccat tcgcttagtt ggtctacttt aaaaggccac | 480 |
| ttgaactcgc tttccatggc gatttgcctt gtgagcactt tcaggagagc ctggaagctg | 540 |
| aaaaacggta gaaaaatttc cgtgcgggcc gtgggggggct ggcggcaact ggggggccgc | 600 |
| agatcagagt gggccactgg cagccaacgg cccccggggc tcaggcgggg agcagctctg | 660 |
| tggtgtggga ttgaggcgtt ttccaagagt gggttttcac gtttctaaga tttcccaagc | 720 |
| agacagcccg tgctgctccg atttctcgaa caaaaaagca aaacgtgtgg ctgtcttggg | 780 |
| agcaagtcgc aggactgcaa gcagttgggg gagaaagtcc gccattttgc cacttctcaa | 840 |
| ccgtccctgc aaggctgggg ctcagttgcg taatggaaag taaagccctg aactatcaca | 900 |
| cttttaatctt ccttcaaaag gtggtaaact atacctactg tccctcaaga aacacaaga | 960 |
| agtgctttaa gaggtatttt aaaagttccg ggggttttgt gaggtgtttg atgacccgtt | 1020 |
| taaaatatga tttccatgtt tcttttgtct aaagtttgca gctcaaatct ttccacacgc | 1080 |
| tagtaattta agtatttctg catgtgtagt ttgcattcaa gttccataag ctgttaagaa | 1140 |
| aaatctagaa aagtaaaact agaacctatt tttaaccgaa gaactacttt ttgcctccct | 1200 |
| cacaaaggcg gcgaaggtg atcgaattcc ggtgatgcga gttgttctcc gtctataaat | 1260 |
| acgcctcgcc cgagctgtgc ggtaggcatt gaggcagcca gcgcaggggc ttctgctgag | 1320 |
| ggggcaggcg gagcttgagg aaaccgcaga taagttttt tctctttgaa agatagagat | 1380 |
| taatacaact acttaaaaaa tatagtcaat aggttactaa gatattgctt agcgttaagt | 1440 |
| ttttaacgta atttttaatag cttaagattt taagagaaaa tatgaagact agaagagta | 1500 |
| gcatgaggaa ggaaaagata aaaggtttct aaaacatgac ggaggttgag atgaagcttc | 1560 |
| ttcatggagt aaaaaatgta tttaaaagaa aattgagaga aaggactaca gagccccgaa | 1620 |
| ttaataccaa tagaagggca atgcttttag attaaaatga aggtgactta aacagcttaa | 1680 |
| agtttagttt aaaagttgta ggtgattaaa ataatttgaa ggcgatcttt taaaagaga | 1740 |
| ttaaaccgaa ggtgattaaa agaccttgaa atccatgacg cagggagaat tgcgtcattt | 1800 |
| aaagcctagt taacgcattt actaaacgca gacgaaaatg gaaagattaa ttgggagtgg | 1860 |
| taggatgaaa caatttggag aagatagaag tttgaagtgg aaaactggaa gacagaagta | 1920 |
| cgggaaggcg aagaaaagaa tagagaagat agggaaatta aagataaaa acatactttt | 1980 |
| agaagaaaaa agataaattt aaacctgaaa agtaggaagc agaagaaaaa agacaagcta | 2040 |
| ggaaacaaaa agctaagggc aaaatgtaca aacttagaag aaaattggaa gatagaaaca | 2100 |
| agatagaaaa tgaaaatatt gtcaagagtt tcagatagaa aatgaaaaac aagctaagac | 2160 |
| aagtattgga gaagtataga agatagaaaa atataaagcc aaaaattgga taaaatagca | 2220 |
| ctgaaaaaat gaggaaatta ttggtaacca atttatttta aaagcccatc aatttaattt | 2280 |
| ctggtggtgc agaagttaga aggtaaagct tgagaagatg agggtgttta cgtagaccag | 2340 |
| aaccaattta gaagaatact tgaagctaga aggggaagtt ggttaaaaat cacatcaaaa | 2400 |
| agctactaaa aggactggtg taatttaaaa aaaactaagg cagaaggctt ttggaagagt | 2460 |
| tagaagaatt tggaaggcct taaatatagt agcttagttt gaaaaatgtg aaggactttc | 2520 |

```
gtaacggaag taattcaaga tcaagagtaa ttaccaactt aatgttttg cattggactt      2580 tgagttaaga ttatttttta aatcctgagg actagcatta attgacagct gacccaggtg      2640
ctacacagaa gtggattcag tgaatctagg aagacagcag cagacaggat tccaggaacc      2700
agtgtttgat gaagctagga ctgaggagca agcgagcaag cagcagttcg tggtgaagat      2760
aggaaaagag tccaggagcc agtgcgattt ggtgaaggaa gctaggaaga aggaaggagc      2820
gctaacgatt tggtggtgaa gctaggaaaa aggattccag gaaggagcga gtgcaatttg      2880
gtgatgaagg tagcaggcgg cttggcttgg caaccacacg gaggaggcga gcaggcgttg      2940
tgcgtagagg atcctagacc agcatgccag tgtgccaagg ccacagggaa agcgagtggt      3000
tggtaaaaat ccgtgaggtc ggcaatatgt tgttttctg gaacttactt atggtaacct      3060
tttatttatt ttctaatata atgggggagt tcgtactga ggtgtaaagg gatttatatg       3120
gggacgtagg ccgatttccg ggtgttgtag gtttctcttt ttcaggctta tactcatgaa      3180
tcttgtctga agcttttgag ggcagactgc caagtcctgg agaaatagta gatggcaagt      3240
ttgtgggttt ttttttttta cacgaatttg aggaaaacca aatgaatttg atagccaaat      3300
tgagacaatt tcagcaaatc tgtaagcagt ttgtatgttt agttgggta atgaagtatt       3360 tcagttttgt gaatagatga cctgttttta cttcctcacc ctgaattcgt tttgtaaatg      3420
tagagtttgg atgtgtaact gaggcggggg ggagttttca gtattttttt ttgtgggggt      3480
gggggcaaaa tatgttttca gttctttttc ccttaggtct gtctagaatc ctaaaggcaa      3540
atgactcaag gtgtaacaga aaacaagaaa atccaatatc aggataatca gaccaccaca      3600
ggtttacagt ttatagaaac tagagcagtt ctcacgttga ggtctgtgga agagatgtcc      3660
attggagaaa tggctggtag ttactctttt tcccccccac cccctaatc agactttaaa       3720 agtgcttaac cccttaaact tgttatttt tacttgaagc attttgggat ggtcttaaca       3780
gggaagagag agggtggggg agaaaatgtt tttttctaag attttccaca gatgctatag      3840
tactattgac aaactggggtt agagaaggag tgtaccgctg tgctgttggc acgaacacct     3900
tcagggactg gagctgcttt tatccttgga agagtattcc cagttgaagc tgaaaagtac      3960
agcacagtgc agctttggtt catattcagt catctcagga gaacttcaga agagcttgag      4020
taggccaaat gttgaagtta agttttccaa taatgtgact tcttaaaagt tttattaaag      4080
gggaggggca atattggca attagttggc agtggcctgt tacggttggg attggtgggg      4140
tgggtttagg taattgttta gtttatgatt gcagataaac tcatgccaga gaacttaaag      4200
tcttagaatg gaaaaagtaa agaaatatca acttccaagt tggcaagtaa ctcccaatga      4260
tttagttttt ttcccccag tttgaattgg gaagctgggg gaagttaaat atgagccact       4320
gggtgtacca gtgcattaat ttgggcaagg aaagtgtcat aatttgatac tgtatctgtt      4380
ttccttcaaa gtatagagct tttggggaag gaaagtattg aactgggggt tggtctggcc      4440
tactgggctg acattaacta caattatggg aaatgcaaaa gttgtttgga tatggtagtg      4500
tgtggttctc ttttggaatt ttttttcaggt gatttaataa taatttaaaa ctactataga     4560
aactgcagag caaaggaagt ggcttaatga tcctgaaggg atttcttctg atggtagctt      4620
ttgtattatc aagtaagatt ctattttcag ttgtgtgtaa gcaagttttt ttttagtgta      4680
ggagaaatac ttttccattg tttaactgca aaacaagatg ttaaggtatg cttcaaaaat      4740
tttgtaaatt gttatttta aacttatctg tttgtaaatt gtaactgatt aagaattgtg      4800
atagttcagc ttgaatgtct cttagagggt gggcttttgt tgatgaggga ggggaaactt     4860
```

```
ttttttttttc tatagactttt tttcagataa catcttctga gtcataacca gcctggcagt    4920
atgatggcct agatgcagag aaaacagctc cttggtgaat tgataagtaa aggcagaaaa    4980
gattatatgt catacctcca ttggggaata agcataaccc tgagattctt actactgatg    5040
agaacattat ctgcatatgc caaaaaattt taagcaaatg aaagctacca atttaaagtt    5100
acggaatcta ccattttaaa gttaattgct tgtcaagcta taaccacaaa aataatgaat    5160
tgatgagaaa tacaatgaag aggcaatgtc catctcaaaa tactgctttt acaaaagcag    5220
aataaaagcg aaagaaatg aaaatgttac actacattaa tcctggaata aagaagccg    5280 aaataaatga gagatgagtt gggatcaagt ggattgagga ggctgtgctg tgtgccaatg    5340
tttcgtttgc ctcagacagg tatctcttcg ttatcagaag agttgcttca tttcatctgg    5400
gagcagaaaa cagcaggcag ctgttaacag ataagtttaa cttgcatctg cagtattgca    5460
tgttagggat aagtgcttat ttttaagagc tgtggagttc ttaaatatca accatggcac    5520
tttctcctga ccccttccct aggggatttc aggattgaga aattttttcca tcgagccttt    5580 ttaaaattgt aggacttgtt cctgtgggct tcagtgatgg gatagtacac ttcactcaga    5640
ggcatttgca tctttaaata atttcttaaa agcctctaaa gtgatcagtg ccttgatgcc    5700
aactaaggaa atttgtttag cattgaatct ctgaaggctc tatgaaagga atagcatgat    5760
gtgctgttag aatcagatgt tactgctaaa atttacatgt tgtgatgtaa attgtgtaga    5820
aaaccattaa atcattcaaa ataataaact attttattta gagaatgtat acttttagaa    5880
agctgtctcc ttatttaaat aaaatagtgt ttgtctgtag ttcagtgttg gggcaatctt    5940
gggggggatt cttctctaat cttcagaaa ctttgtctgc gaacactctt taatggacca    6000
gatcaggatt tgagcggaag aacgaatgta actttaaggc aggaaagaca aattttattc    6060
ttcataaagt gatgagcata taataattcc aggcacatgg caatagaggc cctctaaata    6120
aggaataaat aacctcttag acaggtggga gattatgatc agagtaaaag gtaattacac    6180
attttatttc cagaaagtca ggggtctata aattgacagt gattagagta atactttttc    6240
acatttccaa agtttgcatg ttaactttaa atgcttacaa tcttagagtg gtaggcaatg    6300
ttttacacta ttgaccttat ataggaagg gaggggtgc ctgtgggtt ttaaagaatt    6360 ttcctttgca gaggcatttc atccttcatg aagccattca ggattttgaa ttgcatatga    6420
gtgcttggct cttccttctg ttctagtgag tgtatgagac cttgcagtga gtttatcagc    6480
atactcaaaa ttttttttcct ggaatttgga gggatgggag gaggggtgg ggcttacttg    6540 ttgtagcttt tttttttttt acagacttca cagagaatgc agttgtcttg acttcaggtc    6600
tgtctgttct gttggcaagt aaatgcagta ctgttctgat cccgctgcta ttagaatgca    6660
ttgtgaaacg actggagtat gattaaaagt tgtgttcccc aatgcttgga gtagtgattg    6720
ttgaaggaaa aaatccagct gagtgataaa ggctgagtgt tgaggaaatt tctgcagttt    6780
taagcagtcg tatttgtgat tgaagctgag tacattttgc tggtgtattt ttaggtaaaa    6840 tgcttttttgt tcatttctgg tggtgggagg ggactgaagc ctttagtctt ttccagatgc    6900
aaccttaaaa tcagtgacaa gaaacattcc aaacaagcaa cagtcttcaa gaaattaaac    6960
tggcaagtgg aaatgtttaa acagttcagt gatcttagt gcattgttta tgtgtgggtt    7020
tctctctccc ctcccttggt cttaattctt acatgcagga acactcagca gacacacgta    7080
tgcgaagggc cagagaagcc agacccagta agaaaaaata gcctatttac tttaaataaa    7140
ccaaacattc cattttaaat gtggggattg ggaaccacta gttctttcag atggtattct    7200
tcagactata gaaggagctt ccagttgaat tcaccagtgg acaaaatgag gaaaacaggt    7260
```

```
gaacaagctt tttctgtatt tacatacaaa gtcagatcag ttatgggaca atagtattga    7320
atagatttca gctttatgct ggagtaactg gcatgtgagc aaactgtgtt ggcgtggggg    7380
tggaggggtg aggtgggcgc taagcctttt tttaagattt ttcaggtacc cctcactaaa    7440
ggcaccgaag gcttaaagta ggacaaccat ggagccttcc tgtggcagga gagacaacaa    7500
agcgctatta tcctaaggtc aagagaagtg tcagcctcac ctgatttttta ttagtaatga   7560 ggacttgcct caactccctc tttctggagt gaagcatccg aaggaatgct tgaagtaccc    7620
ctgggcttct cttaacattt aagcaagctg ttttttatagc agctcttaat aataaagccc   7680
aaatctcaag cggtgcttga aggggaggga aaggggaaa gcgggcaacc acttttccct     7740
agcttttcca gaagcctgtt aaaagcaagg tctccccaca agcaacttct ctgccacatc    7800
gccaccccgt gccttttgat ctagcacaga cccttcaccc ctcacctcga tgcagccagt    7860
agcttggatc cttgtgggca tgatccataa tcggtttcaa ggtaacgatg gtgtcgaggt    7920
cttggtgggg ttgaactatg ttagaaaagg ccattaattt gcctgcaaat tgttaacaga    7980
agggtattaa aaccacagct aagtagctct attataatac ttatccagtg actaaaacca    8040 acttaaaacca gtaagtggag aaataacatg ttcaagaact gtaatgctgg gtgggaacat   8100
gtaacttgta gactggagaa gataggcatt tgagtggctg agagggcttt tgggtgggaa    8160
tgcaaaaatt ctctgctaag acttttttcag gtgaacataa cagacttggc caagctagca  8220
tcttagcgga agctgatctc caatgctctt cagtagggtc atgaaggttt ttcttttcct    8280
gagaaaacaa cacgtattgt tttctcaggt tttgcttttt ggcctttttc tagcttaaaa    8340
aaaaaaaaag caaaagatgc tggtggttgg cactcctggt ttccaggacg gggttcaaat    8400
ccctgcggcg tctttgcttt gactactaat ctgtcttcag gactctttct gtatttctcc    8460 tttttctctgc aggtgctagt tcttggagtt ttggggaggt gggaggtaac agcacaatat   8520
ctttgaacta tatacatcct tgatgtataa tttgtcagga gcttgacttg attgtatatt    8580
catatttaca cgagaaccta atataactgc cttgtctttt tcaggtaata gcctgcagct    8640
ggtgttttga gaagccctac tgctgaaaac ttaacaattt tgtgtaataa aaatggagaa    8700
gctctaaatt gttgtggttc ttttgtgaat aaaaaaatct tgattgggga aaaaaaa      8758
```

<210> SEQ ID NO 55
<211> LENGTH: 5864
<212> TYPE: DNA
<213> ORGANISM: Homo sapiens

<400> SEQUENCE: 55

```
acaagtcttt ccgcctcccc agcccgcccg ggagctgcga gccgcgagct ggattatggt     60
ggcctgagca gccaacgcag ccgcaggagc ccggagccct tgcccctgcc cgcgccgccg    120
cccgccgggg ggaccaggga agccgccacc ggcccgccat gcccgcccct cccagccccg    180
ccgggagccc gcgccgcctg cccaggctgg ccgccgccgt gccgatgtag cgggctccgg    240
atcccagcct ctcccctgct cccgtgctct gcggatctcc cctgaccgct ctccacagcc    300
cggacccggg ggctgcccca gggccctgca ggccctggcg tcctgatgcc ccaagctcc     360 ctctcctgag aagccaccag caccacccag acttgggggg aggcgccagg gacggacgtg    420
ggccagtgcg agcccagagg gcccgaaggc cggggcccac catggcccaa gccctgccct    480
ggctcctgct gtggatgggc gcgggagtgc tgcctgccca cggcacccag cacggcatcc    540
ggctgcccct gcgcagcggc ctgggggggcg ccccccctggg gctgcggctg ccccgggaga  600
```

```
ccgacgaaga gcccgaggag cccggccgga ggggcagctt tgtggagatg gtggacaacc    660
tgagggggcaa gtcggggcag ggctactacg tggagatgac cgtgggcagc cccccgcaga    720
cgctcaacat cctggtggat acaggcagca gtaactttgc agtgggtgct gccccccacc    780
ccttcctgca tcgctactac cagaggcagc tgtccagcac ataccgggac ctccggaagg    840
gtgtgtatgt gccctacacc cagggcaagt gggaagggga gctgggcacc gacctggtaa    900
gcatccccca tggccccaac gtcactgtgc gtgccaacat tgctgccatc actgaatcag    960
acaagttctt catcaacggc tccaactggg aaggcatcct ggggctggcc tatgctgaga   1020
ttgccaggcc tgacgactcc ctggagcctt tctttgactc tctggtaaag cagacccacg   1080
ttcccaacct cttctccctg cagctttgtg gtgctggctt ccccctcaac cagtctgaag   1140
tgctggcctc tgtcggaggg agcatgatca ttggaggtat cgaccactcg ctgtacacag   1200
gcagtctctg gtatacaccc atccggcggg agtggtatta tgaggtgatc attgtgcggg   1260
tggagatcaa tggacaggat ctgaaaatga ctgcaagga gtacaactat gacaagagca   1320
ttgtggacag tggcaccacc aaccttcgtt tgcccaagaa agtgtttgaa gctgcagtca   1380
aatccatcaa ggcagcctcc tccacggaga agttccctga tggtttctgg ctaggagagc   1440
agctggtgtg ctggcaagca ggcaccaccc cttggaacat tttcccagtc atctcactct   1500
acctaatggg tgaggttacc aaccagtcct tccgcatcac catccttccg cagcaatacc   1560
tgcggccagt ggaagatgtg gccacgtccc aagacgactg ttacaagttt gccatctcac   1620
agtcatccac gggcactgtt atgggagctg ttatcatgga gggcttctac gttgtctttg   1680
atcgggcccg aaaacgaatt ggcttttgctg tcagcgcttg ccatgtgcac gatgagttca   1740
ggacggcagc ggtggaaggc ccttttgtca ccttggacat ggaagactgt ggctacaaca   1800
ttccacagac agatgagtca accctcatga ccatagccta tgtcatggct gccatctgcg   1860
ccctcttcat gctgccactc tgcctcatgg tgtgtcagtg gcgctgcctc cgctgcctgc   1920
gccagcagca tgatgacttt gctgatgaca tctcccctgct gaagtgagga ggcccatggg   1980
cagaagatag agattcccct ggaccacacc tccgtggttc actttggtca caagtaggag   2040
acacagatgg cacctgtggc cagagcacct caggaccctc cccacccacc aaatgcctct   2100
gccttgatgg agaaggaaaa ggctggcaag gtgggttcca gggactgtac ctgtaggaaa   2160
cagaaaagaa gaaagaag cactctgctg gcgggaatac tcttggtcac ctcaaattta   2220
agtcgggaaa ttctgctgct tgaaacttca gccctgaacc tttgtccacc attcctttaa   2280
attctccaac ccaaagtatt cttcttttct tagtttcaga agtactggca tcacacgcag   2340
gttaccttgg cgtgtgtccc tgtggtaccc tggcagagaa gagaccaagc ttgtttccct   2400
gctggccaaa gtcagtagga gaggatgcac agtttgctat ttgctttaga gacagggact   2460
gtataaacaa gcctaacatt ggtgcaaaga ttgcctcttg aattaaaaaa aaaaactaga   2520
ttgactattt atacaaatgg gggcggctgg aaagaggaga aggagaggga gtacaaagac   2580
agggaatagt gggatcaaag ctaggaaagg cagaaacaca accactcacc agtcctagtt   2640
ttagacctca tctccaagat agcatcccat ctcagaagat gggtgttgtt ttcaatgttt   2700
tcttttctgt ggttgcagcc tgaccaaaag tgagatggga agggcttatc tagccaaaga   2760
gctctttttt agctctctta aatgaagtgc ccactaagaa gttccactta acacatgaat   2820
ttctgccata ttaatttcat tgtctctatc tgaaccaccc tttattctac atatgatagg   2880
cagcactgaa atatcctaac cccctaagct ccaggtgccc tgtgggagag caactggact   2940
atagcagggc tgggctctgt cttcctggtc ataggctcac tctttccccc aaatcttcct   3000
```

```
ctggagctttt gcagccaagg tgctaaaagg aataggtagg agacctcttc tatctaatcc    3060
ttaaaagcat aatgttgaac attcattcaa cagctgatgc cctataaccc ctgcctggat    3120
ttcttcctat taggctataa gaagtagcaa gatctttaca taattcagag tggtttcatt    3180
gccttcctac cctctctaat ggcccctcca tttatttgac taaagcatca cacagtggca    3240
ctagcattat accaagagta tgagaaatac agtgctttat ggctctaaca ttactgcctt    3300
cagtatcaag gctgcctgga gaaggatgg cagcctcagg gcttccttat gtcctccacc    3360
acaagagctc cttgatgaag gtcatctttt tcccctatcc tgttcttccc ctccccgctc    3420
ctaatggtac gtgggtaccc aggctggttc ttgggctagg tagtggggac caagttcatt    3480
acctccctat cagttctagc atagtaaact acggtaccag tgttagtggg aagagctggg    3540
ttttcctagt atcccactg catcctactc ctacctggtc aacccgctgc ttccaggtat    3600
gggacctgct aagtgtggaa ttacctgata agggagaggg aaatacaagg agggcctctg    3660
gtgttcctgg cctcagccag ctgcccacaa gccataaacc aataaaacaa gaatactgag    3720
tcagtttttt atctgggttc tcttcattcc cactgcactt ggtgctgctt tggctgactg    3780
ggaacacccc ataactacag agtctgacag gaagactgga gactgtccac ttctagctcg    3840
gaacttactg tgtaaataaa cttttcagaac tgctaccatg aagtgaaaat gccacatttt    3900
gctttataat ttctacccat gttgggaaaa actggctttt tcccagccct ttccagggca    3960
taaaactcaa ccccttcgat agcaagtccc atcagcctat tatttttta aagaaaactt    4020 gcacttgttt ttctttttac agttacttcc ttcctgcccc aaaattataa actctaagtg    4080 taaaaaaag tcttaacaac agcttcttgc ttgtaaaaat atgtattata catctgtatt    4140
tttaaattct gctcctgaaa aatgactgtc ccattctcca ctcactgcat tggggccttt    4200
tcccattggt ctgcatgtct tttatcattg caggccagtg gacagaggga gaagggagaa    4260
caggggtcgc caacacttgt gttgctttct gactgatcct gaacaagaaa gagtaacact    4320
gaggcgctcg ctcccatgca caactctcca aaacacttat cctcctgcaa gagtgggctt    4380
tccagggtct ttactgggaa gcagttaagc cccctcctca cccttccttt tttctttct    4440 ttactccttt ggcttcaaag gattttggaa agaaacaat atgctttaca ctcattttca    4500
atttctaaat ttgcagggga tactgaaaaa tacggcaggt ggcctaaggc tgctgtaaag    4560
ttgaggggag aggaaatctt aagattacaa gataaaaaac gaatcccta aacaaaaga    4620 acaatagaac tggtcttcca ttttgccacc tttcctgttc atgacagcta ctaacctgga    4680
gacagtaaca tttcattaac caaagaaagt gggtcacctg acctctgaag agctgagtac    4740
tcaggccact ccaatcaccc tacaagatgc caaggaggtc ccaggaagtc cagctcctta    4800
aactgacgct agtcaataaa cctgggcaag tgaggcaaga gaaatgagga agaatccatc    4860
tgtgaggtga caggcaagga tgaaagacaa agaaggaaaa gagtatcaaa ggcagaaagg    4920
agatcattta gttgggtctg aaaggaaaag tctttgctat ccgacatgta ctgctagtac    4980
ctgtaagcat tttaggtccc agaatggaaa aaaaaatcag ctattggtaa tataataatg    5040
tcctttccct ggagtcagtt ttttaaaaa gttaactctt agttttact tgtttaattc    5100 taaaagagaa gggagctgag gccattccct gtaggagtaa agataaaagg ataggaaaag    5160
attcaaagct ctaatagagt cacagctttc ccaggtataa aacctaaaat taagaagtac    5220
aataagcaga ggtggaaaat gatctagttc ctgatagcta cccacagagc aagtgattta    5280
taaatttgaa atccaaacta ctttcttaat atcactttgg tctccatttt tcccaggaca    5340
```

```
ggaaatatgt ccccccctaa ctttcttgct tcaaaaatta aaatccagca tcccaagatc      5400
attctacaag taattttgca cagacatctc ctcaccccag tgcctgtctg agctcaccc       5460 aaggtcacca acaacttgg ttgtgaacca actgccttaa ccttctgggg aggggggatt      5520
agctagacta ggagaccaga agtgaatggg aaagggtgag gacttcacaa tgttggcctg     5580
tcagagcttg attagaagcc aagacagtgg cagcaaagga agacttggcc caggaaaaac    5640 ctgtggggttg tgctaatttc tgtccagaaa atagggtgga cagaagcttg tggggtacat    5700
ggaggaattg ggacctggtt atgttgttat tctcggactg tgaattttgg tgatgtaaaa     5760
cagaatattc tgtaaaccta atgtctgtat aaataatgag cgttaacaca gtaaaatatt     5820
caataagaag tcaaactact agggttaaaa aaaaaaaaa aaaa                       5864

<210> SEQ ID NO 56
<211> LENGTH: 8718
<212> TYPE: DNA
<213> ORGANISM: Homo sapiens

<400> SEQUENCE: 56
cctcccctcg cccggcgcgg tcccgtccgc ctctcgctcg cctcccgcct cccctcggtc      60
ttccgaggcg cccgggctcc cggcgcgcg gcggaggggg cggcaggcc ggcgggcggt       120 gatgtggcgg gactctttat gcgctgcggc aggatacgcg ctcggcgctg gacgcgact      180 gcgctcagtt ctctcctctc ggaagctgca gccatgatgg aagtttgaga gttgagccgc     240
tgtgaggcga ggccgggctc aggcgaggga gatgagagac ggcggcggcc gcggccgga     300 gccctctca gcgcctgtga gcagccgcg gggcagcgcc ctcggggagc cggccggcct      360
gcggcggcgg cagcggcggc gtttctcgcc tcctcttcgt ctttttctaac cgtgcagcct   420 cttcctcggc ttctcctgaa agggaaggtg gaagccgtgg gctcgggcgg gagccggctg    480
aggcgcggcg gcggcggcgg cacctcccgc tcctggagcg gggggagaa gcggcggcgg    540 cggcggccgc ggcggctgca gctccaggga gggggtctga gtcgcctgtc accatttcca     600
gggctgggaa cgccggagag ttggtctctc cccttctact gcctccaaca cggcggcgc      660 ggcggcggca catccaggga cccgggccgg ttttaaacct cccgtccgcc gccgccgcac    720
cccccgtggc ccgggctccg gaggccgccg gcggaggcag ccgttcggag gattattcgt     780
cttctcccca ttccgctgcc gccgctgcca ggcctctggc tgctgaggag aagcaggccc    840
agtcgctgca accatccagc agccgccgca gcagccatta cccggctgcg gtccagagcc     900
aagcggcggc agagcgaggg gcatcagcta ccgccaagtc cagagccatt tccatcctgc    960
agaagaagcc ccgccaccag cagcttctgc catctctctc ctccttttc ttcagccaca     1020 ggctcccaga catgacagcc atcatcaaag agatcgttag cagaaacaaa aggagatatc    1080
aagaggatgg attcgactta gacttgacct atatttatcc aaacattatt gctatgggat    1140
ttcctgcaga aagacttgaa ggcgtataca ggaacaatat tgatgatgta gtaaggtttt    1200
tggattcaaa gcataaaaac cattacaaga tatacaatct ttgtgctgaa agacattatg    1260
acaccgccaa atttaattgc agagttgcac aatatccttt tgaagaccat aacccaccac    1320
agctagaact tatcaaaccc ttttgtgaag atcttgacca atggctaagt gaagatgaca    1380
atcatgttgc agcaattcac tgtaaagctg gaaagggacg aactggtgta atgatatgtg    1440
catatttatt acatcggggc aaattttaa aggcacaaga ggccctagat ttctatgggg    1500
aagtaaggac cagagacaaa aagggagtaa ctattcccag tcagaggcgc tatgtgtatt    1560
attatagcta cctgttaaag aatcatctgg attatagacc agtggcactg ttgtttcaca    1620
```

```
agatgatgtt tgaaactatt ccaatgttca gtggcggaac ttgcaatcct cagtttgtgg    1680
tctgccagct aaaggtgaag atatattcct ccaattcagg acccacacga cgggaagaca    1740
agttcatgta ctttgagttc cctcagccgt tacctgtgtg tggtgatatc aaagtagagt    1800
tcttccacaa acagaacaag atgctaaaaa aggacaaaat gtttcacttt tgggtaaata    1860
cattcttcat accaggacca gaggaaacct cagaaaagt agaaaatgga agtctatgtg     1920
atcaagaaat cgatagcatt tgcagtatag agcgtgcaga taatgacaag gaatatctag    1980
tacttacttt aacaaaaaat gatcttgaca aagcaaataa agacaaagcc aaccgatact    2040
tttctccaaa ttttaaggtg aagctgtact tcacaaaaac agtagaggag ccgtcaaatc    2100
cagaggctag cagttcaact tctgtaacac cagatgttag tgacaatgaa cctgatcatt    2160
atagatattc tgacaccact gactctgatc cagagaatga accttttgat gaagatcagc    2220
atacacaaat tacaaaagtc tgaattttt tttatcaaga gggataaaac accatgaaaa     2280
taaacttgaa taaactgaaa atggaccttt ttttttttaa tggcaatagg acattgtgtc    2340
agattaccag ttataggaac aattctcttt tcctgaccaa tcttgtttta ccctatacat    2400
ccacagggtt ttgacacttg ttgtccagtt gaaaaaggt tgtgtagctg tgtcatgtat     2460 atacctttt gtgtcaaaag gacatttaaa attcaattag gattaataaa gatggcactt    2520 tcccgttta ttccagtttt ataaaaagtg gagacagact gatgtgtata cgtaggaatt     2580 ttttccttt gtgttctgtc accaactgaa gtggctaaag agctttgtga tatactggtt    2640
cacatcctac ccctttgcac ttgtggcaac agataagttt gcagttggct aagagaggtt    2700
tccgaagggt tttgctacat tctaatgcat gtattcgggt taggggaatg gagggaatgc    2760
tcagaaagga aataatttta tgctggactc tggaccatat accatctcca gctatttaca    2820
cacacctttc tttagcatgc tacagttatt aatctggaca ttcgaggaat tggccgctgt    2880
cactgcttgt tgtttgcgca tttttttta aagcatattg gtgctagaaa aggcagctaa    2940
aggaagtgaa tctgtattgg ggtacaggaa tgaaccttct gcaacatctt aagatccaca    3000
aatgaaggga tataaaaata atgtcatagg taagaaacac agcaacaatg acttaaccat    3060
ataaatgtgg aggctatcaa caaagaatgg gcttgaaaca ttataaaaat tgacaatgat    3120
ttattaaata tgttttctca attgtaacga cttctccatc tcctgtgtaa tcaaggccag    3180
tgctaaaatt cagatgctgt tagtacctac atcagtcaac aacttacact tattttacta    3240
gttttcaatc ataatacctg ctgtggatgc ttcatgtgct gcctgcaagc ttcttttttc    3300
tcattaaata taaaatattt tgtaatgctg cacagaaatt tcaatttga gattctacag     3360 taagcgtttt ttttctttga agatttatga tgcacttatt caatagctgt cagccgttcc    3420
acccttttga ccttacacat tctattacaa tgaattttgc agttttgcac attttttaaa    3480
tgtcattaac tgttagggaa ttttacttga atactgaata catataatgt ttatattaaa    3540
aaggacattt gtgttaaaaa ggaaattaga gttgcagtaa actttcaatg ctgcacacaa    3600
aaaaaagaca tttgatttt cagtagaaat tgtcctacat gtgctttatt gatttgctat    3660
tgaaagaata gggttttttt ttttttttt tttttttttt ttaaatgtgc agtgttgaat    3720
catttcttca tagtgctccc ccgagttggg actagggctt caatttcact tcttaaaaaa    3780
aatcatcata tatttgatat gcccagactg catacgattt taagcggagt acaactacta    3840
ttgtaaagct aatgtgaaga tattattaaa aaggtttttt tttccagaaa tttggtgtct    3900
tcaaattata ccttcacctt gacatttgaa tatccagcca ttttgtttct taatggtata    3960
```

```
aaattccatt ttcaataact tattggtgct gaaattgttc actagctgtg gtctgaccta    4020
gttaatttac aaatacagat tgaataggac ctactagagc agcatttata gagtttgatg    4080
gcaaatagat taggcagaac ttcatctaaa atattcttag taaataatgt tgacacgttt    4140
tccatacctt gtcagtttca ttcaacaatt tttaaatttt taacaaagct cttaggattt    4200
acacatttat atttaaacat tgatatatag agtattgatt gattgctcat aagttaaatt    4260
ggtaaagtta gagacaacta ttctaacacc tcaccattga aatttatatg ccaccttgtc    4320
tttcataaaa gctgaaaatt gttacctaaa atgaaaatca acttcatgtt ttgaagatag    4380
ttataaatat tgttctttgt tacaatttcg ggcaccgcat attaaaacgt aactttattg    4440
ttccaatatg taacatggag ggccaggtca taaataatga cattataatg ggcttttgca    4500
ctgttattat ttttcctttg gaatgtgaag gtctgaatga gggttttgat tttgaatgtt    4560
tcaatgtttt tgagaagcct tgcttacatt ttatggtgta gtcattggaa atggaaaaat    4620
ggcattatat atattatata tataaatata tattatacat actctcctta ctttatttca    4680
gttaccatcc ccatagaatt tgacaagaat tgctatgact gaaaggtttt cgagtcctaa    4740
ttaaaacttt atttatggca gtattcataa ttagcctgaa atgcattctg taggtaatct    4800
ctgagtttct ggaatatttt cttagacttt ttggatgtgc agcagcttac atgtctgaag    4860
ttacttgaag gcatcacttt taagaaagct tacagttggg ccctgtacca tcccaagtcc    4920
tttgtagctc ctcttgaaca tgtttgccat acttttaaaa gggtagttga ataaatagca    4980
tcaccattct tgctgtgggc acaggttata aacttaagtg gagtttaccg gcagcatcaa    5040
atgtttcagc tttaaaaaat aaaagtaggg tacaagttta atgtttagtt ctagaaattt    5100
tgtgcaatat gttcataacg atggctgtgg ttgccacaaa gtgcctcgtt tacctttaaa    5160
tactgttaat gtgtcatgca tgcagatgga aggggtggaa ctgtgcacta aagtgggggc    5220
tttaactgta gtatttggca gagttgcctt ctacctgcca gttcaaaagt tcaacctgtt    5280
ttcatataga atatatatac taaaaaattt cagtctgtta aacagcctta ctctgattca    5340
gcctcttcag atactcttgt gctgtgcagc agtggctctg tgtgtaaatg ctatgcactg    5400
aggatacaca aaaataccaa tatgatgtgt acaggataat gcctcatccc aatcagatgt    5460
ccatttgtta ttgtgtttgt taacaaccct ttatctctta gtgttataaa ctccacttaa    5520
aactgattaa agtctcattc ttgtcattgt gtgggtgttt tattaaatga gagtttataa    5580
ttcaaattgc ttaagtccat tgaagttta attaatgggc agccaaatgt gaatacaaag    5640
ttttcagttt tttttttttcc tgctgtcctt caaagcctac tgtttaaaaa aaaaaaaaaa    5700
aaaaaacatg gcctgagagt agagtatctg tctactcatg tttaattaag gaaaaacact    5760
tatttttagg gctttagtca tcacttcata aattgtataa gcacattaaa tagcgttcta    5820
gtcctgaaaa agtccaagat tcttagaaaa ttgtgcatat ttttattatg acagatgttt    5880
gaagataatt ccccagaatg gatttgatac tttagatttc aattttgtgg cttttgtcta    5940
ttattctgta ctctgccatc agcatatgga aagcttcatt tactcatcat gacttgtgcc    6000
atataaaaat tgatatttcg gaatagtcta aaggactttt tgtacttgaa tttaatcatg    6060
ttgtttctaa tattccttaaa agcttgaaga ctaaagcata tcctttcaac aaagcatagt    6120 aagtaataa gaaagtgtag tttgtacaag tgttaaaaaa ataaagtaga caatgttaca    6180
gtgggactta ttatttcaag tttacatttt ctccatgtaa ttttttaaaa agtaaatgaa    6240
aaaatgtgca ataatgtaaa atatgaagtg tatgtgtaca cacatttat ttttcggtat    6300 cttgggtata cgtatggttg aaaactatac tggagtctaa aagtattcta atttataaga    6360
```

```
agacattttg gtgatgtttg aaaaatagaa atgtgctagt tttgttttta tatcatgtcc    6420
tttgtacgtt gtaatatgag ctggcttggt tcagtaaatg ccatcaccat ttccattgag    6480
aatttaaaac tcaccagtgt ttaatatgca ggcttccaaa ggcttatgaa aaaaatcaag    6540
acccttaaat ctagttaatt tgctgctaac atgaaactct ttggttcttt tatttttgcc    6600
agataattag acacacatct aaagcttagt cttaaatggc ttaagtgtag ctattgatta    6660
gtgctgttgc tagttcagaa agaaatgttt gtgaatggaa acaagaatat tcagtccaaa    6720
ctgttgtaag gacagtacct gaaaccagg aaacaggata atggaaaaag tcttttaaag    6780
atgaaatgtt ggagccaact ttcttataga attaattgta tgtggctata gaaagcctaa    6840
tgattgttgc ttattttga gagcatatta ttcttttatg accataatct tgctgttttt    6900
ccatcttcca aaagatcttc cttcaatat gtatatcaga atgtgggtag ccagtcagac    6960
aaattcatat tggttggtag ctttaaaag tttgtaatgt gaagacagga aaggacaaaa    7020
tagtttgctt tggtggtagt actctggttg ttaagctagg tattttgaga ctacttcccc    7080
atcacaacaa caataaaata atcactcata atcctatcac ctggagacat agccatcgtt    7140
aatatgttag tgactataca atcatgtttt cttctgtata tccatgtata ttctttaaaa    7200
atgaaattta tactgtacct gatctcaaag cttttagct tagtatatct gtcatgaatt    7260
tgtaggatgt tccattgcat cagaaaacgg acagtgattt gattactttc taatgccaca    7320
gatgcagatt acatgtagtt attgagaatc ctttcgaatt cagtggctta atcatgaatg    7380
tctaaatatt gttgacatta ggatgataca tgtaaattaa agttacattt gtttagcata    7440
gacaagctta acattgtaga tgtttctctt caaaaatcat cttaaacatt tgcatttgga    7500
attgtgttaa atagaatgtg tgaaacactg tattagtaaa cttcatcacc tttctacttc    7560
cttatagttt gaacttttca gttttttgtag ttcccaaaca gttgctcaat ttagagcaaa    7620
ttaatttaac acctgccaaa aaaaggctgc tgttggctta tcagttgtct ttaaattcaa    7680
atgctcatgt gacttttatc acatcaaaaa atatttcatt aatgattcac ctttagctct    7740
gaaaattacc gcgttagta attatagtgg gcttataaaa acatgcaact ctttttgata    7800
gttatttgag aattttggtg aaaaatattt agctgagggc agtatagaac ttataaacca    7860
atatattgat atttttaaaa cattttaca tataagtaaa ctgccatctt tgagcataac    7920
tacatttaaa aataaagctg catattttta aatcaagtgt ttaacaagaa tttatatttt    7980
ttatttttta aaattaaaaa taatttatat ttcctctgtt gcatgaggat tctcatctgt    8040
gcttataatg gttagagatt ttatttgtgt ggaatgaagt gaggcttgta gtcatggttc    8100
tagtgtttca gtttgccaag tctgtttact gcagtgaaat tcatcaaatg tttcagtgtg    8160
gttttctgta gcctatcatt tactggctat ttttttatgt acacctttag gatttttctgc    8220 ctactctatc cagttgtcca aatgatatcc tacattttac aaatgcccct tcagtttcta    8280 ttttctttt ccattaaatt gccctcatgt cctaatgtgc agtttgtaag tgtgtgtgtg    8340
tgtgtctgtg tgtgtgtgaa tttgattttc aagagtgcta gacttccaat ttgagagatt    8400
aaataattta attcaggcaa acattttca ttggaatttc acagttcatt gtaatgaaaa    8460
tgttaatcct ggatgacctt tgacatacag taatgaatct tggatattaa tgaatttgtt    8520
```

```
agtagcatct tgatgtgtgt tttaatgagt tattttcaaa gttgtgcatt aaaccaaagt    8580
tggcatactg gaagtgttta tatcaagttc catttggcta ctgatggaca aaaaatagaa    8640
atgccttcct atggagagta tttttccttt aaaaaattaa aaaggttaat tattttgact    8700
aaaaaaaaaa aaaaaaaa                                                   8718
```